United States Patent
Wang

(10) Patent No.: US 11,124,553 B2
(45) Date of Patent: Sep. 21, 2021

(54) TDP-43 MITOCHONDRIAL LOCALIZATION INHIBITOR FOR THE TREATMENT OF NEUROGENERATIVE DISEASE

(71) Applicant: Case Western Reserve University, Cleveland, OH (US)

(72) Inventor: Xinglong Wang, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/090,786

(22) PCT Filed: Apr. 7, 2017

(86) PCT No.: PCT/US2017/026675
§ 371 (c)(1),
(2) Date: Oct. 2, 2018

(87) PCT Pub. No.: WO2017/177178
PCT Pub. Date: Oct. 12, 2017

(65) Prior Publication Data
US 2019/0211070 A1   Jul. 11, 2019

Related U.S. Application Data

(60) Provisional application No. 62/319,580, filed on Apr. 7, 2016, provisional application No. 62/328,484, filed on Apr. 27, 2016.

(51) Int. Cl.
*C07K 14/47* (2006.01)
*C07K 7/06* (2006.01)
*A61K 38/00* (2006.01)
*A61P 25/28* (2006.01)

(52) U.S. Cl.
CPC .......... *C07K 14/4713* (2013.01); *A61P 25/28* (2018.01); *C07K 7/06* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,858,683 | A * | 1/1999 | Keesee | G01N 33/6848 435/7.1 |
| 6,833,355 | B1 * | 12/2004 | Bjorck | A61P 31/00 514/3.7 |
| 8,334,255 | B2 | 12/2012 | Zhang et al. | |
| 2007/0014803 | A1 * | 1/2007 | Lu | C07K 14/35 424/160.1 |
| 2012/0058137 | A1 * | 3/2012 | Bonny | A61P 19/00 424/188.1 |
| 2013/0302313 | A1 * | 11/2013 | Yu | C12N 15/86 424/130.1 |
| 2015/0045248 | A1 | 2/2015 | Takahashi et al. | |
| 2015/0065384 | A1 | 3/2015 | Cairns et al. | |
| 2015/0320848 | A1 * | 11/2015 | Rammensee | C07K 14/47 424/185.1 |

FOREIGN PATENT DOCUMENTS

WO    WO 98/09170    *  5/1998  ........... G01N 33/574
WO    2013129603 A1    9/2013

OTHER PUBLICATIONS

Shin et al., Biomed Mater Res Part A 2014:102A:575-587 (Year: 2014).*
Watanabe et al., Molecular Brain, 2020; 13: 8 (Year: 2020).*
Anthony King, Nature, 2018 559: S13 (Year: 2018).*
Chanson et al., Neurodegenerative Dis 2010; 7: 260-264 (Year: 2010).*
Bhattacharya et al., PLoS ONE 12(3): e0171355. https://doi.org/10.1371/journal.pone.0171355; 22 pages total (Year: 2017).*
Gu et al., Nucleic Acids Research, 2017, vol. 45, No. 10 6177-6193 (Year: 2017).*
Fenton et al., Medicinal Chemistry Research (2020) 29:1133-1146 (Year: 2020).*
Liu et al., "Reducing TDP-43 aggregation does not prevent its cytotoxicity". Acta Neuropathologica Communications, Aug. 9, 2013, vol. 1, No. 49.
Wang et al., "The inhibition of TDP-43 mitochondrial localization blocks its neuronal toxicity". Nature Medicine ePub., Jun. 27, 2016, vol. 22, No. 8, pp. 869-878.
"Human TDP-43 protein (residues 2-106).", XP002788468, Jun. 20, 2013.
"Human TAR DNA binding protein 43 (TDP-43) protein sequence.", XP002788467, Feb. 5, 2009.
Extended Search Report for Patent Application No: 17779936.8-1120/3440094, dated Feb. 20, 2019.
Wenzhang Wang et al: "The inhibition of TDP-43 mitochondrial localization blocks its neuronal toxicity", Nature Medicine, vol. 22, No. 8, Jun. 27, 2016 (Jun. 27, 2016), pp. 869-878.
H Brooks et al: "Tat peptide-mediated cellular delivery: back to basics", Advanced Drug Delivery Reviews, vol. 57. No. 4, Feb. 28, 2005 (Feb. 28, 2005), pp. 559-577.
Casey Cook et al: "TDP-43 in neurodegenerative disorders", Expert Opinion on Biological Therapy, vol. 8, No. 7, Jun. 12, 2008 (Jun. 12, 2008), pp. 969-978.
Y. M. Ayala et al: "Structural and shuttling of TDP-43", Journal of Cell Science, vol. 121, No. 22, Oct. 28, 2008 (Oct. 28, 2008), pp. 3778-3785.
"HIV-I tat PTD peptide (47-57) construct, SEQ ID 2.", XP002788466, Jan. 2, 2014.

(Continued)

*Primary Examiner* — Christina M Borgeest
(74) *Attorney, Agent, or Firm* — Tarolli, Sundheim, Covell & Tummino LLP

(57) ABSTRACT

A method of treating a neurodegenerative disease in a subject includes administering to the subject a therapeutically effective amount of a TDP-43 mitochondrial localization inhibitor.

6 Claims, 26 Drawing Sheets
Specification includes a Sequence Listing.

(56) References Cited

OTHER PUBLICATIONS

Office action for European Patent Application No: 17779936.8, dated Jul. 18, 2019.
Office Action for Japanese Patent Application No. 2018-552826, dated May 25, 2021, 6 pgs.

* cited by examiner

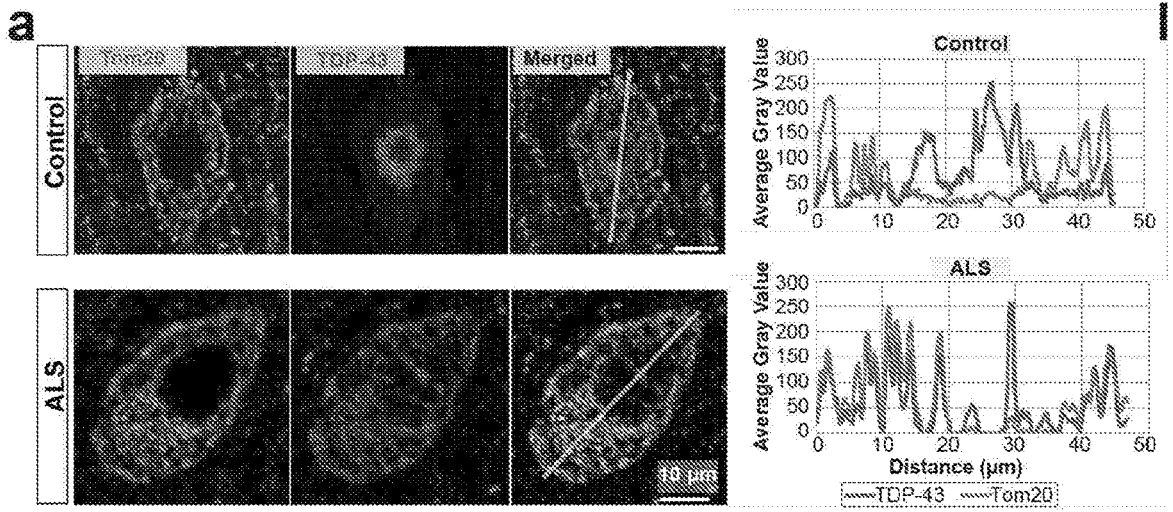
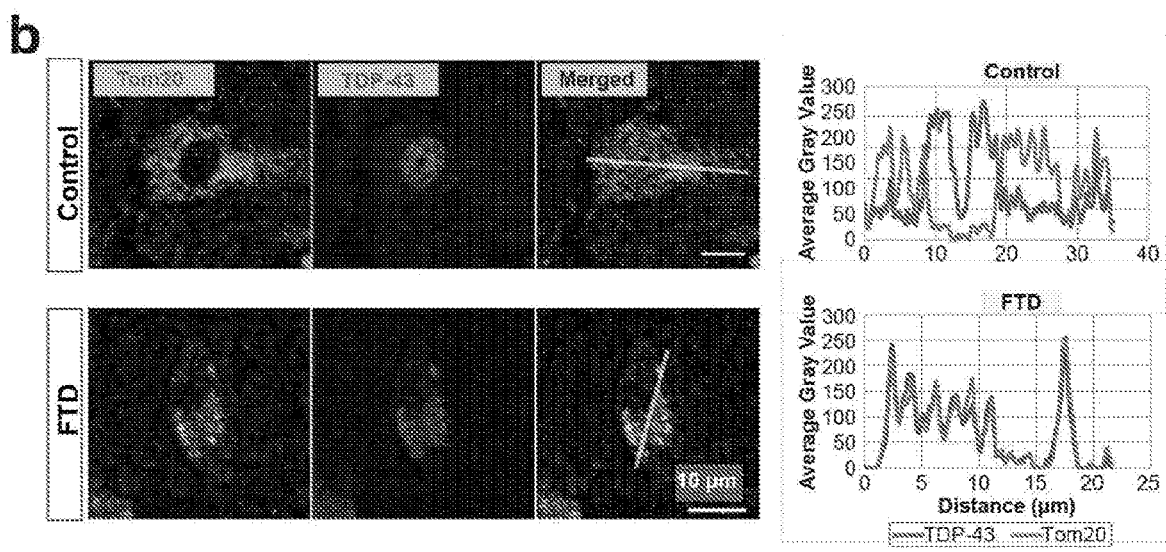
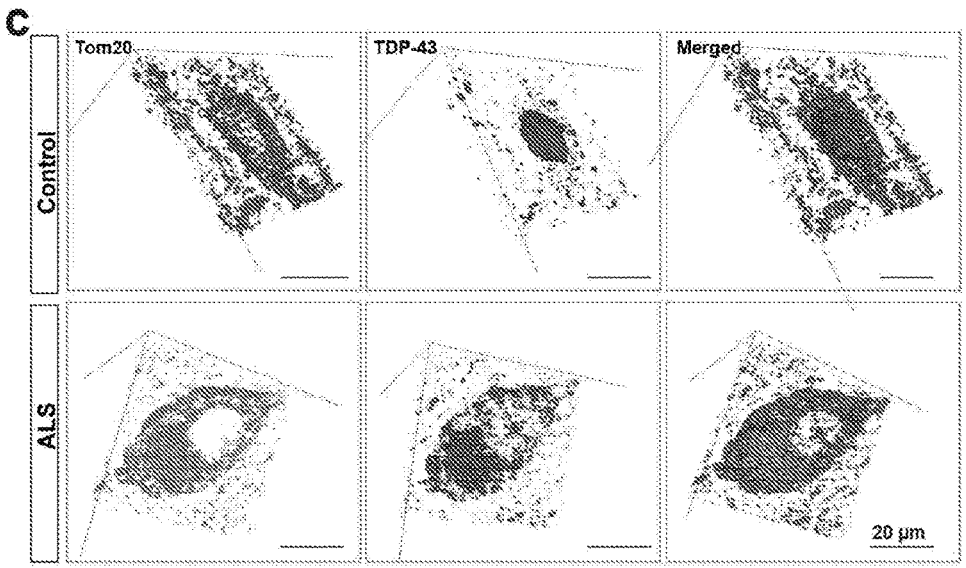
Figs. 1A-C

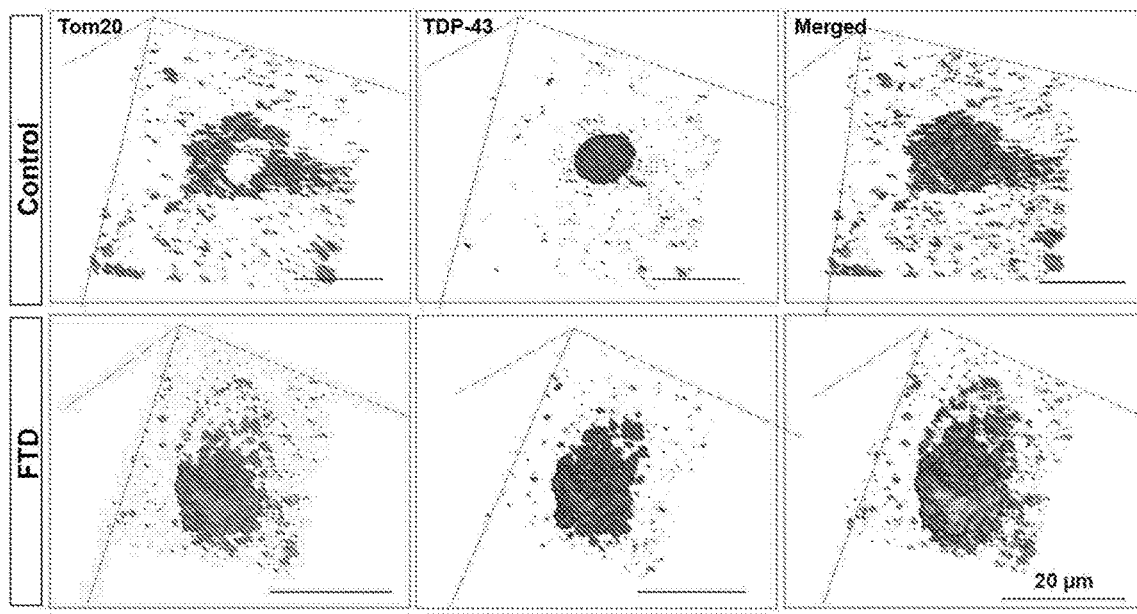
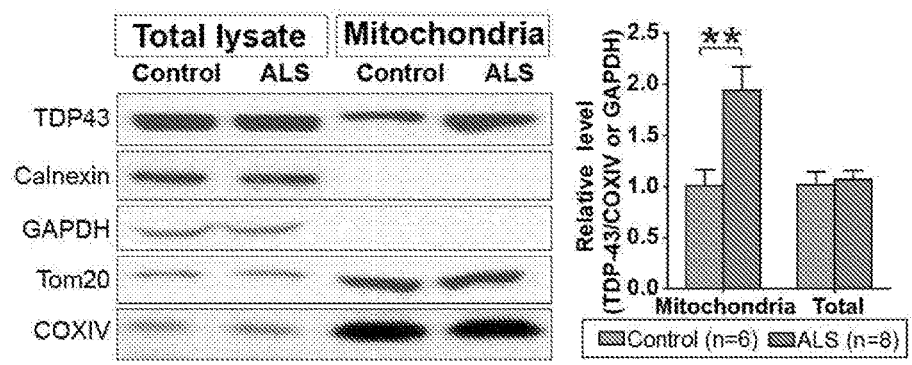
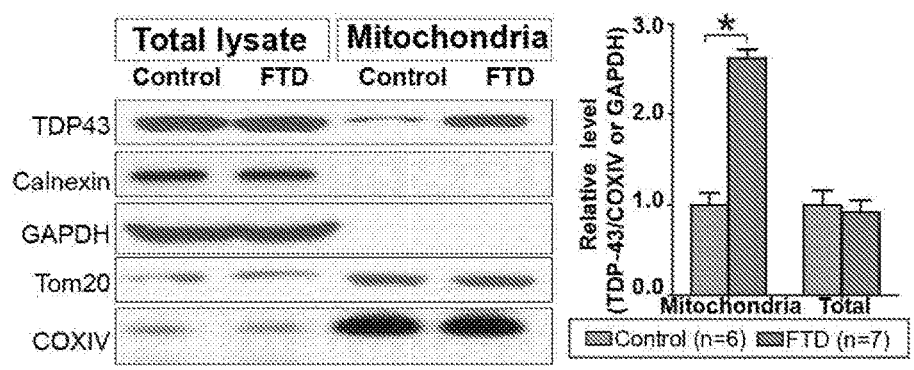
Figs. 1D-F

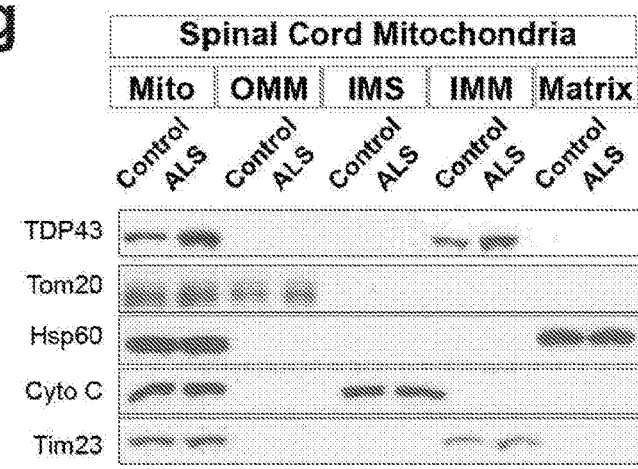
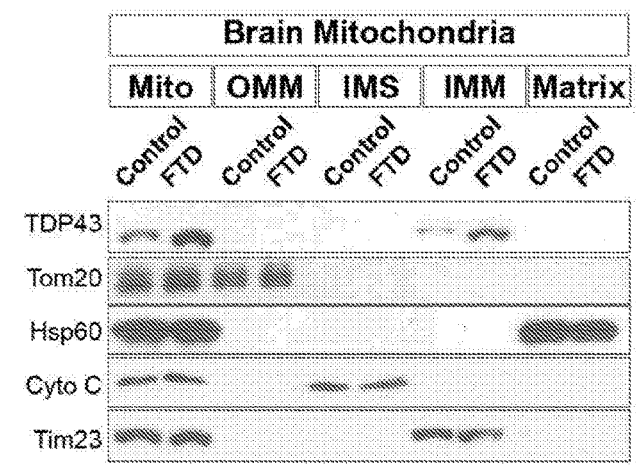
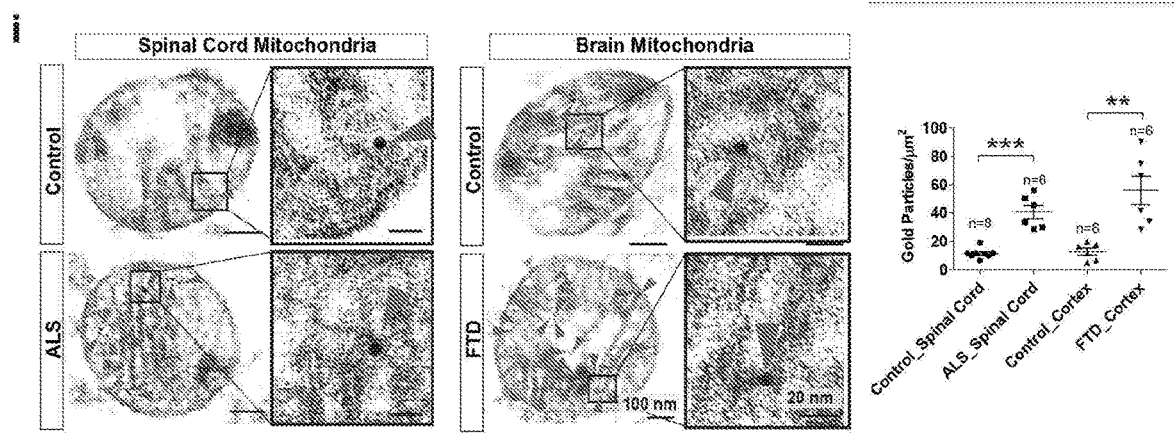
Figs. 1A-I

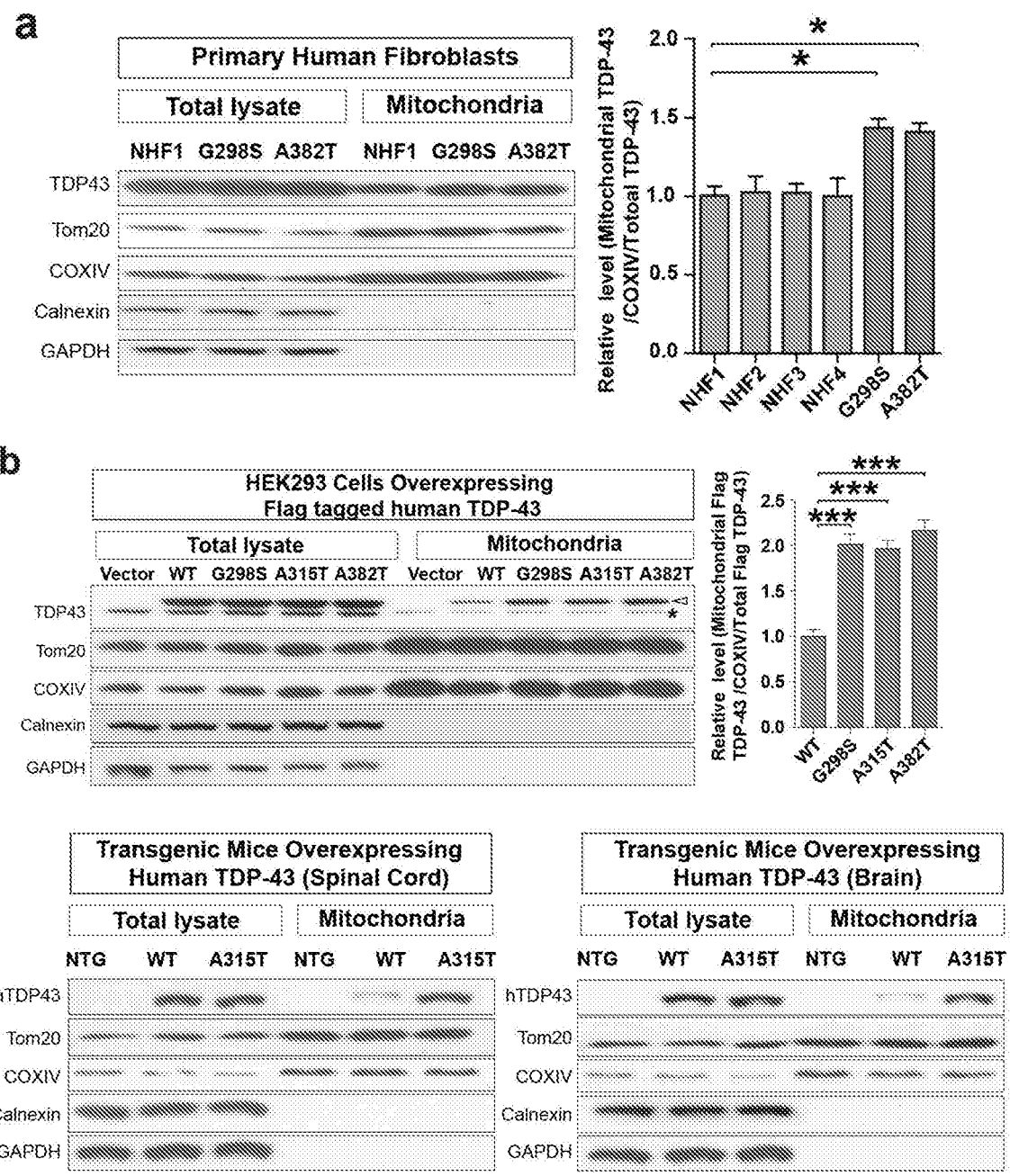
Figs. 2A-C

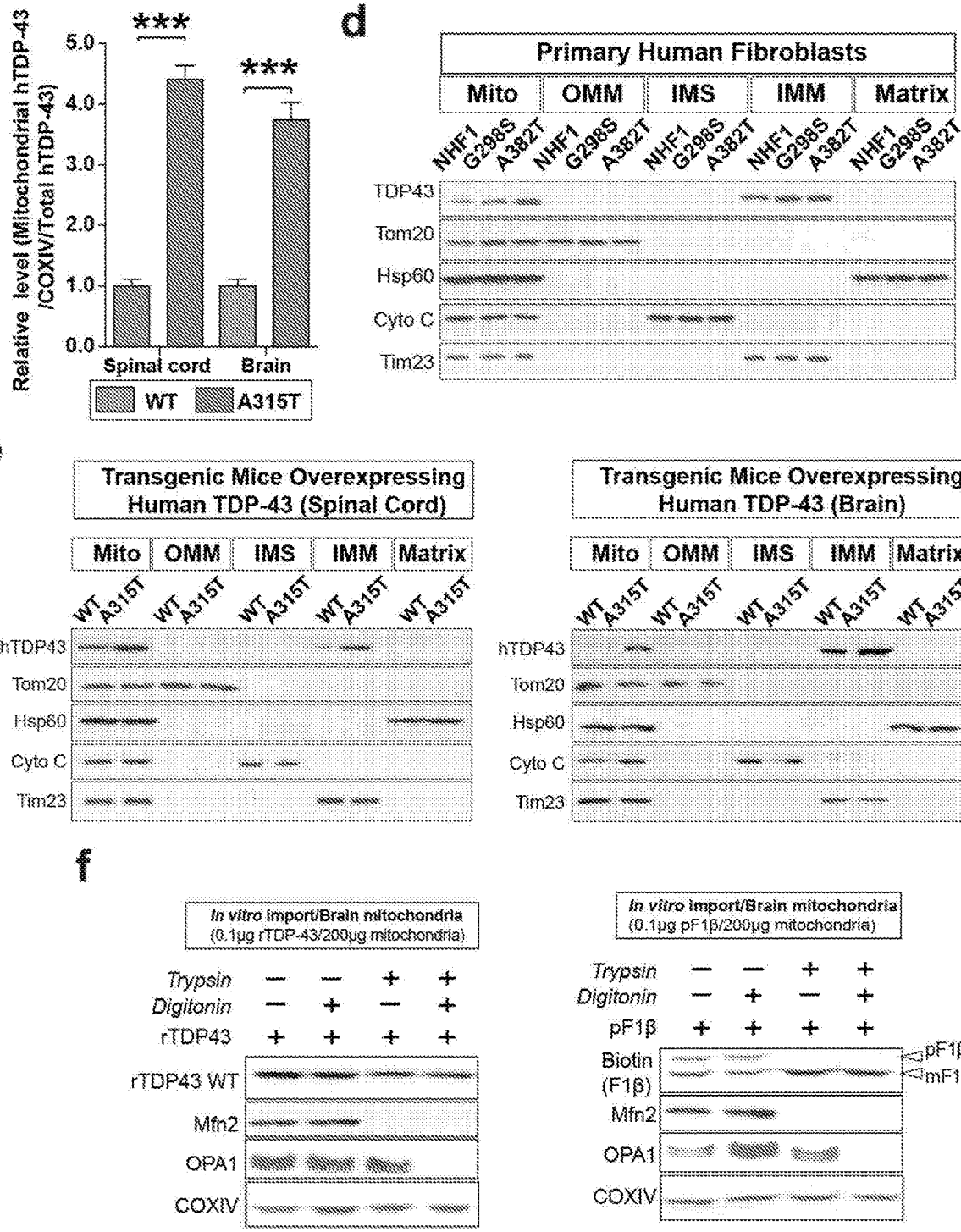
Figs. 2D-F

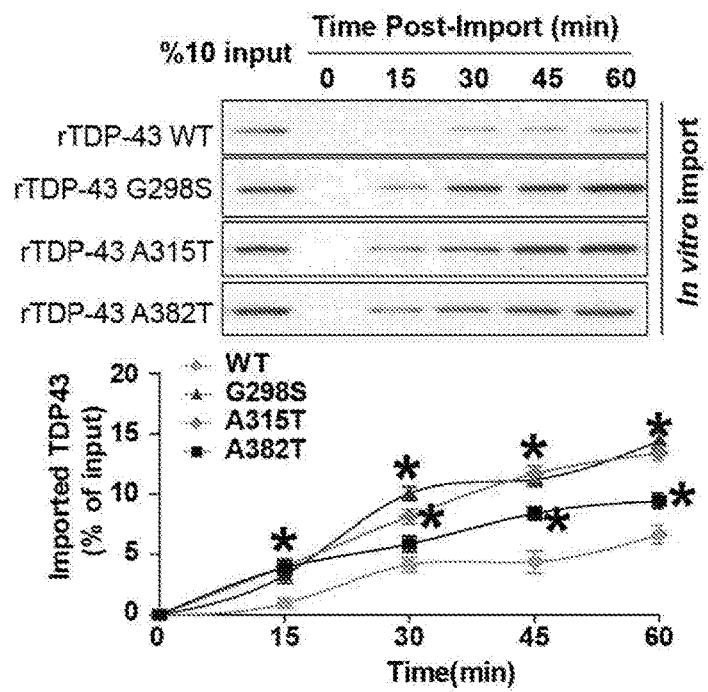
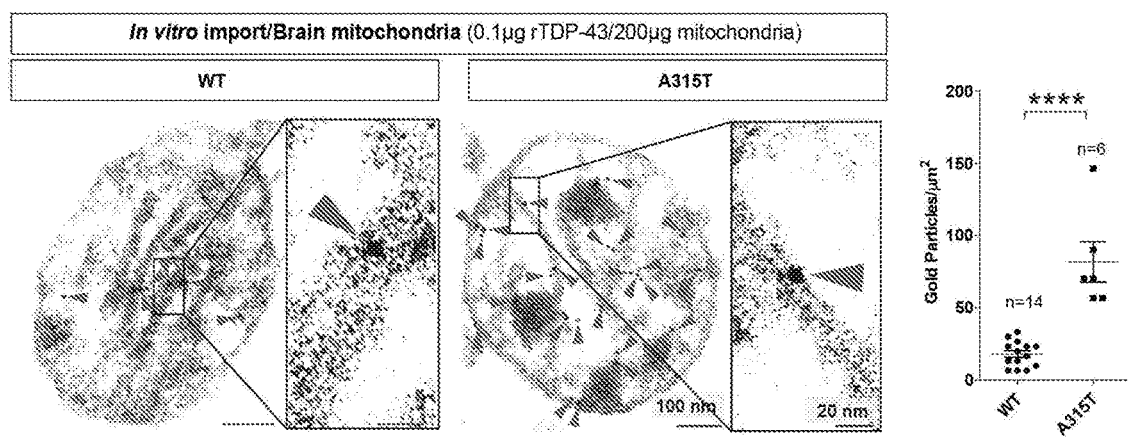
Figs. 2G-H a

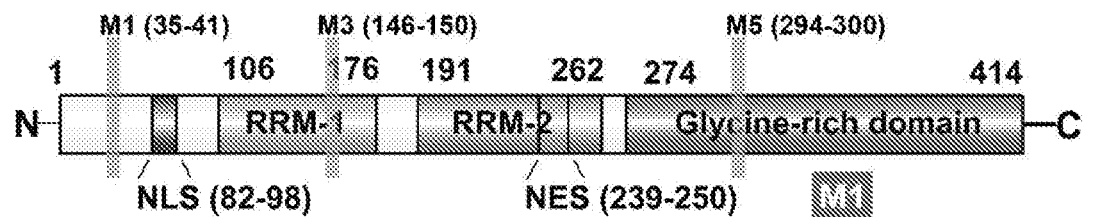

```
  1 MSEYIRVTED ENDEPIEIPS EDDGTVLLST VTAQFPGACG IRYRNPVSQC
 51 MRGVRLVEGI LHAPDAGWGN LVYVVNYPKD NKRKMDETDA SSAVKVKRAV
101 QKTSDLIVLG LPWKTTEQDL KEYFSTFGEV LMVQVKKDLK TGHSKGFGFV
151 RFTEYETQVK VMSQRHMIDG RWCDKLPNSK SQDEPLRS   RKVFVGRCTE
201 DMTEDELREF FSQYGDVMDV FIPKPFRAFA FVTFADDQIA QSLCGEDLII
251 KGISVHISNA EPKHNSNRQL ERSGRFGGNP GGFGNQGGFG NSRGGGAGLG
301 NNQGSNMGGG MNFGAFSINP AMMAAAQAAL QSSWGMMGML ASQQNQSGPS
351 GNNQNQGNMQ REPNQAFGSG NNSYSGSNSG AAIGWGSASN AGSGSGFNGG
401 FGSSMDSKSS GWGM
``` b

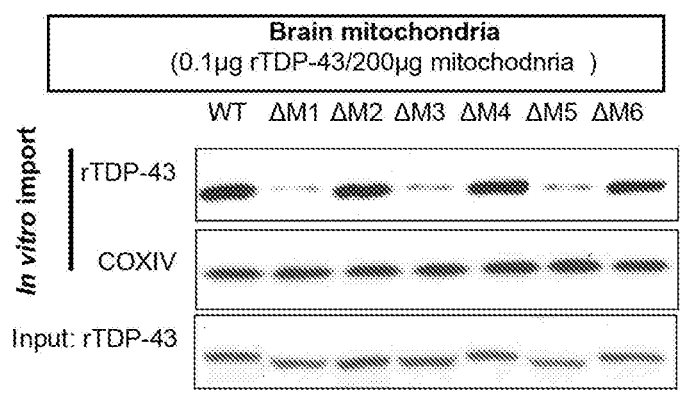 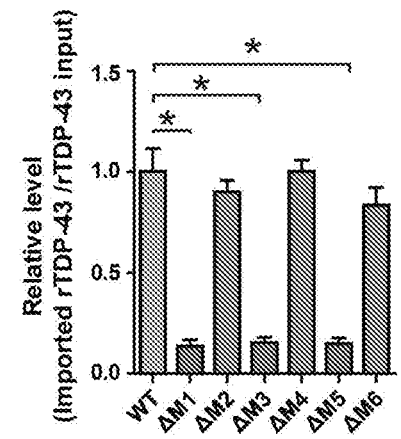

c

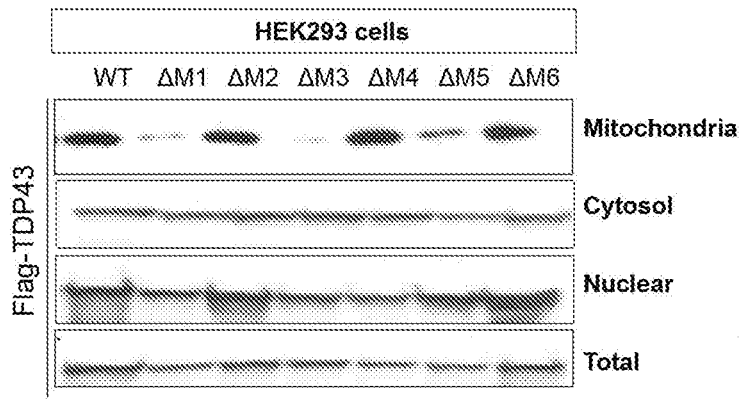 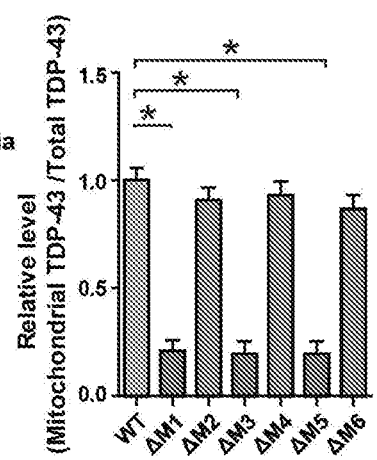

Figs. 3A-C

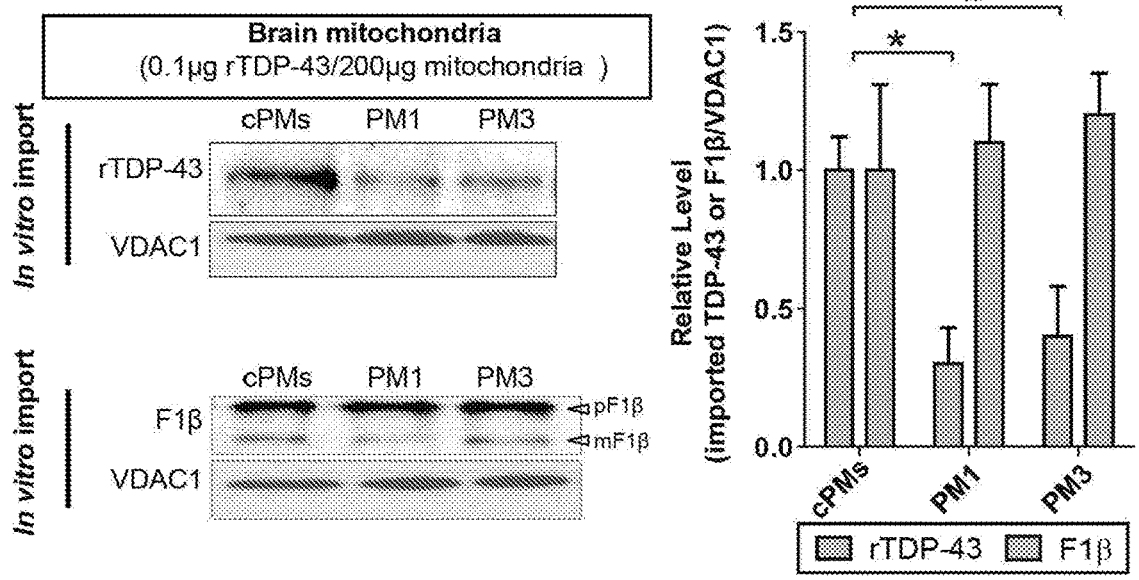
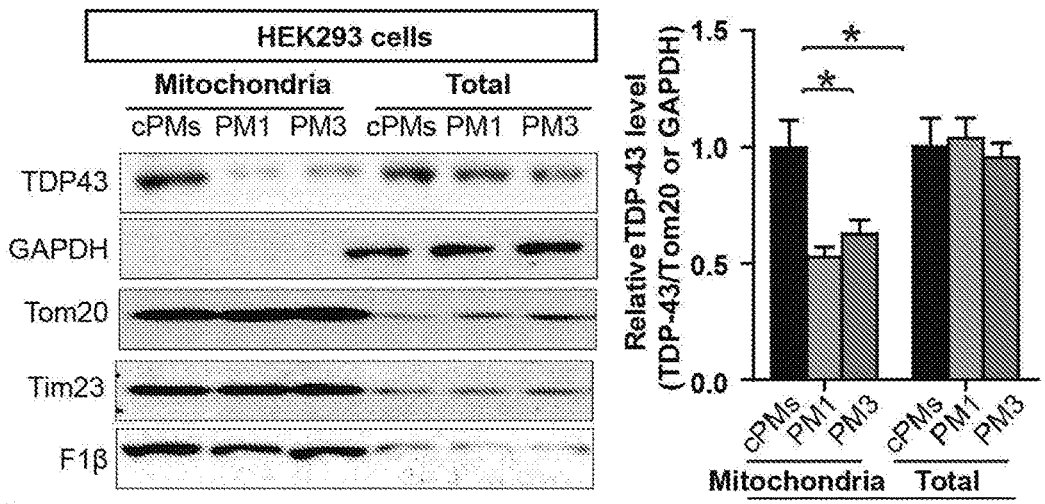
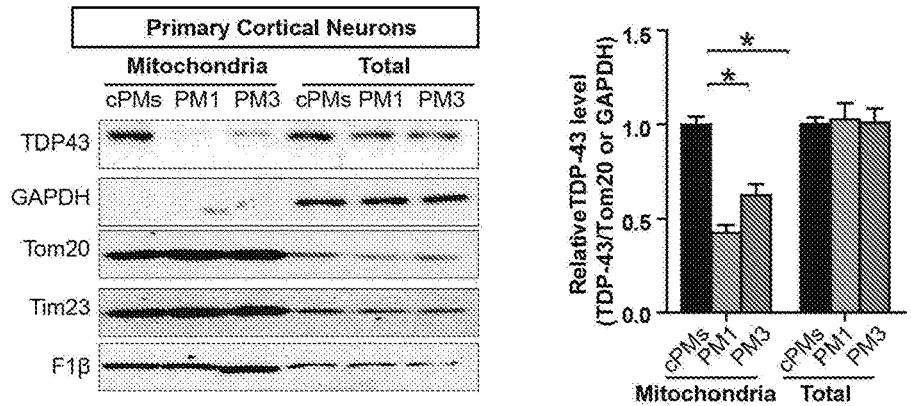
Figs. 3D-F

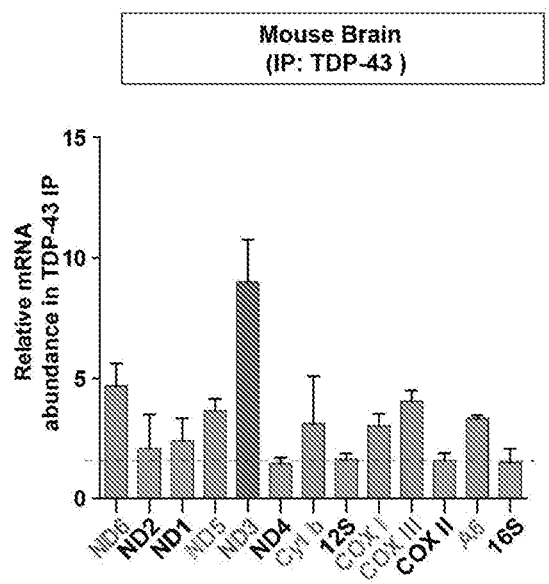
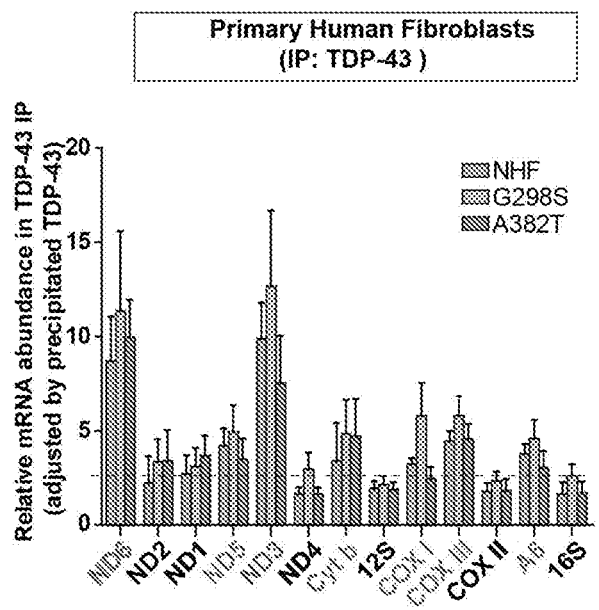
Figs. 4B-C

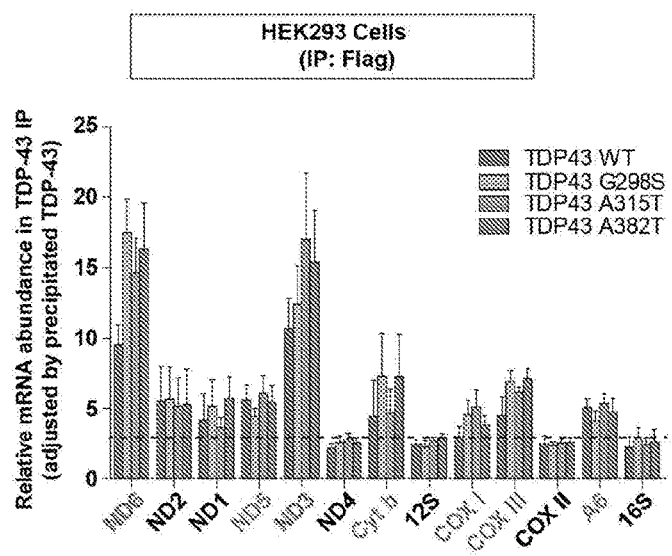
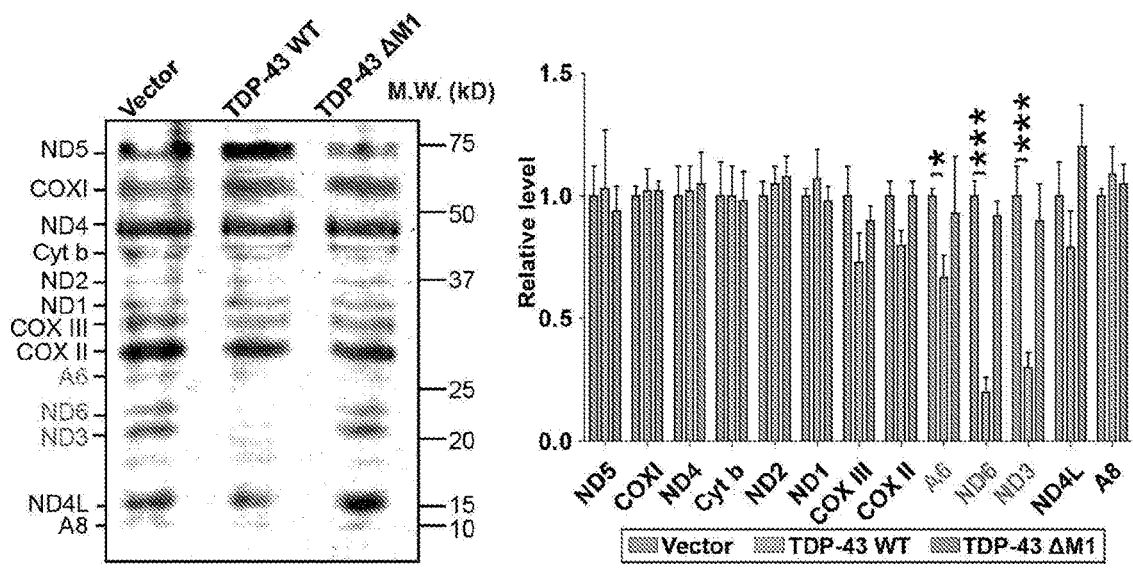
Figs. 4D-E

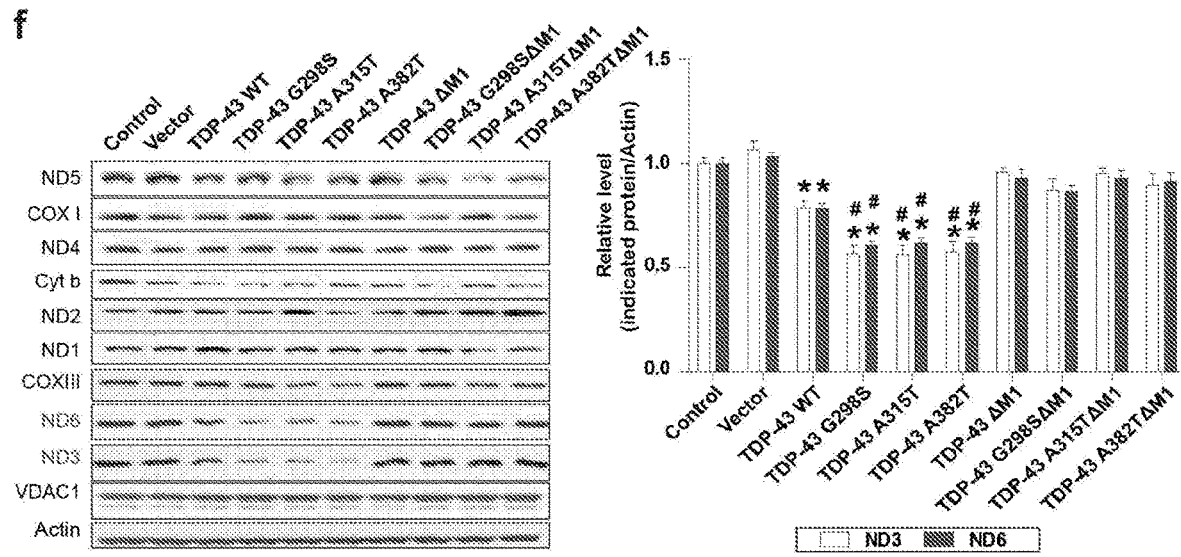
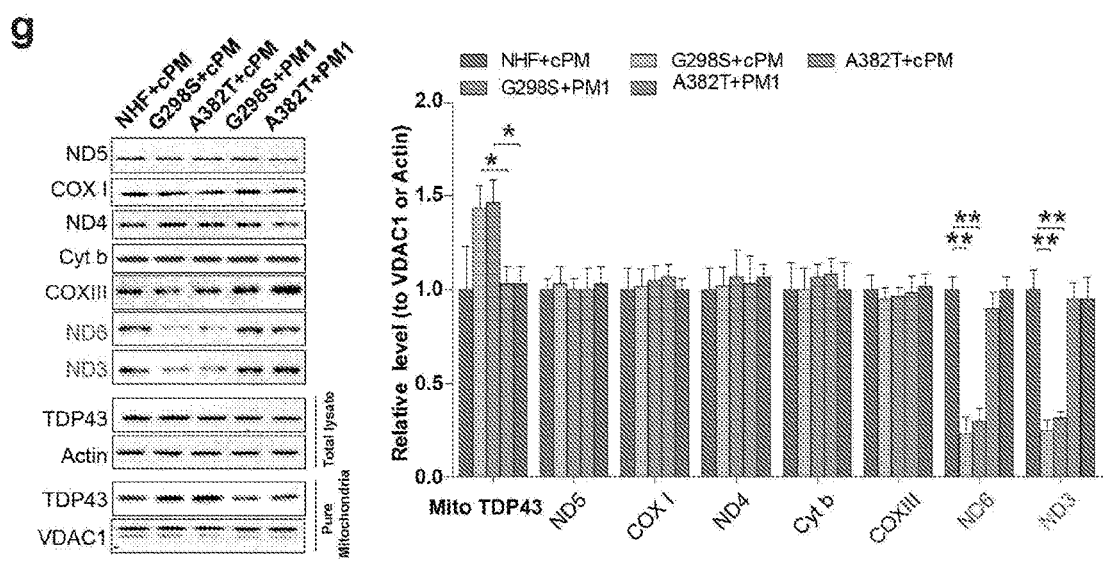
Figs. 4F-G

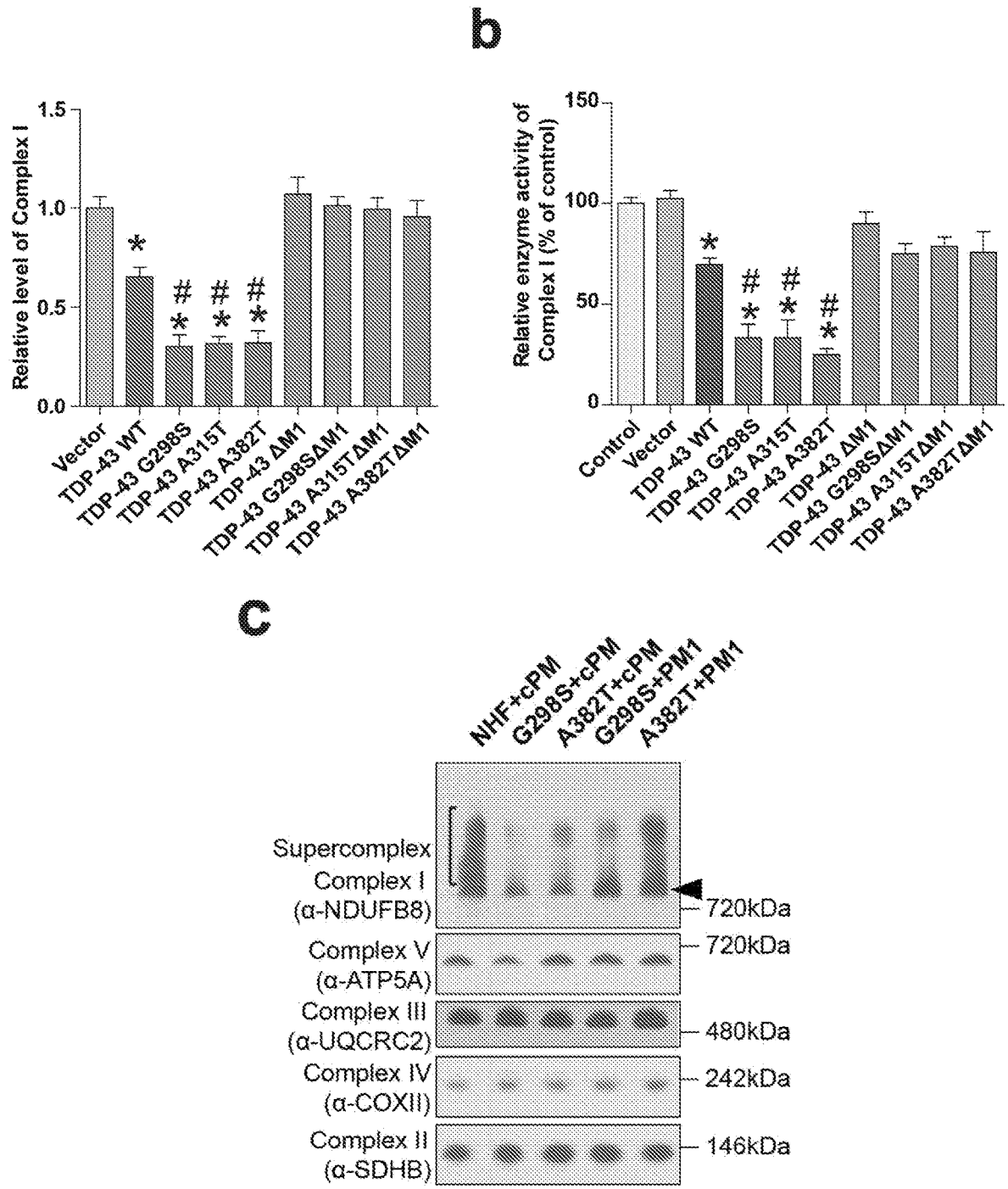
Figs. 5B-C

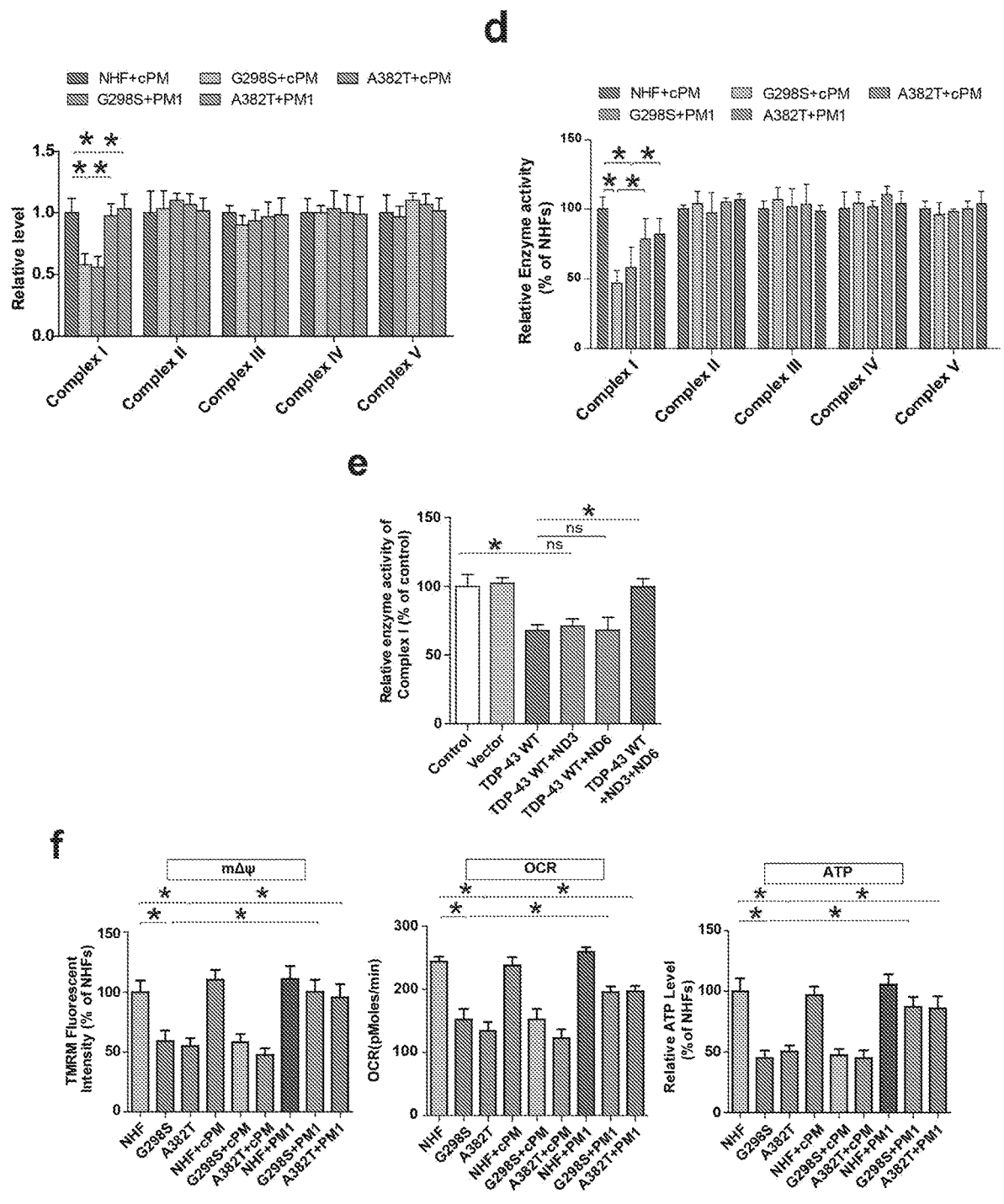
Figs. 5D-F

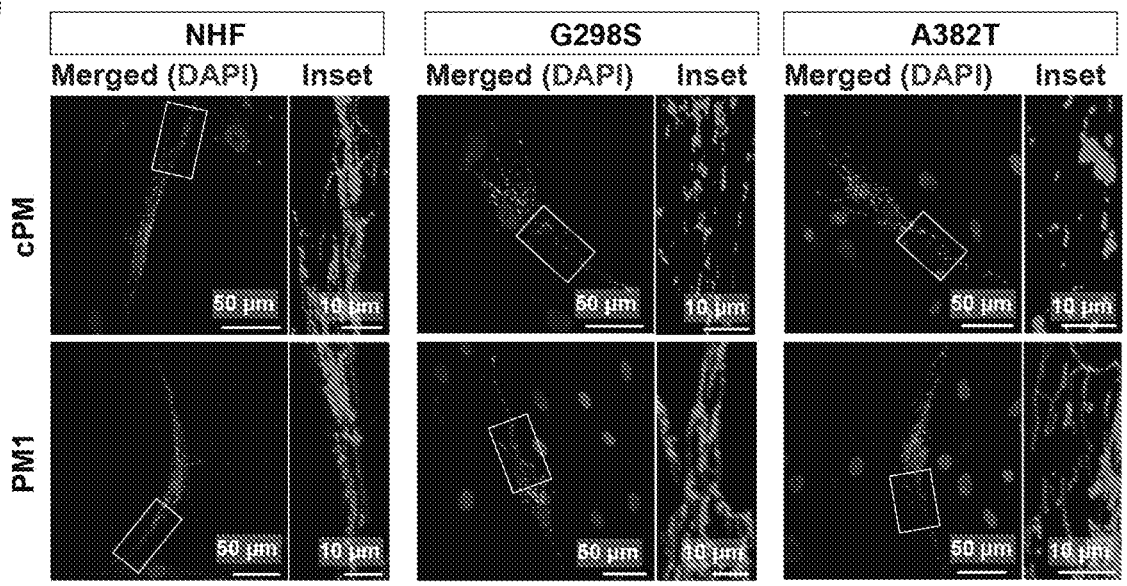
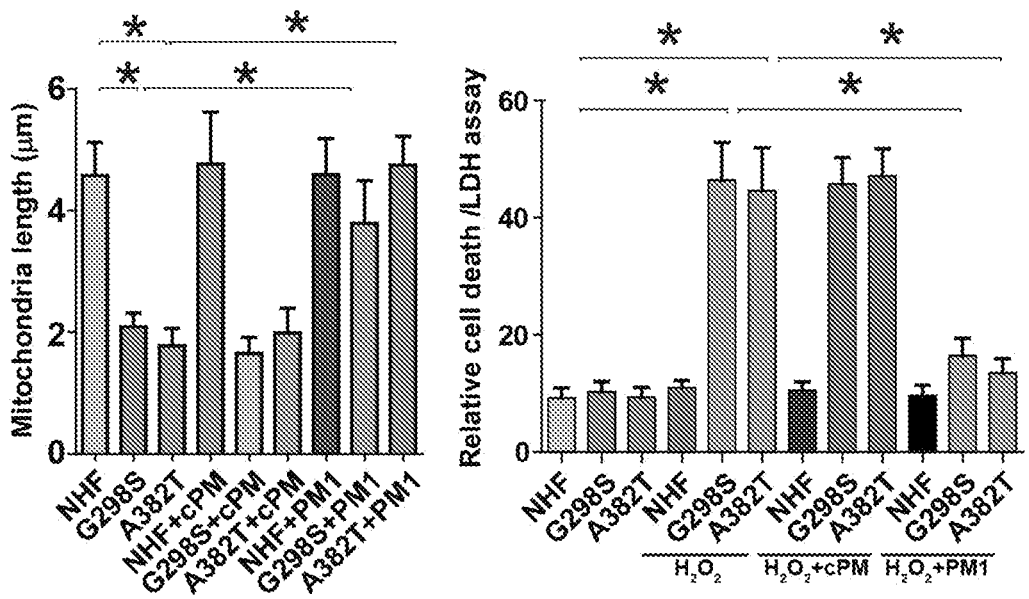
Figs. 5G-H

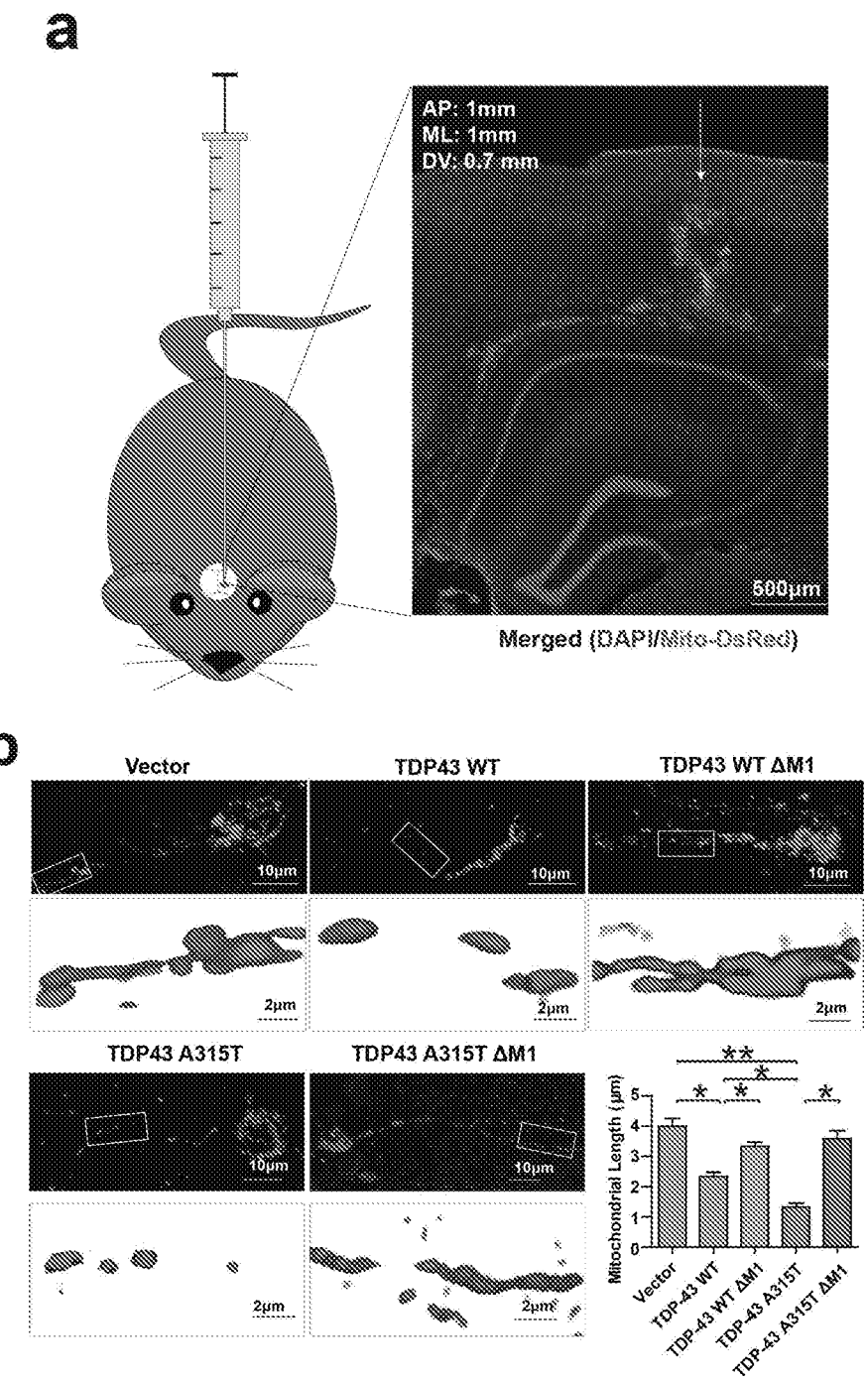
Figs. 6A-B

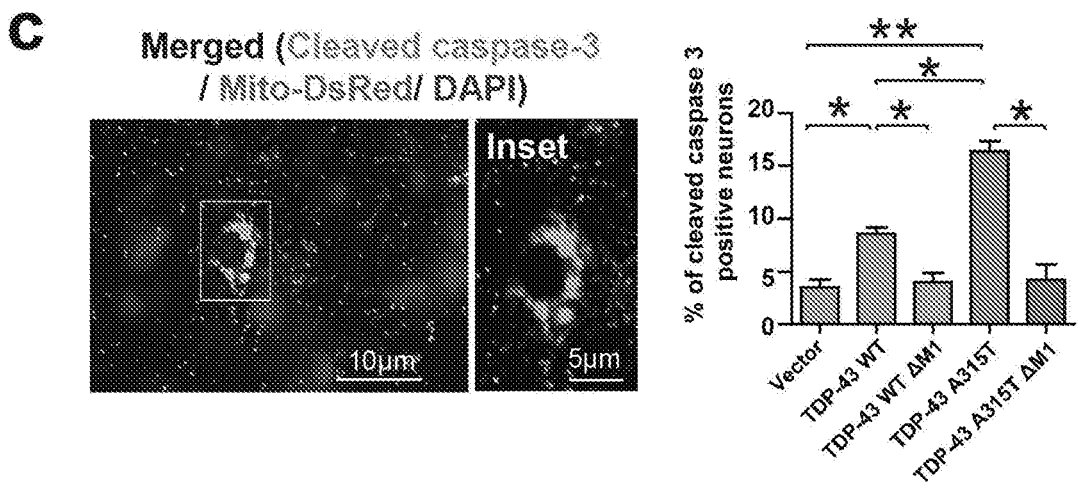
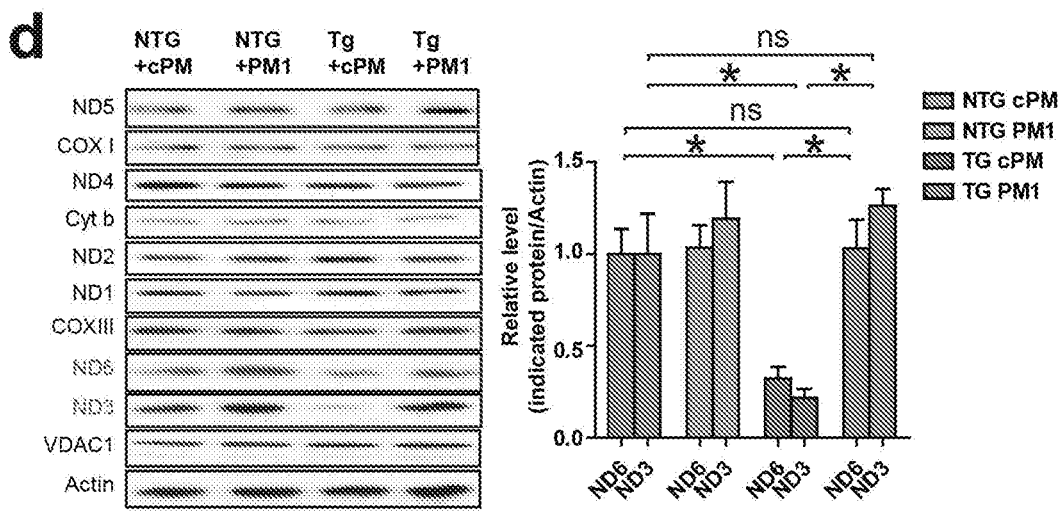
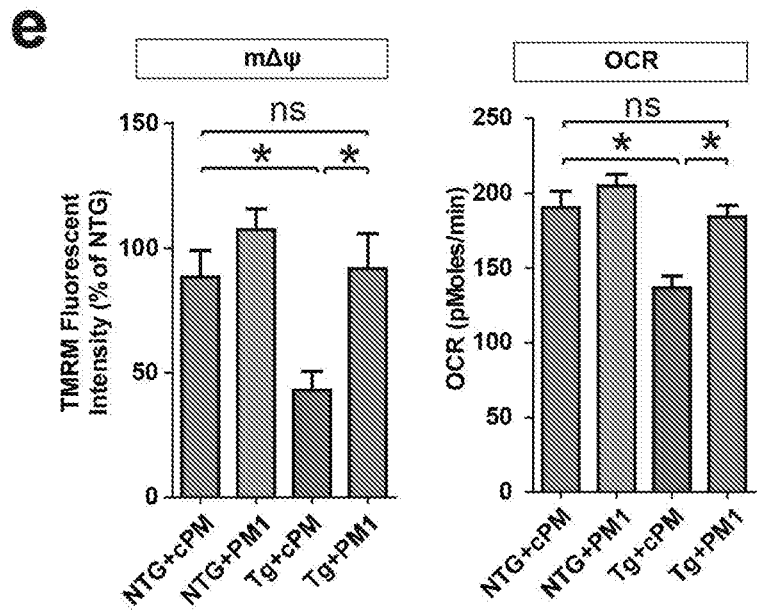
Figs. 6C-F

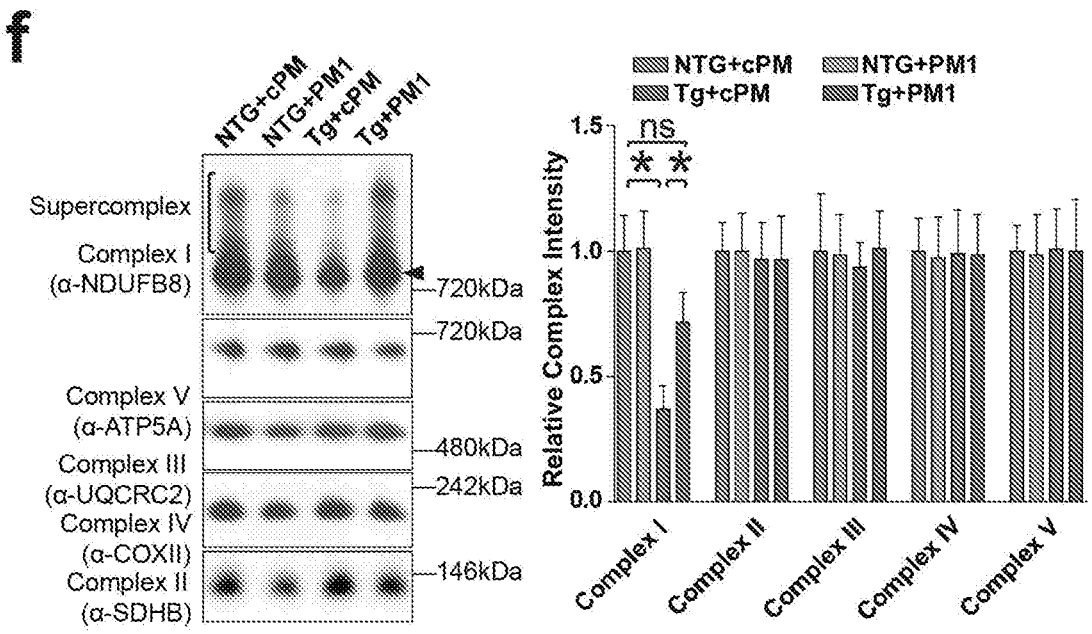
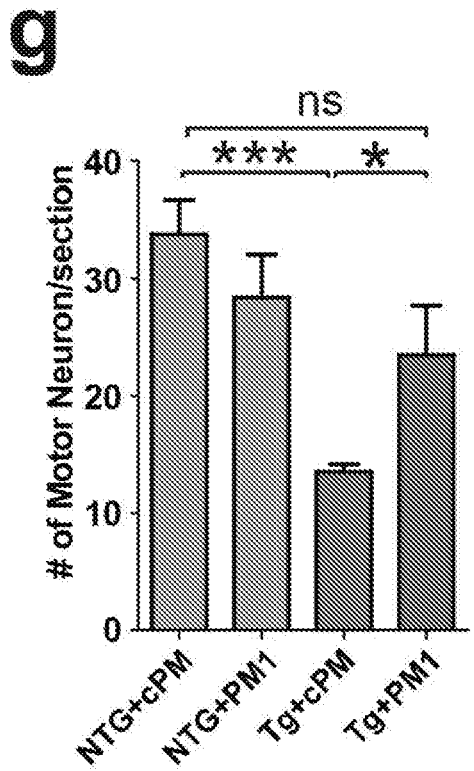
Figs. 6F-G

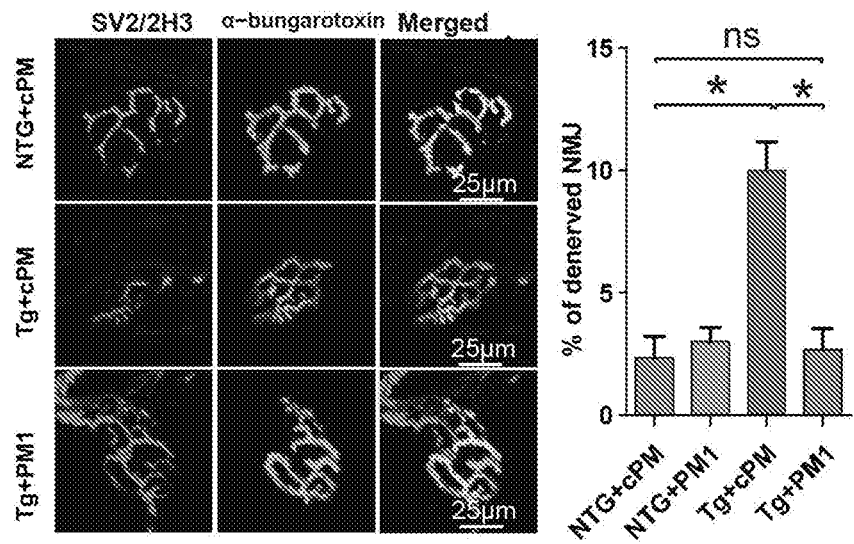
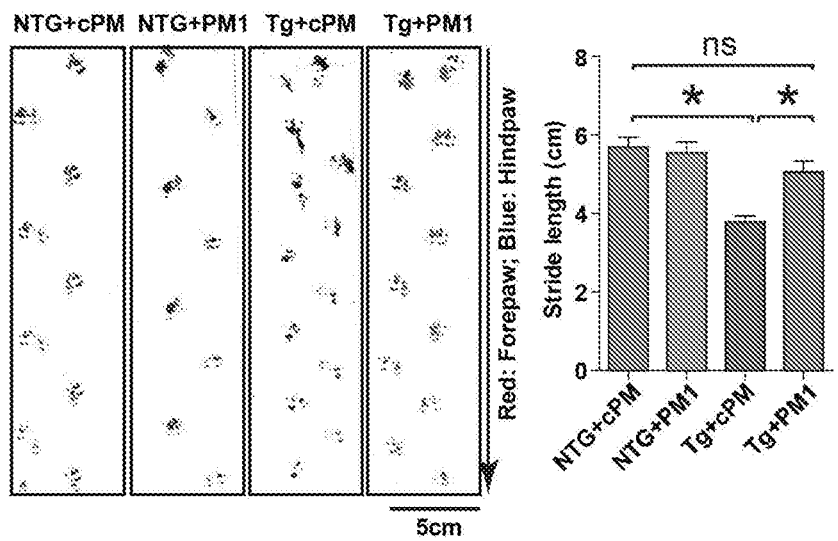
Figs. 6H-I

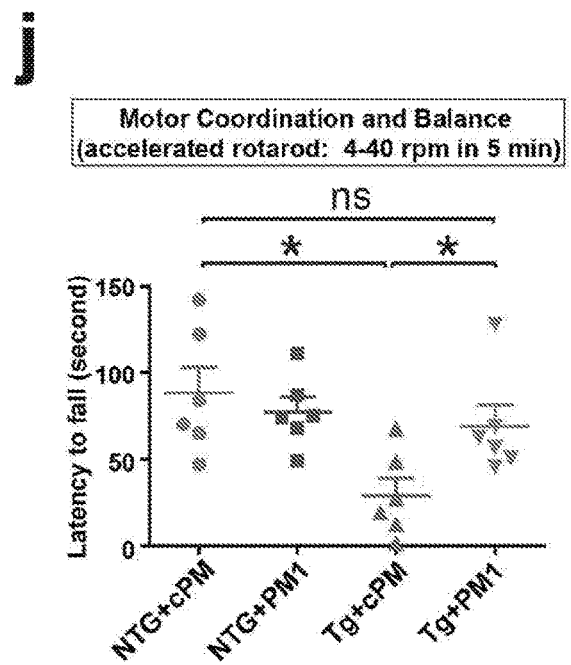
Fig. 6J
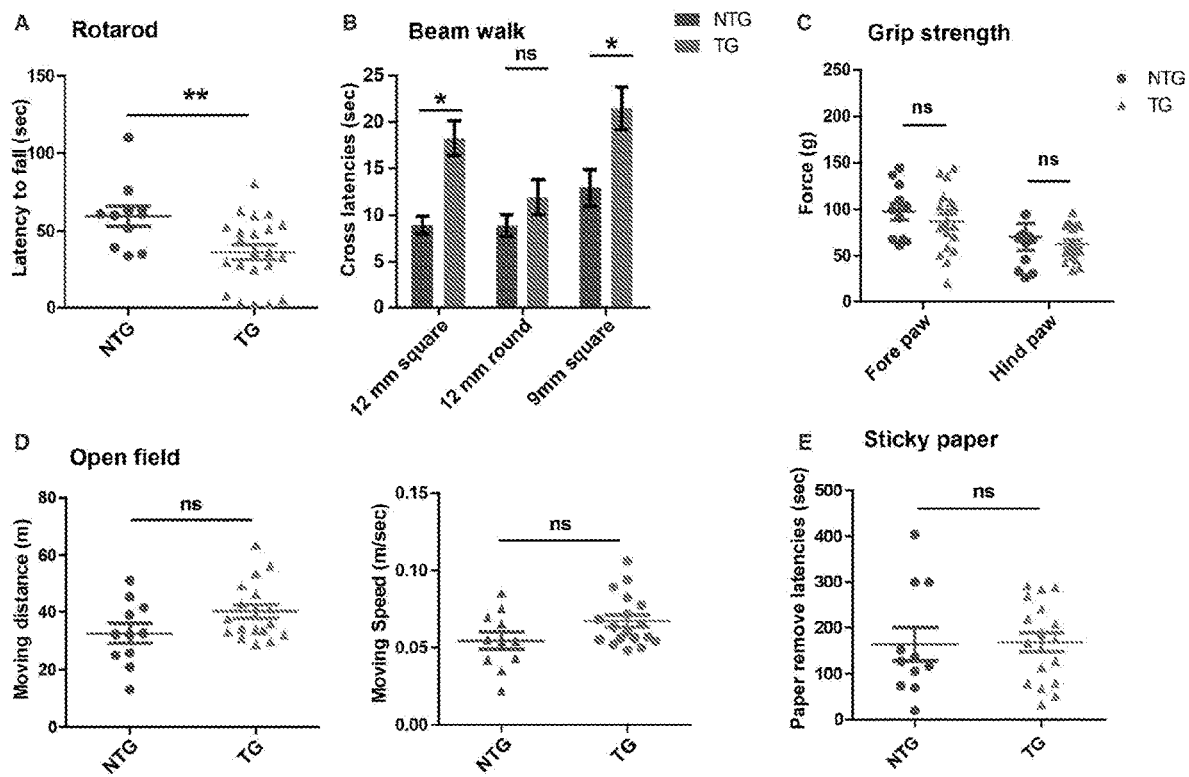
Figs. 7A-E

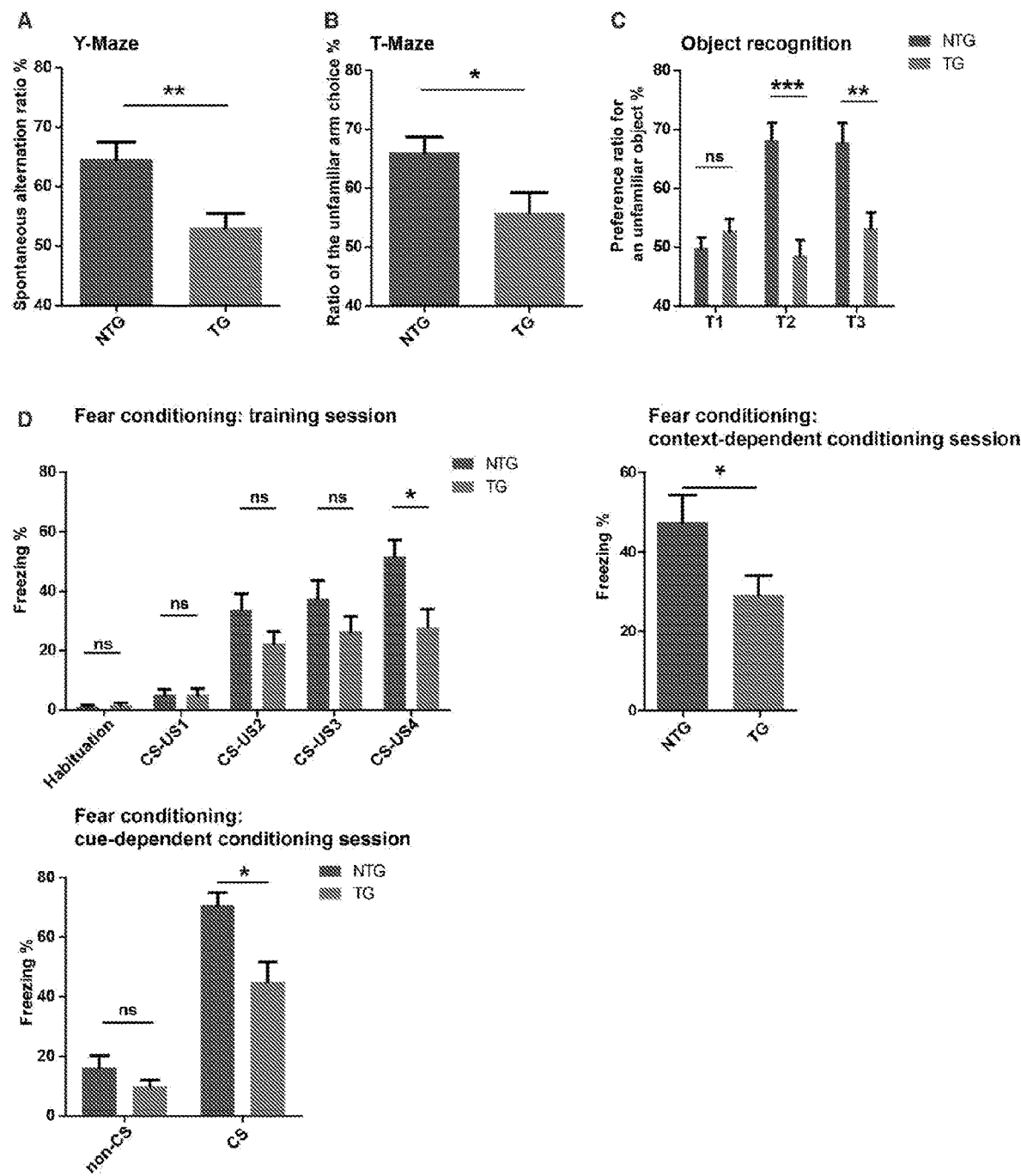
Figs. 8A-D

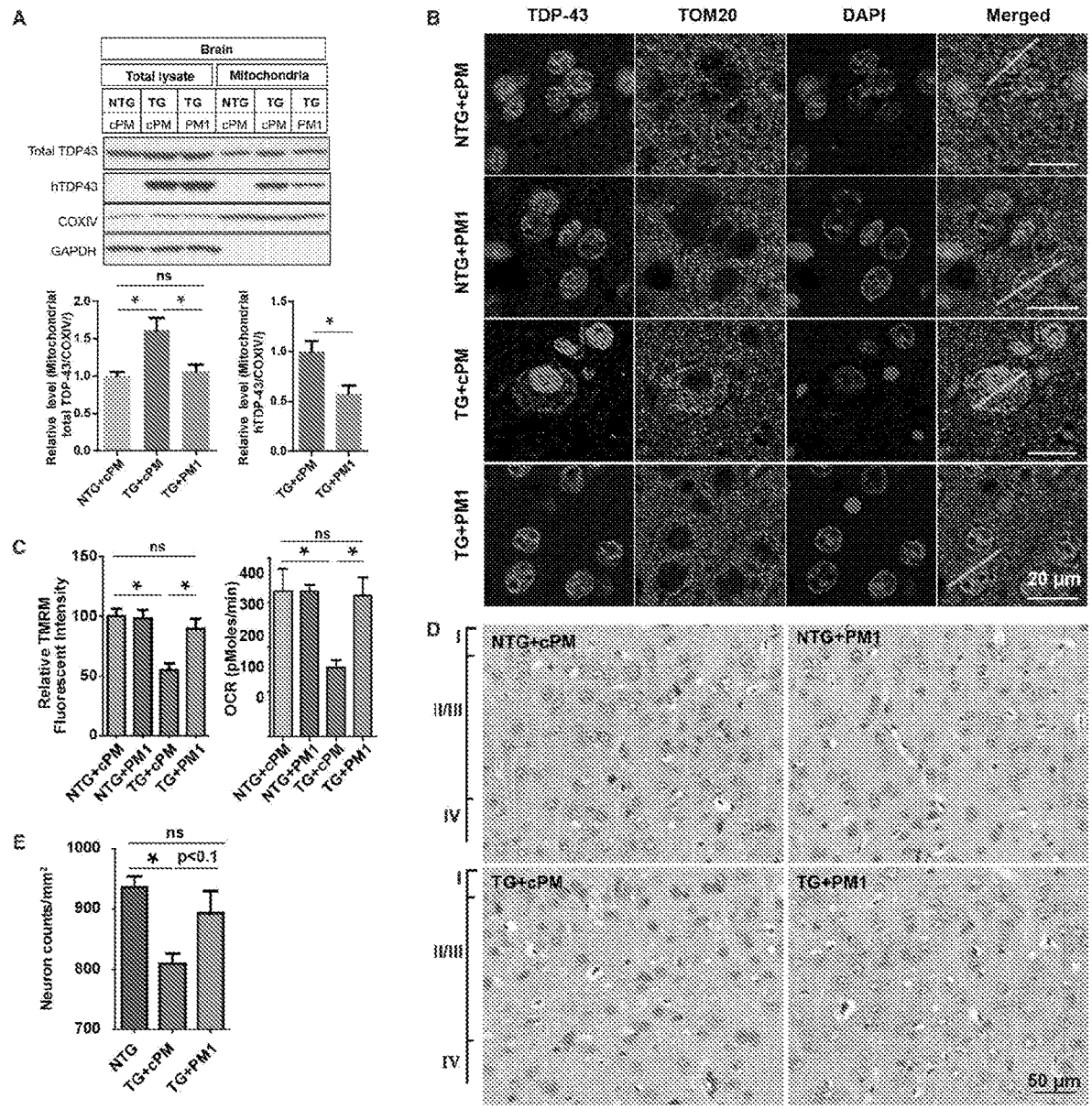
Figs. 9A-E

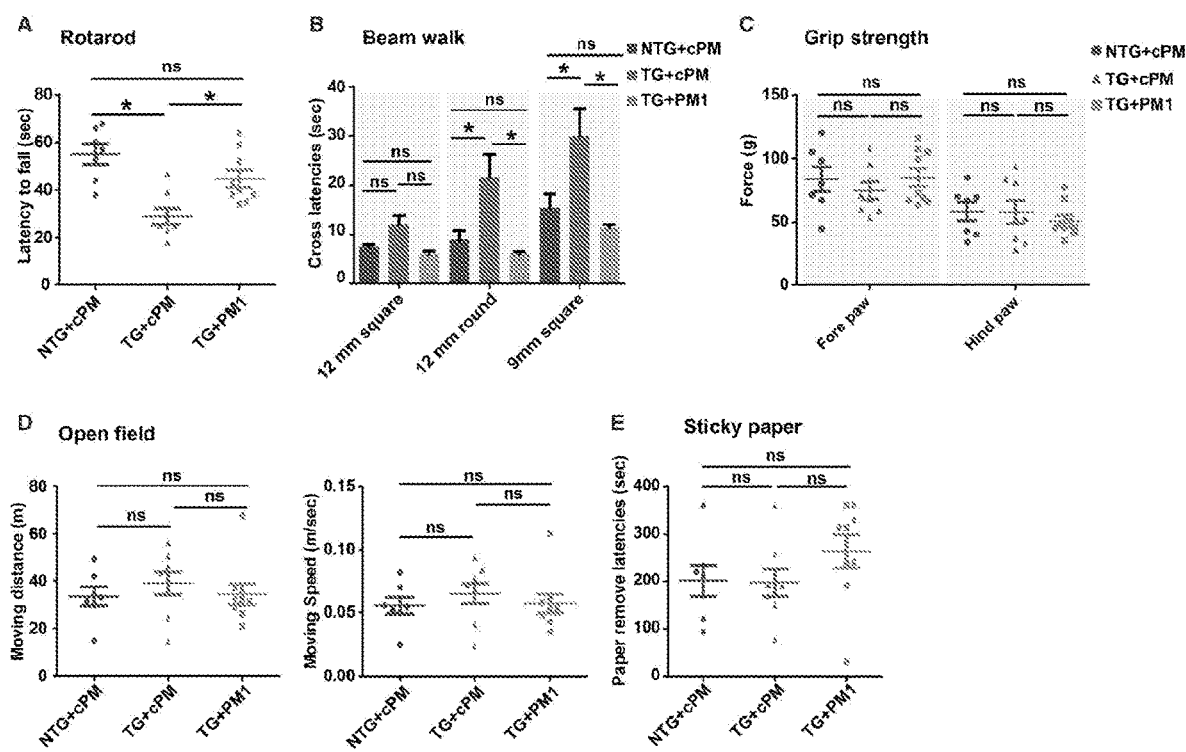
Figs. 10A-E

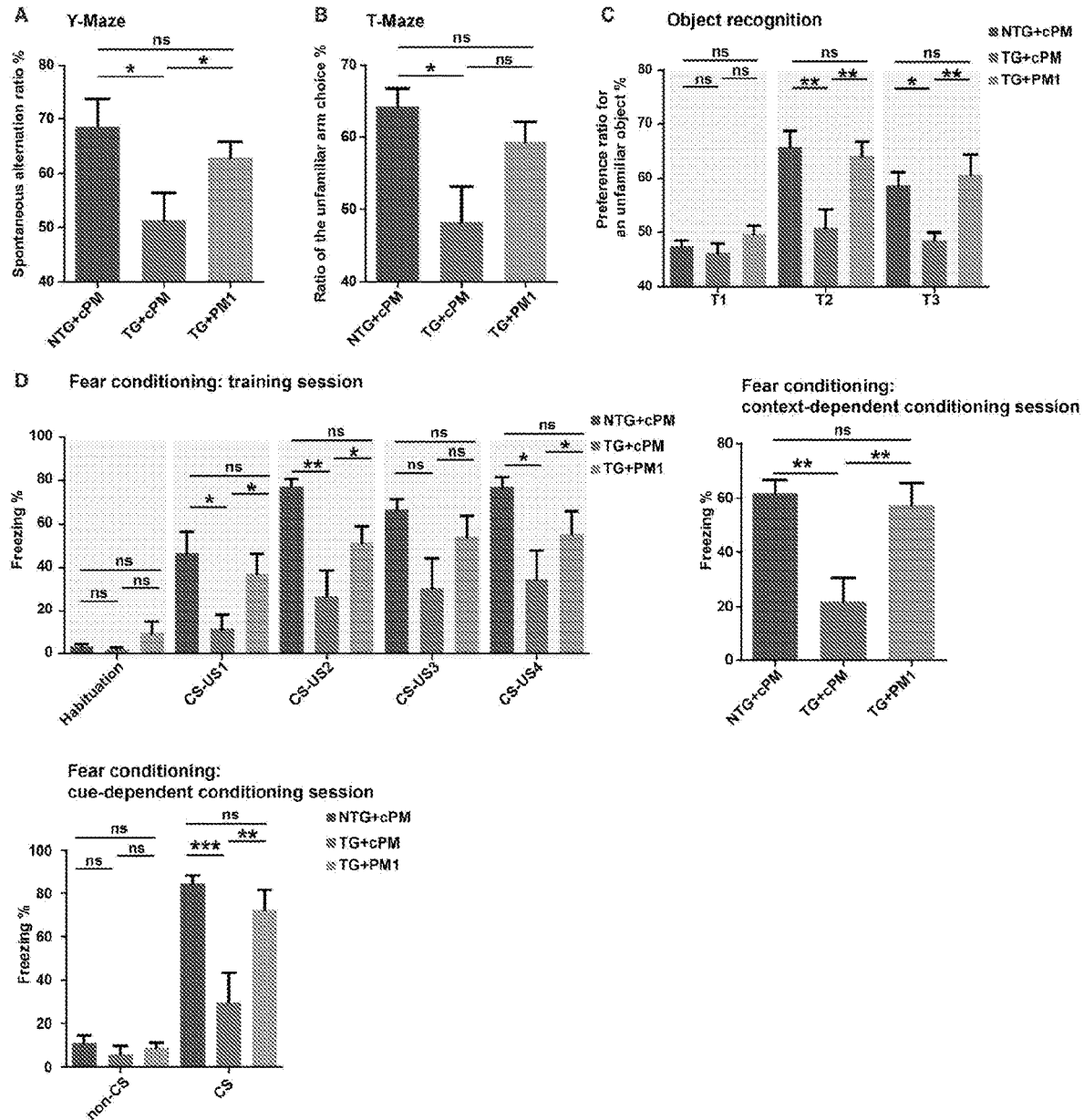
Figs. 11A-D

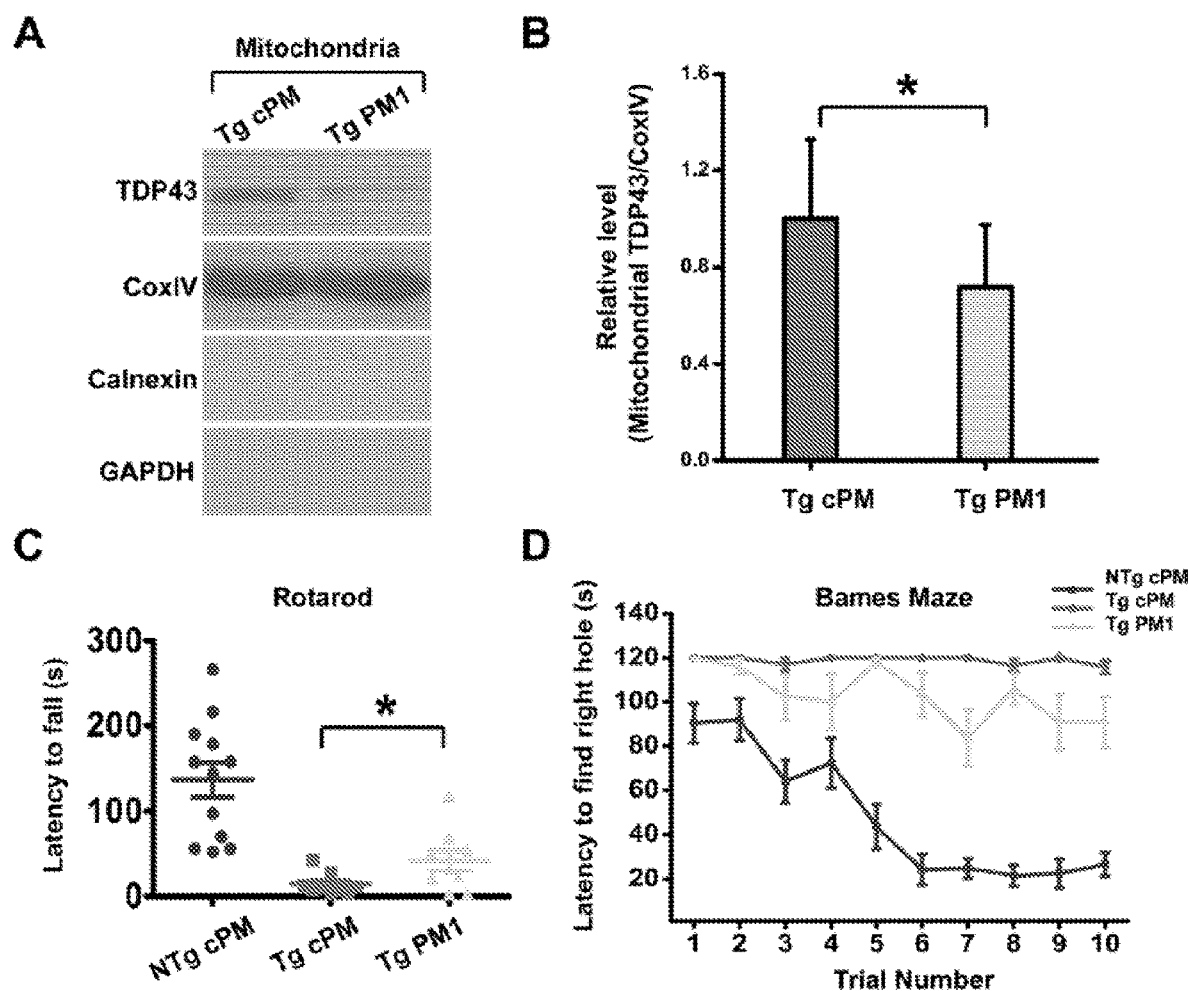
Figs. 12A-D

SEQUENCE LISTING

```
<160> NUMBER OF SEQ ID NOS: 19

<210> SEQ ID NO 1
<211> LENGTH: 7
<212> TYPE: PRT
<213> ORGANISM: Homo sapiens

<400> SEQUENCE: 1

Phe Pro Gly Ala Cys Gly Leu
1               5

<210> SEQ ID NO 2
<211> LENGTH: 8
<212> TYPE: PRT
<213> ORGANISM: Homo sapiens

<400> SEQUENCE: 2

Leu Ile Val Leu Gly Leu Pro Trp
1               5

<210> SEQ ID NO 3
<211> LENGTH: 5
<212> TYPE: PRT
<213> ORGANISM: Homo sapiens

<400> SEQUENCE: 3

Gly Phe Gly Phe Val
1               5

<210> SEQ ID NO 4
<211> LENGTH: 8
<212> TYPE: PRT
<213> ORGANISM: Homo sapiens

<400> SEQUENCE: 4

Ala Phe Ala Phe Val Thr Phe Ala
1               5

<210> SEQ ID NO 5
<211> LENGTH: 7
<212> TYPE: PRT
<213> ORGANISM: Homo sapiens

<400> SEQUENCE: 5

Gly Gly Gly Ala Gly Leu Gly
1               5

<210> SEQ ID NO 6
<211> LENGTH: 7
<212> TYPE: PRT
<213> ORGANISM: Homo sapiens

<400> SEQUENCE: 6

Gly Ala Ala Ile Gly Trp Gly
1               5
```

```
<210> SEQ ID NO 7
<211> LENGTH: 9
<212> TYPE: PRT
<213> ORGANISM: Homo sapiens

<400> SEQUENCE: 7

Ala Gln Phe Pro Gly Ala Cys Gly Leu
1               5

<210> SEQ ID NO 8
<211> LENGTH: 9
<212> TYPE: PRT
<213> ORGANISM: Homo sapiens

<400> SEQUENCE: 8

Ser Lys Gly Phe Gly Phe Val Arg Phe
1               5

<210> SEQ ID NO 9
<211> LENGTH: 9
<212> TYPE: PRT
<213> ORGANISM: Homo sapiens

<400> SEQUENCE: 9

Ser Arg Gly Gly Gly Ala Gly Leu Gly
1               5

<210> SEQ ID NO 10
<211> LENGTH: 414
<212> TYPE: PRT
<213> ORGANISM: Homo sapiens

<400> SEQUENCE: 10

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
                20                  25                  30

Ala Gln Phe Pro Gly Ala Cys Gly Leu Arg Tyr Arg Asn Pro Val Ser
            35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Lys Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Asx Cys Thr Glu Asp Met Thr Glu Asp Glu Leu Arg
        195                 200                 205
```

```
Glu Phe Phe Ser Gln Tyr Gly Asp Val Met Asp Val Phe Ile Pro Lys
    210                 215                 220
Pro Phe Arg Ala Phe Ala Val Thr Phe Ala Asp Asp Gln Ile Ala
225                 230                 235                 240
Gln Ser Leu Cys Gly Glu Asp Glu Ile Ile Lys Gly Ile Ser Val His
                245                 250                 255
Ile Ser Asn Ala Glu Pro Lys His Asn Ser Asn Arg Gln Leu Glu Arg
                260                 265                 270
Ser Gly Arg Phe Gly Gly Asn Pro Gly Gly Phe Cys Asn Gln Gly Gly
            275                 280                 285
Phe Gly Asn Ser Arg Gly Gly Gly Ala Gly Leu Gly Asn Asn Gln Gly
            290                 295                 300
Ser Asn Met Gly Gly Gly Met Asn Phe Gly Ala Phe Ser Ile Asn Pro
305                 310                 315                 320
Ala Met Met Ala Ala Ala Gln Ala Ala Leu Gln Ser Ser Trp Gly Met
                325                 330                 335
Met Gly Met Leu Ala Ser Gln Gln Asn Gln Ser Gly Pro Ser Gly Asn
                340                 345                 350
Asn Gln Asn Gln Gly Asn Met Gln Arg Glu Pro Asn Gln Ala Phe Gly
            355                 360                 365
Ser Gly Asn Asn Ser Tyr Ser Gly Ser Asn Ser Gly Ala Ala Ile Gly
            370                 375                 380
Trp Gly Ser Ala Ser Asn Ala Gly Ser Gly Ser Gly Phe Asn Gly Gly
385                 390                 395                 400
Phe Gly Ser Ser Met Asp Ser Lys Ser Ser Gly Trp Gly Met
                405                 410

<210> SEQ ID NO 11
<211> LENGTH: 11
<212> TYPE: PRT
<213> ORGANISM: Homo sapiens

<400> SEQUENCE: 11

Tyr Gly Arg Lys Lys Arg Arg Gln Arg Arg Arg
1               5                   10

<210> SEQ ID NO 12
<211> LENGTH: 20
<212> TYPE: PRT
<213> ORGANISM: Homo sapiens

<400> SEQUENCE: 12

Tyr Gly Arg Lys Lys Arg Arg Gln Arg Arg Ser Lys Gly Phe Gly
1               5                   10                  15
Phe Val Arg Phe
        20

<210> SEQ ID NO 13
<211> LENGTH: 16
<212> TYPE: PRT
<213> ORGANISM: Homo sapiens

<400> SEQUENCE: 13

Tyr Gly Arg Lys Lys Arg Arg Gln Arg Arg Gly Phe Gly Phe Val
1               5                   10                  15

<210> SEQ ID NO 14
<211> LENGTH: 18
```

```
<212> TYPE: PRT
<213> ORGANISM: Homo sapiens

<400> SEQUENCE: 14

Tyr Gly Arg Lys Lys Arg Arg Gln Arg Arg Gly Gly Gly Ala Gly
1               5                   10                  15

Leu Gly

<210> SEQ ID NO 15
<211> LENGTH: 20
<212> TYPE: PRT
<213> ORGANISM: Homo sapiens

<400> SEQUENCE: 15

Tyr Gly Arg Lys Lys Arg Arg Gln Arg Arg Ala Gln Phe Pro Gly
1               5                   10                  15

Ala Cys Gly Leu
            20

<210> SEQ ID NO 16
<211> LENGTH: 20
<212> TYPE: PRT
<213> ORGANISM: Homo sapiens

<400> SEQUENCE: 16

Tyr Gly Arg Lys Lys Arg Arg Gln Arg Arg Ser Lys Gly Phe Gly
1               5                   10                  15

Phe Val Arg Phe
            20

<210> SEQ ID NO 17
<211> LENGTH: 20
<212> TYPE: PRT
<213> ORGANISM: Homo sapiens

<400> SEQUENCE: 17

Tyr Gly Arg Lys Lys Arg Arg Gln Arg Arg Ser Arg Gly Gly Gly
1               5                   10                  15

Ala Gly Leu Gly
            20

<210> SEQ ID NO 18
<211> LENGTH: 20
<212> TYPE: PRT
<213> ORGANISM: Homo sapiens

<400> SEQUENCE: 18

Tyr Gly Arg Lys Lys Arg Arg Gln Arg Arg Ala Ala Gln Gly Phe
1               5                   10                  15

Gly Cys Pro Leu
            20

<210> SEQ ID NO 19
<211> LENGTH: 19
<212> TYPE: PRT
<213> ORGANISM: Homo sapiens

<400> SEQUENCE: 19

Tyr Gly Arg Lys Lys Arg Arg Gln Arg Arg Gly Arg Phe Phe Lys
1               5                   10                  15

Ser Phe Gly
```

TDP-43 MITOCHONDRIAL LOCALIZATION INHIBITOR FOR THE TREATMENT OF NEUROGENERATIVE DISEASE

RELATED APPLICATION

This application claims Priority from U.S. Provisional Application No. 62/328,484, filed Apr. 27, 2016 and 62/319,580 filed Apr. 7, 2016, the subject matter of which are incorporated herein by reference in their entirety.

GOVERNMENT FUNDING

This invention was made with Government Support under Grant No. 1R01NS089604 awarded by the national institutes of health. The United States Government has certain rights in the invention.

BACKGROUND

Amyotrophic lateral sclerosis (ALS) is the most common motor disease characterized by progressive motor neuron degeneration in the brain stem and spinal cord, while frontotemporal dementia (FTD) is the second most common form of early-onset dementia caused by neuron loss in the frontal and temporal cortex. The vast majority of ALS or FTD cases, referred to as sporadic ALS or FTD, are not genetically transmitted and their causes remain unknown. Currently, there is no effective treatment for both ALS and FTD.

TDP-43 is a small ubiquitously expressed RNA/DNA binding protein containing two tandem RNA recognition motifs RRM1 and RRM23. Previous studies have revealed that TDP-43 primarily binds mRNA, and regulates post-transcriptional RNA processing including RNA splicing, transportation and translation. Autosomal dominant mutations in TDP-43 are associated with sporadic and familial ALS, and the redistribution of TDP-43 from the nucleus to cytoplasm has been recognized as a pathological hallmark for most forms of ALS and most frequent subtypes of FTD. In fact, the mis-localization of TDP-43 to the cytoplasm also represents a key pathological feature of other major neurodegenerative diseases including Alzheimer's disease, Parkinson's disease and Huntington's disease.

SUMMARY

Embodiments described herein generally relate to compositions and methods of inhibiting TAR DNA Binding Protein 43 (TDP-43) mitochondrial localization in a neural cell and particularly relates to compositions and methods for treating neurodegenerative diseases or disorders in a subject in need thereof. The methods can include administering to a neural cell or the subject in need thereof a therapeutically effective amount of an agent that inhibits TDP-43 mitochondrial localization.

In some embodiments, the neurodegenerative disease or disorder can include neurodegenerative diseases or disorders characterized and/or associated with aberrant TDP-43 mitochondrial localization, TDP-43 neuronal toxicity, and/or mutations of TDP-43. The neurodegenerative disease can include, for example, amyotrophic lateral sclerosis (ALS), frontotemporal dementia (FTD), Alzheimer's disease, dementias related to Alzheimer's disease, Parkinson's, senile dementia, Huntington's disease, Gilles de Ia Tourette's syndrome, multiple sclerosis, or hereditary motor and sensory neuropathy.

Other embodiments relate to methods of treating motor-coordinative and cognitive dysfunction associated with mutant TDP-43 expression. The methods can include administering to a neural cell or the subject in need thereof a therapeutically effective amount of an agent that inhibits TDP-43 mitochondrial localization.

In some embodiments, the agent or TDP-43 mitochondrial localization inhibitor includes a therapeutic peptide of about 5 to about 10 amino acids having an amino acid sequence that is at least about 70%, at least about 75%, at least about 80%, at least about 85%, at least about 90%, or at least about 95% identical to about 5 to about 8 consecutive amino acids of a mitochondrial internal targeting signal of TDP-43. For example, the therapeutic peptide can include an amino acid sequence that is at least about 70%, at least about 75%, at least about 80%, at least about 85%, at least about 90%, or at least about 95% identical to about 5 to about 7 consecutive amino acids of M1 (SEQ ID NO: 1), M3 (SEQ ID NO: 3), or M5 (SEQ ID NO: 5) or TDP-43. In some embodiments, the therapeutic peptide can include, consist essentially of, or consist of a peptide having an amino acid sequence of SEQ ID NO: 1 or SEQ ID NO: 7.

In other embodiments, the agent includes a transport moiety that is linked to the therapeutic peptide and facilitates uptake of the therapeutic peptides by the cell. For example, the transport moiety can be an HIV Tat transport moiety.

In still other embodiments, the cell is in a subject being treated, and the therapeutic agent is administered locally or systemically to the subject being treated.

In yet other embodiments, the therapeutic peptide is expressed in the neural cell.

BRIEF DESCRIPTION OF THE DRAWINGS

FIGS. 1(A-I) illustrate that TDP-43 co-localizes with and accumulates in mitochondria in ALS and FTD patients. (A, B) Representative confocal images and line-scan analysis of Tom20 and TDP-43 in human motor neurons in lumbar spinal cords of age-matched normal individuals (n=5) and sporadic ALS cases (n=6) (A), or human cortical neurons in cortices of age-matched normal individuals (n=3) and sporadic FTD cases (n=4) (B). Neurons were co-stained using specific antibodies against Tom20 and TDP-43 respectively. Representative line-scan analysis of the co-localization between Tom20 and TDP-43 in white solid lines with "2" width in a, b are shown in right panels. The line-scan analysis was performed by Image J RGB Profile Plot plugin as described in detail in methods. (c, d) Representative reconstructed three-dimension (3D) images of neurons in a and b respectively using series thin confocal images (around 30 continuous images with 200 nm optical thickness) by Image J RGB 3D Viewer plugin. (E, F) Representative immunoblot and quantification of TDP-43 levels in purified mitochondria ("Mitochondria") isolated from age matched control (n=6) and sporadic ALS (n=8) spinal cords (E), or age matched control (n=6) and sporadic FTD (n=7) cortices (F). Compared with controls, TDP-43 in the total tissue lysate ("Total lysate"), i.e., "total TDP-43", remains unchanged in ALS or FTD tissues. Compartment specific markers for cytosol (GAPDH), mitochondria (COXIV and Tom20) and ER (Calnexin) are included. Mitochondrial and total TDP-43 levels are all adjusted by COXIV and GAPDH respectively. (G, H) Representative immunoblot of TDP-43 in different sub-mitochondrial fractions prepared from mitochondria of age matched control and ALS spinal cords (G) and age matched control and FTD cortices (H). Sub-mitochondrial compartment markers include Tom20 for OMM, cytochrome c (Cyto c) for IMS, Tim23 for IMM and Hsp60 for matrix. (I) Representative immuno-electron microscopic (immuno-EM) micrographs of TDP-43 in purified mitochondria isolated from age matched control and sporadic ALS spinal cord, or age matched control and sporadic FTD cortex. Quantification in the right panel shows the average number of TDP-43 gold particles per square μm of mitochondria in thin EM sections (50 nm thickness). Arrowheads point to immunogold labeled TDP-43. Equal amount of 10 μg proteins were loaded in all immunoblots. Data are means±s.e.m of triplicate independent experiments. Statistics: one-way analysis of variance (ANOVA) followed by Tukey's multiple comparison test. *P<0.05, P<0.01 and *P<0.01.

FIGS. 2(A-H) illustrate that ALS-associated genetic mutations in TDP-43 increase its import into mitochondria. (A-C) Representative immunoblot and quantification of TDP-43 in purified mitochondria ("Mitochondria" fraction) isolated from 2 lines of primary human fibroblasts derived from ALS patients bearing TDP-43 G298S or A382T (G298S or A382T fibroblasts) and 4 lines of age matched primary normal human fibroblasts (NHF1-4) (A), HEK293 cells expressing Flag tagged human WT and mutant TDP-43 G298S, A315T or A382T using a pan TDP-43 antibody (B), or spinal cords and brains of 1-2 month old transgenic male mice expressing human WT (n=6) or mutant TDP-43 A315T (n=6) using an antibody specific to human TDP-43 (hTDP-43) (C). HEK293 cells were transiently transfected with constructs expressing indicated Flag tagged TDP-43. Two days after transfection, cells were collected for mitochondrial isolation and further biochemical analysis. Asterisk denotes endogenous TDP-43 while arrowhead indicates exogenous Flag tagged TDP-43. The immunoblots of TDP43 and compartment specific markers in total cell lysate ("Total lysate") are also shown. For quantification, mitochondrial TDP-43 is adjusted by both total TDP-43 (i.e., expression of TDP-43 in total cell lysate) and COXIV (expression of COXIV in mitochondrial fraction). (D, E) Representative immunoblot of TDP-43 in sub-mitochondrial fractions prepared from purified mitochondria of human fibroblasts (D) or spinal cord/brain tissues of transgenic mice (E) expressing WT or mutant human TDP-43. (F) Representative immunoblot of Flag tagged human rTDP-43 (left panel) or biotinylated F1β (right panel) in freshly isolated mitochondria from mouse brain treated with/without 0.25% trypsin or 1148 0.25% trypsin/digitonin (5 mg/10 mg mitochondria) after mitochondrial import assay. (G) Representative immunoblot and quantification of Flag tagged WT and mutant human rTDP-43 in freshly isolated mitochondria from mouse brain after incubation with rTDP-43 at indicated times followed by 0.25% trypsin/digitonin (5 mg/10 mg mitochondria) post-import treatment. Note: Flag tag at either N- or C terminus of WT/mutant TDP-43 has no significant effect on its import (data not shown). (H) Representative immuno-EM analysis of Flag tagged human rTDP-43 WT or A315T in purified mouse brain mitochondria after mitochondrial import assay (no post-import treatment). Quantification shows the average number of TDP-43 gold particles per square μm of mitochondria in thin EM sections (50 nm thickness). Arrowheads point to immunogold labeled TDP-43. Equal amount of proteins (10 μg) were loaded in all immunoblot analyses. Data are means±s.e.m of triplicate experiments. Statistics: one-way analysis of variance (ANOVA) followed by Tukey's multiple comparison test. *P<0.05, *P<0.001 and **P<0.0001. In panel g, *P<0.05, *P<0.05, compared with WT TDP-43.

FIGS. 6(A-J) illustrate that protection from TDP-43 toxicity on mitochondria and motor neurons by the inhibition of TDP-43 mitochondrial localization in vivo. (A) Schematic and representative large field image showing bicistronic lentiviral transduction and mitochondrial labeling by mitoDsRed2 in vivo. 3 month old mice were injected with 2 μl 1×10$^9$ TU/ml bicistronic lentivirus encoding both TDP-43 and mitoDsRed2 into the motor cortex and scarified 7 days later. Arrow points the injection site. AP/Anterior-Posterior: 1 mm; ML/Medial-Lateral: 1 mm and DV/Dorsal-Ventral: 0.7 mm (B) Representative 2D/3D (enlargements) confocal images and quantification of mitochondrial length in neurons infected with bicistronic lentivirus encoding mitoDsRed2 and indicated TDP-43 WT and A315T under the neuronal specific mouse synapsin1 gene promoter. Upper panels are large field images and bottom panels are enlargements of mitochondria in neurites. n=45, 50, 40, 33 and 35 for vector, WT, WT/ΔM1, A315T and A315T/ΔM1 expressing neurons respectively from 6 3-month-old mice per group. (C) Representative immunostaining and quantification of cleaved caspase 3 positive neurons in the motor cortex. Nuclei are stained by DAPI and positively infected neurons are identified by mitoDsRed2. n=35, 37, 33, 33 and 32 for vector, WT, WT/ΔM1, A315T and A315T/ΔM1, expressing neurons respectively from 6 3-month-old mice per group. (D) Representative immunoblot and quantification of the expression of mitochondrial encoded proteins in isolated mitochondria from spinal cords of 70 day old non-transgenic (NTG) and transgenic mice expressing TDP-43 A315T (Tg) that were treated with indicated peptide (n=6 mice/group, all male, cPM: scrambled M1). (E, F) Measurement of OCR/$m\Delta_\psi$ (E) and OXPHOS complex assembly (F) in synaptic mitochondria in 70 day old non-transgenic (NTG) and transgenic mice expressing TDP-43 A315T that were treated with indicated peptide (n=4 mice/group, all male). Synaptosomes were isolated from mouse brains (Synaptosomes from spinal cord tissues were not sufficient for further mitochondrial purification and the measurement of OXPHOS complex assembly) and attached to seahorse XF24 microplates or 24 well cell culture plates. OCR of synaptic mitochondria in synaptosomes were determined directly by seahorse, while $m\Delta_\psi$ was measured by a fluorescence microplate reader after 20 nM TMRM loading for 30 minutes. The assembly of OXPHOS complexes was determined using isolated mitochondria from synaptosomes by BN-PAGE/immunoblot using indicated specific antibodies against subunits of each OXPHOS complex. (G) Motor neuron counts in lumbar spinal cords of 70 day old mice treated with indicated peptide (n=6 mice/group, all male). (H) Representative confocal images and quantification of neuromuscular junctions (NMJs) in gastrocnemius muscles (the largest muscle in the calf of leg). SV2 (synaptic vesicle protein 2, presynaptic marker) and (2H3, specific antibody against neurofilament); α-bungarotoxin stains postsynaptic marker nicotinic acetylcholine receptor (AChR). n=6 mice/group, all male. (I) Representative images and quantification of walking footprint patterns of 70 day old mice treated with indicated peptides (n=6 mice/group, male). Arrow points the walking direction. (J) Motor coordination and balance of 70 day old mice on an accelerating rotarod (4-40 rpm in 5 minutes) treated with indicated peptides (n=6 mice/group, all male). For D-J, all treatments began from 60 day old. Data are means±s.e.m of triplicate experiments. Statistics: one-way analysis of variance (ANOVA) followed by Tukey's multiple comparison test. *$P<0.05$, $P<0.01$ and *$P<0.001$.

FIGS. 7(A-E) illustrate sensorimotor performances of adult hemizygous TDP-43M337V mice. (A) Motor coordination and balance in NTG and hemizygous TDP-43M337V mice on the rotarod, manifested as the maximum time that mice could remain on the accelerating rotating rod. (B) Motor coordination and balance of mice in NTG and hemizygous TDP-43M337V mice assessed by the latency to traverse each beam. (C) Fore- and hind-limb strength of NTG and hemizygous TDP-43M337V mice. (D) The distance traveled (m) and velocity (m/second) of non-transgenic age matched littermate controls (NTG) and transgenic (TG) hemizygous TDP-43M337V mice recoded continually for 10 minutes in the open field test. (E) Sensorimotor responses of NTG and hemizygous TDP-43M337V mice measured by the latency to remove a piece of adhesive tape from its hindpaw. All mice are at 8-9 month old. n=11 for NTG (8 male/3 female) and 18 for TG (10 male/8 female). Data in the beam walking test analyzed using two way ANOVA analysis followed by Bonferroni multiple comparisons, while data in other tests analyzed using student-t-test. All data presented as dots and means±SEM; *$p<0.05$, **$p<0.01$; ns: nonsignificant.

FIGS. 8(A-D) illustrate cognitive performances of adult hemizygous TDP-43M337V mice. (A, B) Spontaneous alternation of NTG and hemizygous TDP-43M337V mice in the Y maze (A) and novelty preference in T maze (B) test. (C) Preference ratio for an unfamiliar object of NTG and hemizygous TDP-43M337V mice in the 3 different sessions in the object recognition test. T1: first 5-minute trail session; T2: 1.5 hour delayed 5-minute dissimilar stimuli session; T3: 24 hour delayed 5-minute third session. (D) Freezing behavior of NTG and hemizygous TDP-43M337V mice in the trail sessions (habituation without stimulus and repeated four times with inter-stimulus-interval), contextual fear learning and cue-dependent fear learning in the fear conditioning test. CS: conditional stimulus (white noise, 80 dB for 30 s); US: unconditional stimulus (an electrical shock of 0.5 mA for 1 s). All mice are at 8-9 month old. n=11 for NTG (8 male/3 female) and 18 for TG (10 male/8 female). Data analyzed using student-t-test or twoway ANOVA followed by Bonferroni multiple comparisons. All data presented as dots and means±SEM; *$p<0.05$, $p<0.01$, *$p<0.001$; ns: non-significant.

FIGS. 9(A-E) illustrate inhibition of TDP-43 mitochondrial localization, mitochondrial dysfunction and neuronal loss in brains of hemizygous TDP-43$^{M337V}$ mice by PM1. 11 month old NTG and hemizygous TDP-43M337V mice were treated with 1.5 mg/kg/day cPM (control peptide for PM1) or PM1 continuously for 6 weeks by subcutaneous infusion. NTG+cPM: NTG mice treated with cPM; NTG+PM1: NTG mice treated with PM1; TG+cPM: hemizygous TDP-43M337V mice treated with cPM; TG+PM1: hemizygous TDP-43M337V mice treated with PM1. (A) Representative immunoblot and quantification of exogenous human TDP-43 or total TDP-43 in total lysates and purified mitochondrial fraction of brains of NTG and TG mice treated with cPM or PM1 peptide. Equal amount of 10 μg proteins were loaded. Data are means±SEM of triplicate experiments. (B) Representative confocal images of Tom20 and TDP-43 in cortical neurons co-stained using specific antibodies against Tom20 and TDP-43 respectively. Line-scan analysis of the co-localization between Tom20 and TDP-43 in white solid lines by Image J RGB Profile Plot plugin. (C) Measurement of OCR/m$\Delta_\psi$ in synaptic mitochondria in NTG and TG mice that were treated with indicated peptide (n=4 mice/group). Synaptosomes were isolated from mouse brains attached to seahorse XF24 microplates or 24 well cell culture plates. OCR of synaptic mitochondria in synaptosomes were determined directly by seahorse, while m$\Delta_\psi$ was measured by a fluorescence microplate reader after 20 nM TMRM loading for 30 minutes. (D, E) Representative hematoxylin and eosin (H&E) stained sections and quantification showing reduced neuronal density in mouse cortex 20 layer 2&3 of TG mice with cPM (Tg mice without cPM treatment showing similar patterns, not shown). In contrast, TG mice treated with PM1 show comparable neuronal density and morphology, similar to NTG mice or NTG mice treated by cPM1 or PM1. All mice at 12-13 month old. n=5 for NTG, 4 for TG+cPM and 3 for TG+PM1. Data analyzed using two-way ANOVA followed by Bonferroni multiple comparisons. *$p<0.05$; ns: non-significant.

FIGS. 10(A-E) illustrate improved motor coordination performances of adult hemizygous TDP-43M337V mice by PM1. 11 month old NTG and hemizygous TDP-43M337V mice were treated with 1.5 mg/kg/day cPM (control peptide for PM1) or PM1 continuously for 6 weeks by subcutaneous infusion. NTG+cPM: NTG mice treated with cPM; TG+cPM: hemizygous TDP-43M337V mice treated with cPM; TG+PM1: hemizygous TDP-43M337V mice treated with PM1. (A-E) Sensorimotor performances of NTG+cPM, TG+cPM and TG+PM1 mice in the rotarod (A), beam walking (B), fore/hind-limb strength (C), open field (D), and sticky paper test (E). All mice are at 12-13 month old. n=7 for NTG+cPM (4 male/3 female), 8 for TG+cPM (4 male/4 female) and 9 for TG+PM1 (5 male/4 female). Data analyzed using ANOVA followed by Bonferroni multiple comparisons. All data presented as dots and means±SEM; *$p<0.05$; ns: non-significant.

FIGS. 11(A-D) illustrate improved cognitive performances of adult hemizygous TDP-43$^{M337V}$ mice by PM1. 11 month old NTG and hemizygous TDP-43$^{M337V}$ mice were treated with 1.5 mg/kg/day cPM (control peptide for PM1) or PM1 continuously for 6 weeks by subcutaneous infusion. NTG+cPM: NTG mice treated with cPM; TG+cPM: hemizygous TDP-43M337V mice treated with cPM; TG+PM1: hemizygous TDP-43M337V mice treated with PM1. (A-D) Cognitive performances of NTG+cPM, TG+cPM and TG+PM1 mice in the Y maze (A), T maze (B), object recognition (C) and fear conditioning test (D). All mice are at 12-13 month old. n=7 for NTG+cPM (4 male/3 female), 8 for TG+cPM (4 male/4 female) and 9 for TG+PM1 (5 male/4 female). Data analyzed using ANOVA followed by Bonferroni multiple comparisons. All data presented as dots and means±SEM; *$p<0.05$, $p<0.01$, *$p<0.001$; ns: non-significant.

FIGS. 12(A-D) illustrate inhibition of TDP-43 mitochondrial localization improved motor coordination and cognitive performances of 5×FAD transgenic mice. 10-month-old NTg and Tg female mice were treated with 0.5 mg/kg/day cPM (control peptide for PM1) or PM1 continuously for 4 weeks by subcutaneous infusion. NTg+cPM, NTg mice treated with cPM; Tg+cPM, 5×FAD mice treated with cPM; Tg+PM1, 5×FAD mice treated with PM1. (A, B) Representative immunoblot (A) and quantification (B) of endogenous TDP-43 in purified mitochondrial fraction of brains of Tg mice treated with cPM or PM1 peptide. Equal amounts of 10 μg of proteins were loaded. (B). (C) Performance of NTg+cPM, Tg+cPM, and Tg+PM1 mice in the rotarod. (D) Performance of NTg+cPM, Tg+cPM, and Tg+PM1 mice in the Barnes maze task. All female mice were 10 months old. n=11 for NTg+cPM, 9 for Tg+cPM, and 9 for Tg+PM1. Data are shown as the mean±SEM. *p<0.05.

DETAILED DESCRIPTION

Figure 3G:
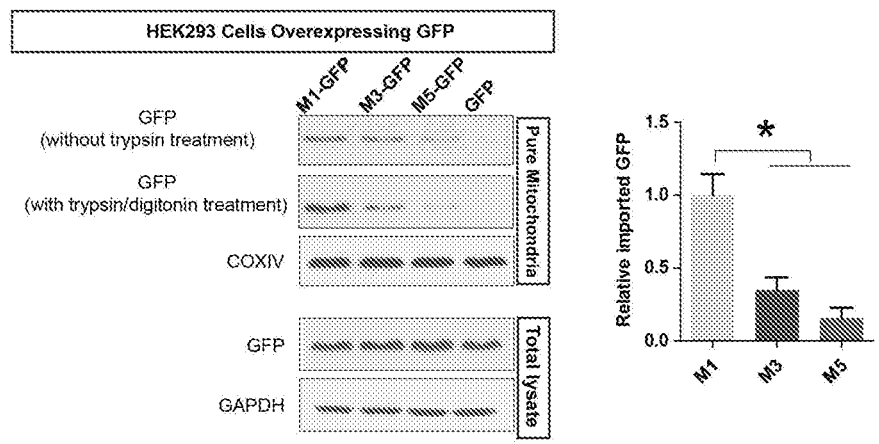
FIGS. 3(A-G) illustrates that TDP-43 mitochondrial import/localization depends on TOM/TIM23 complex and internal M1/3/5 motifs. (A) The structure (top panel) and the amino acid sequence (bottom panel) (SEQ ID NO: 10) of human TDP-43. RRM1/2 are RNA recognition motifs. NLS: nuclear localization sequence; NES: nuclear export sequence. (B) Representative immunoblot and quantification of rTDP-43 in freshly isolated mitochondria from mouse brain (indicated by "Brain Mitochondria") after incubation with indicated recombinant Flag tagged human wild type (WT) TDP-43 or artificial TDP-43 mutants with deletions of putative internal targeting signals (ΔM1-6) followed by 0.25% trypsin/digitonin (5 mg/10 mg mitochondria) treatment (mitochondrial import assay in vitro). (C) Representative immunoblot and quantification of TDP-43 in isolated pure mitochondria from HEK293 overexpressing Flag tagged TDP-43 (ΔM1-6) using specific antibody against Flag. Expression of TDP-43 in cytosolic fraction ("Cytosol"), nuclear fraction ("Nuclear") and total lysate ("Total") are also shown. HEK293 cells were also transiently transfected with indicated constructs and were subjected to mitochondrial isolation two days after transfection. (D) Representative immunoblot and quantification of Flag tagged rTDP-43 and pF1β in mitochondria that were pre-/co-treated with 5 μM control peptide (cPM), PM1 or PM3, followed by mitochondrial import assay in vitro using rTDP-43 or pF1β incubation. (E, F) Representative immunoblot and quantification of TDP-43 in isolated pure mitochondria from HEK293 cells (E) or rat primary cortical neurons (12 days in vitro: DIV 12, treated with 1 μM cPM, PM1 or PM3 for 24 hours. The immunoblots of TDP43 and compartment specific markers in total cell lysate ("Total") are also shown. (G) Representative immunoblot and quantification of GFP in isolated pure mitochondria from HEK293 cells expressing GFP or M1/3/5-GFP (N-terminus tag). HEK293 cells were collected two days after transient transfection with indicated constructs. Quantification is based on samples co-treated with trypsin/digitonin. The immunoblots of GFP and M1/3/5 tagged GFP in total cell lysate ("Total lysate") are also shown. Equal amount of 10 μg proteins were loaded in all immunoblots. Data are means±s.e.m of triplicate experiments. Statistics: one-way analysis of variance (ANOVA) followed by Tukey's multiple comparison test. *P<0.05.

The embodiments described herein are not limited to the particular methodology, protocols, and reagents, etc., and as such may vary. The terminology used herein is for the purpose of describing particular embodiments only, and is not intended to limit the scope of the present invention, which is defined solely by the claims. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

The articles "a" and "an" are used herein to refer to one or to more than one (i.e., to at least one) of the grammatical object of the article. By way of example, "an element" means one element or more than one element.

As used herein, "one or more of a, b, and c" means a, b, c, ab, ac, bc, or abc. The use of "or" herein can be inclusive or exclusive.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The terms "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

The term "administering" to a patient includes dispensing, delivering or applying an active agent in a pharmaceutical formulation to a subject by any suitable route for delivery of the active agent to the desired location in the subject (e.g., to thereby contact a desired cell, such as a desired neuron), including administration into the cerebrospinal fluid or across the blood-brain barrier, delivery by either the parenteral or oral route, intramuscular injection, subcutaneous or intradermal injection, intravenous injection, buccal administration, transdermal delivery and administration by the rectal, colonic, vaginal, intranasal or respiratory tract route. The agents may, for example, be administered to a comatose, anesthetized or paralyzed subject via an intravenous injection or may be administered intravenously to a pregnant subject to inhibit neuron dysfunction in a fetus. Specific routes of administration may include topical application (such as by eyedrops, creams or erodible formulations to be placed under the eyelid, intraocular injection into the aqueous or the vitreous humor, injection into the external layers of the eye, such as via subconjunctival injection or subtenon injection, parenteral administration or via oral routes.

The terms "contacting neurons" or "treating neurons" refers to any mode of agent delivery or "administration," either to cells or to whole organisms, in which the agent is capable of exhibiting its pharmacological effect in neurons. "Contacting neurons" includes both in vivo and in vitro methods of bringing an agent of the invention into proximity with a neuron. Suitable modes of administration can be determined by those skilled in the art and such modes of administration may vary between agents.

The terms an "effective amount" of an agent or therapeutic peptide refers to an amount sufficient to achieve a desired therapeutic or pharmacological effect, such as an amount that is capable of enhancing neuronal viability and/or inhibiting neuronal death. An effective amount of an agent as defined herein may vary according to factors such as the disease state, age, and weight of the subject, and the ability of the agent to elicit a desired response in the subject. Dosage regimens may be adjusted to provide the optimum therapeutic response. An effective amount is also one in which any toxic or detrimental effects of the active agent are outweighed by the therapeutically beneficial effects.

The term a "therapeutically effective amount" refers to an amount effective, at dosages and for periods of time necessary, to achieve the desired therapeutic result. A therapeutic result may be, e.g., lessening of symptoms, prolonged survival, improved mobility, and the like. A therapeutic result need not be a "cure."

The term "expression" refers to the process by which nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

The term "genetic therapy" involves the transfer of heterologous DNA to cells of a mammal, particularly a human, with a disorder or conditions for which therapy or diagnosis is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product; it may encode a product, such as a peptide or RNA that in some manner mediates, directly or indirectly, expression of a therapeutic product. Genetic therapy may also be used to deliver nucleic acid encoding a gene product to replace a defective gene or supplement a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefore, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof.

The term "gene" or "recombinant gene" refers to a nucleic acid comprising an open reading frame encoding a polypeptide, including both exon and (optionally) intron sequences.

The term "heterologous nucleic acid sequence" is typically DNA that encodes RNA and proteins that are not normally produced in vivo by the cell in which it is expressed or that mediates or encodes mediators that alter expression of endogenous DNA by affecting transcription, translation, or other regulatable biochemical processes. A heterologous nucleic acid sequence may also be referred to as foreign DNA. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

The terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

The term "mutant" refers to changes in the genetic material of an organism, in particular a change (i.e., deletion, substitution, addition, or alteration) in a wild type polynucleotide sequence or changes in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

The terms "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The terms "systemic administration," "administered systemically," "peripheral administration" and "administered peripherally" as used herein mean the administration of a compound, drug or other material other than directly into a target tissue (e.g., the central nervous system), such that it enters the animal's system and, thus, is subject to metabolism and other like processes, for example, subcutaneous administration.

The terms "patient" or "subject" or "animal" or "host" refers to any mammal. The subject may be a human, but can also be a mammal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

The terms "polynucleotide sequence" and "nucleotide sequence" are also used interchangeably herein.

The terms "peptide" or "polypeptide" are used interchangeably herein and refer to compounds consisting of from about 2 to about 90 amino acid residues, inclusive, wherein the amino group of one amino acid is linked to the carboxyl group of another amino acid by a peptide bond. A peptide can be, for example, derived or removed from a native protein by enzymatic or chemical cleavage, or can be prepared using conventional peptide synthesis techniques (e.g., solid phase synthesis) or molecular biology techniques (see Sambrook et al., MOLECULAR CLONING: LAB. MANUAL (Cold Spring Harbor Press, Cold Spring Harbor, N.Y., 1989)). A "peptide" can comprise any suitable L- and/or D-amino acid, for example, common a-amino acids (e.g., alanine, glycine, valine), non-a-amino acids (e.g., P-alanine, 4-aminobutyric acid, aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and means for adding or removing protecting groups are known in the art. See, e.g., Green & amp; Wuts, PROTECTING GROUPS IN ORGANIC SYNTHESIS (John Wiley & amp; Sons, 1991). The functional groups of a peptide can also be derivatized (e.g., alkylated) using art-known methods.

Peptides can be synthesized and assembled into libraries comprising a few too many discrete molecular species. Such libraries can be prepared using well-known methods of combinatorial chemistry, and can be screened as described herein or using other suitable methods to determine if the library comprises peptides which can antagonize CSPG-PTPσ interaction. Such peptide antagonists can then be isolated by suitable means.

The term "peptidomimetic", refers to a protein-like molecule designed to mimic a peptide. Peptidomimetics typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. These modifications involve changes to the peptide that do not occur naturally (such as altered backbones and the incorporation of nonnatural amino acids).

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "recombinant," as used herein, means that a protein is derived from a prokaryotic or eukaryotic expression system.

The term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of epithelial cells. The term also covers so-called "leaky" promoters, which regulate expression of a selected nucleic acid primarily in one tissue, but cause expression in other tissues as well. The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., Virology 52:456 (1973); Sambrook et al., Molecular Cloning: A Laboratory Manual (1989); Davis et al., Basic Methods in Molecular Biology (1986); Chu et al., Gene 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

The terms "transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence), which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

The term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as "expression vectors".

The term "wild type" refers to the naturally-occurring polynucleotide sequence encoding a protein, or a portion thereof, or protein sequence, or portion thereof, respectively, as it normally exists in vivo. As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The agents, compounds, compositions, antibodies, etc. used in the methods described herein are considered to be purified and/or isolated prior to their use. Purified materials are typically "substantially pure", meaning that a nucleic acid, polypeptide or fragment thereof, or other molecule has been separated from the components that naturally accompany it. Typically, the polypeptide is substantially pure when it is at least 60%, 70%, 80%, 90%, 95%, or even 99%, by weight, free from the proteins and other organic molecules with which it is associated naturally. For example, a substantially pure polypeptide may be obtained by extraction from a natural source, by expression of a recombinant nucleic acid in a cell that does not normally express that protein, or by chemical synthesis. "Isolated materials" have been removed from their natural location and environment. In the case of an isolated or purified domain or protein fragment, the domain or fragment is substantially free from amino acid sequences that flank the protein in the naturally-occurring sequence. The term "isolated DNA" means DNA has been substantially freed of the genes that flank the given DNA in the naturally occurring genome. Thus, the term "isolated DNA" encompasses, for example, cDNA, cloned genomic DNA, and synthetic DNA.

The terms "portion", "fragment", "variant", "derivative" and "analog", when referring to a polypeptide of the present invention include any polypeptide that retains at least some biological activity referred to herein (e.g., inhibition of an interaction such as binding). Polypeptides as described herein may include portion, fragment, variant, or derivative molecules without limitation, as long as the polypeptide still serves its function. Polypeptides or portions thereof of the present invention may include proteolytic fragments, deletion fragments and in particular, or fragments that more easily reach the site of action when delivered to an animal.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

All percentages and ratios used herein, unless otherwise indicated, are by weight.

Embodiments described herein generally relate to compositions and methods inhibiting TAR DNA Binding Protein 43 (TDP-43) mitochondrial localization in a neural cell and particularly relates to compositions and method for treating neurodegenerative diseases or disorders in a subject in need thereof. It was found that TDP-43 accumulates in mitochondria in neurons of patients with neurodegenerative diseases, such as amyotrophic lateral sclerosis (ALS), frontotemporal dementia (FTD), and Alzheimer's disease. It was further found that neurodegenerative disease-associated mutations of TDP-43 further increase TDP-43 mitochondrial localization in neurons. Within mitochondria, wild-type and mutant TDP-43 bind to mitochondrial transcribed messenger RNAs (mRNAs) encoding OXPHOS respiratory complex 1 subunits ND3 and ND6 and impair their expression, cause complex I disassembly, and neuronal cell death. It was found that suppression of TDP-43 mitochondrial localization in neurons can abolish both wild-type and mutant TDP-43 induced mitochondrial dysfunction and neuronal loss.

Accordingly, some embodiments described herein relate to methods of inhibiting, decreasing, reducing, or suppressiong wild type and/or mutant TDP-43 mitochondrial localization in cells, such as neurons, neural cells, neural progenitor cells, or neural stem cells, and particularly neural cells of a subject having or at risk of a neurodegenerative disease or disorder to treat the neurodegenerative disease or disorder. The methods can include administering to the neural cell of the subject a therapeutically effective amount of an agent that inhibits TDP-43 mitochondrial localization.

In some embodiments, the neurodegenerative disease or disorder can include neurodegenerative diseases or disorders characterized and/or associated with aberrant TDP-43 mitochondrial localization, TDP-43 neuronal toxicity, and/or diseases associated mutations of TDP-43. The neurodegenerative disease can include, for example, amyotrophic lateral sclerosis (ALS), frontotemporal dementia (FTD), Alzheimer's disease, dementias related to Alzheimer's disease, Parkinson's, senile dementia, Huntington's disease, Gilles de la Tourette's syndrome, multiple sclerosis, or hereditary motor and sensory neuropathy.

Other embodiments relate to methods of treating motor-coordinative and cognitive dysfunction associated with mutant TDP-43 expression. The methods can include administering to a neural cell or the subject in need thereof a therapeutically effective amount of an agent that inhibits TDP-43 mitochondrial localization.

In some embodiments, the agent or therapeutic agent that is administered to the cell or subject can be any agent that decreases, inhibits, reduces, and/or suppresses TDP-43 mitochondrial localization in neurons of a subject. A decrease, inhibition, reduction, and/or suppression of TDP-43 mitochondrial localization can include any measurable, reproducible, and/or substantial reduction in: TDP-43 mitochondrial localization; TDP-43 redistribution from the nucleus to cytoplasm; TDP-43 binding to mRNAs encoding mitochondrial respiratory complex 1 subunits ND3 and ND6; TDP-43 mediated disassembly of mitochondrial respiratory complex 1; TDP-43 induced mitochondrial dysfunction and neuron loss; and/or symptoms of diseases mediated by mutant and/or wild-type TDP-43 mitochondrial localization. A substantial reduction is a "reproducible", i.e., consistently observed reduction.

TDP-43 mitochondrial localization in neurons can be decreased, inhibited, reduced, and/or suppressed in several ways including, but not limited to: direct inhibition of the mitochondrial localization of TDP-43 (e.g., by using interfering or inhibiting peptides, dominant negative polypeptides; neutralizing antibodies, small molecules or peptido-mimetics), inhibition of genes and/or proteins that facilitate one or more of, the localization, activity, signaling, and/or function of the TDP-43 (e.g., by decreasing the expression or activity of the genes and/or proteins, such as Tim22 or TOM/Tim22 complexes); activation of genes and/or proteins that inhibit one or more of, the localization, activity, signaling, and/or function of the TDP-43 (e.g., by increasing the expression or activity of the genes and/or proteins); inhibition of genes and/or proteins that are downstream TDP-43 (e.g., by blocking the expression and/or activity of the mediator genes and/or proteins); introduction of genes and/or proteins that negatively regulate one or more of, activity, signaling, and/or function of TDP-43 (e.g., by using recombinant gene expression vectors, recombinant viral vectors or recombinant polypeptides); or gene replacement with, for instance, a hypomorphic mutant of the TDP-43 (e.g., by homologous recombination, overexpression using recombinant gene expression or viral vectors, or mutagenesis).

The therapeutic agent that decreases, inhibits, reduces, or suppresses TDP-43 mitochondrial localization in neurons of a subject can be delivered intracellularly and once delivered intracellularly inhibit TDP-43 induced neuronal toxicity, diseases associated mutations of TDP-43, and/or aberrant TDP-43 mitochondrial localization.

In some embodiments, the therapeutic agent that decreases, inhibits, reduces, or suppresses TDP-43 mitochondrial localization in neurons of a subject includes a therapeutic peptide of about 5 to about 10 amino acids having an amino acid sequence that is at least about 70%, at least about 75%, at least about 80%, at least about 85%, at least about 90%, or at least about 95% identical to about 5 to about 8 consecutive amino acids of a mitochondrial internal targeting signal of TDP-43. Mitochondrial proteins are guided to mitochondria by either cleavable pre-sequences or noncleavable internal signals. It was found that TDP-43 remains uncleaved after import and no cleavable presequence was identified in TDP-43, suggesting TDP-43 uses internal signals. Mitochondrial internal signals are typically composed of a stretch of continuous hydrophobic amino acids, and six such stretches are present in TDP-43 (FIG. 3A, M1-6 (SEQ ID NOs: 1-6)). The deletions of M1/3/5 (ΔM1/3/5) (SEQ ID NOs: 1, 3, and 5) significantly inhibited rTDP-43 import in vitro, and reduced mitochondrial localization of exogenously expressed TDP-43 (FIG. 3B, C). Therapeutic peptides including M1 (SEQ ID NO: 1) and M3 (SEQ ID NO: 3) substantially suppressed rTDP-43 import, and decreased mitochondrial TDP-43 in HEK293 cells and primary neurons (FIG. 3D-F). Advantageously, therapeutic peptides based on identified motifs essential for TDP-43 mitochondrial localization, can specifically suppress WT or mutant TDP-43 mitochondria import without having an effect on the expression of nuclear, cytosolic and total TDP-43.

In some embodiments, the therapeutic peptide can include an amino acid sequence that is at least about 70%, at least about 75%, at least about 80%, at least about 85%, at least about 90%, or at least about 95% identical to about 5 to about 7 consecutive amino acids of M1 (SEQ ID NO: 1), M3 (SEQ ID NO: 3), or M5 (SEQ ID NO: 5) of TDP-43.

In other embodiments, the therapeutic peptide can correspond to a portion of the M1 internal motif of TDP-43. A therapeutic peptide corresponding to a portion of the M1 internal motif of TDP-43 can include, consist essentially of, or consist of a peptide having an amino acid sequence of FPGACGL (SEQ ID NO: 1) or AQFPGACGL (SEQ ID NO: 7).

In still other embodiments, the therapeutic peptide can correspond to a portion of the M3 internal motif of TDP-43.

A therapeutic peptide corresponding to a portion of the M1 internal motif of TDP-43 can include, consist essentially of, or consist of a peptide having an amino acid sequence of GFGFV (SEQ ID NO: 3) or SKGFGFVRF (SEQ ID NO: 8).

In yet other embodiments, the therapeutic peptide can correspond to a portion of the M5 internal motif of TDP-43. A therapeutic peptide corresponding to a portion of the M1 internal motif of TDP-43 can include, consist essentially of, or consist of a peptide having an amino acid sequence of GGGAGLG (SEQ ID NO: 5) or SRGGGAGLG (SEQ ID NO: 9).

The therapeutic peptides described herein can be subject to other various changes, substitutions, insertions, and deletions where such changes provide for certain advantages in its use. In this regard, therapeutic peptides that correspond to the mitochondrial internal targeting signal of TDP-43 can correspond to or be substantially homologous with, rather than be identical to, the sequence of a recited polypeptide where one or more changes are made and it retains the ability to inhibits or reduces TDP-43 mitochondrial localization.

The therapeutic peptide can be in any of a variety of forms of polypeptide derivatives, that include amides, conjugates with proteins, cyclized polypeptides, polymerized polypeptides, analogs, fragments, chemically modified polypeptides, and the like derivatives.

The therapeutic peptides can also be modified by natural processes, such as posttranslational processing, and/or by chemical modification techniques, which are known in the art. Modifications may occur anywhere in the peptide including the peptide backbone, the amino acid side-chains and the amino or carboxy termini. It will be appreciated that the same type of modification may be present in the same or varying degrees at several sites in a given peptide. Modifications comprise for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Other type of peptide modifications may include for example, amino acid insertion (i.e., addition), deletion and substitution (i.e., replacement), either conservative or non-conservative in the polypeptide sequence where such changes do not substantially alter the overall inhibitor ability of the peptide and may even provide for certain advantages in its use. In this regard, a peptide that is an inhibitor of TDP-43 localization corresponds to, rather than is identical to, the sequence of a recited peptide where one or more changes are made and it retains the ability to function as an inhibitor of TDP-43 localization.

Therapeutic peptides described herein may also include, for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues involve an insertion or a substitution of one or more amino acids.

The therapeutic peptides described herein may be prepared by methods known to those skilled in the art. The peptides and/or proteins may be prepared using recombinant DNA. For example, one preparation can include cultivating a host cell (bacterial or eukaryotic) under conditions, which provide for the expression of peptides and/or proteins within the cell The purification of the polypeptides may be done by affinity methods, ion exchange chromatography, size exclusion chromatography, hydrophobicity or other purification technique typically used for protein purification. The purification step can be performed under non-denaturating conditions. On the other hand, if a denaturating step is required, the protein may be renatured using techniques known in the art.

In some embodiments, the therapeutic peptides described herein can include additional residues that may be added at either terminus of a polypeptide for the purpose of providing a "linker" by which the polypeptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject polypeptide can differ by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the therapeutic peptide to other polypeptides, proteins, and/or molecules, such as detectable moieties, labels, solid matrices, or carriers. A flexible peptide linker can be about 20 or fewer amino acids in length. For example, a peptide linker can contain about 12 or fewer amino acid residues, e.g., 3, 4, 5, 6, 7, 8, 9, 10, 11, and 12. In some cases, a peptide linker comprises two or more of the following amino acids: glycine, serine, alanine, and threonine.

In some embodiments, a therapeutic agent comprising the therapeutic peptides described herein can be provided in the form of a conjugate protein or drug delivery construct includes at least a cell transport subdomain(s) or moiety(ies) (i.e., transport moieties), which is linked to the therapeutic peptide. The transport moieties can facilitate uptake of the therapeutic polypeptides into a mammalian (i.e., human or animal) tissue or cell (e.g., neural cell). The transport moieties can be covalently linked to the therapeutic polypeptides. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the therapeutic polypeptide. The transport moieties can also be linked to the therapeutic polypeptide with linking polypeptide described herein.

The transport moieties can be repeated more than once in the therapeutic agent. The repetition of a transport moiety may affect (e.g., increase) the uptake of the peptides and/or proteins by a desired cell. The transport moiety may also be located either at the amino-terminal region of therapeutic peptide or at its carboxy-terminal region or at both regions.

In one embodiment, the transport moiety can include at least one transport peptide sequence that allows the therapeutic peptide once linked to the transport moiety to penetrate into the cell by a receptor-independent mechanism. In one example, the transport peptide is a synthetic peptide that contains a Tat-mediated protein delivery sequence (e.g., YGRKKRRQRRR (SEQ ID NO: 11)). The transport peptide can be fused to at least one therapeutic peptides described having at least one of SEQ ID NOs: 1, 3, 5, 7, 8, or 9. These peptides can have, respectively, the amino acid sequences of SEQ ID NOs: 12-17.

Other examples of known transport moieties, subdomains and the like are described in, for example, Canadian patent document No. 2,301,157 (conjugates containing homeodomain of antennapedia) as well as in U.S. Pat. Nos. 5,652,122, 5,670,617, 5,674,980, 5,747,641, and 5,804,604, all of which are incorporated herein by reference in their entirety, (conjugates containing amino acids of Tat HIV protein; herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

A 16 amino acid region of the third alpha-helix of antennapedia homeodomain has also been shown to enable proteins (made as fusion proteins) to cross cellular membranes (PCT international publication number WO 99/11809 and Canadian application No. 2,301,157. Similarly, HIV Tat protein was shown to be able to cross cellular membranes.

In addition, the transport moiety(ies) can include polypeptides having a basic amino acid rich region covalently linked to an active agent moiety (e.g., intracellular domain-containing fragments inhibitor peptide). As used herein, the term "basic amino acid rich region" relates to a region of a protein with a high content of the basic amino acids such as arginine, histidine, asparagine, glutamine, lysine. A "basic amino acid rich region" may have, for example 15% or more of basic amino acid. In some instance, a "basic amino acid rich region" may have less than 15% of basic amino acids and still function as a transport agent region. In other instances, a basic amino acid region will have 30% or more of basic amino acids.

The transport moiety(ies) may further include a proline rich region. As used herein, the term proline rich region refers to a region of a polypeptide with 5% or more (up to 100%) of proline in its sequence. In some instance, a proline rich region may have between 5% and 15% of prolines. Additionally, a proline rich region refers to a region, of a polypeptide containing more prolines than what is generally observed in naturally occurring proteins (e.g., proteins encoded by the human genome). Proline rich regions of this application can function as a transport agent region.

In one embodiment, the therapeutic peptide described herein can be non-covalently linked to a transduction agent. An example of a non-covalently linked polypeptide transduction agent is the Chariot protein delivery system (See U.S. Pat. No. 6,841,535; *J Biol Chem* 274(35):24941-24946; and *Nature Biotec*. 19:1173-1176, all herein incorporated by reference in their entirety).

In other embodiments, the therapeutic peptides can be expressed in cells being treated using gene therapy to inhibit TDP-43 mitochondrial localization. The gene therapy can use a vector including a nucleotide encoding the therapeutic peptides. A "vector" (sometimes referred to as gene delivery or gene transfer "vehicle") refers to a macromolecule or complex of molecules comprising a polynucleotide to be delivered to the cell. The polynucleotide to be delivered may comprise a coding sequence of interest in gene therapy. Vectors include, for example, viral vectors (such as adenoviruses (Ad), adeno-associated viruses (AAV), and retroviruses), liposomes and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use herein include viral vectors, lipid based vectors and other non-viral vectors that are capable of delivering a nucleotide encoding the therapeutic peptides described herein to the target cells. The vector can be a targeted vector, especially a targeted vector that preferentially binds to neurons and. Viral vectors for use in the application can include those that exhibit low toxicity to a target cell and induce production of therapeutically useful quantities of the therapeutic peptide in a cell specific manner.

Examples of viral vectors are those derived from adenovirus (Ad) or adeno-associated virus (AAV). Both human and non-human viral vectors can be used and the recombinant viral vector can be replication-defective in humans. Where the vector is an adenovirus, the vector can comprise a polynucleotide having a promoter operably linked to a gene encoding the therapeutic peptides and is replication-defective in humans.

Other viral vectors that can be used herein include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, might also be used in the application. For example, retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and a nucleic acid encoding the therapeutic peptide. In methods of delivery to neural cells, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells.

Lentiviral vectors for use in the application may be derived from human and non-human (including SIV) lentiviruses. Examples of lentiviral vectors include nucleic acid sequences required for vector propagation as well as a tissue-specific promoter operably linked to a therapeutic peptide encoding nucleic acid. These former may include the viral LTRs, a primer binding site, a polypurine tract, att sites, and an encapsidation site.

In some aspects, a lentiviral vector can be employed. Lentiviruses have proven capable of transducing different types of CNS neurons (Azzouz et al., (2002) *J Neurosci.* 22: 10302-12) and may be used in some embodiments because of their large cloning capacity.

A lentiviral vector may be packaged into any lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN) might also be used in the application. Use of alphaviruses is described in Lundstrom, K., Intervirology 43:247-257, 2000 and Perri et al., Journal of Virology 74:9802-9807, 2000.

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods of the application, more than one promoter can be included in the vector to allow more than one heterologous gene to be expressed by the vector. Further, the vector can comprise a sequence, which encodes a signal peptide or other moiety, which facilitates expression of the therapeutic peptide from the target cell.

To combine advantageous properties of two viral vector systems, hybrid viral vectors may be used to deliver a nucleic acid encoding a therapeutic peptide to a target neuron, cell, or tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000. Retroviral genomes contained within an adenovirus may integrate within the target cell genome and effect stable gene expression.

Other nucleotide sequence elements, which facilitate expression of the therapeutic peptide and cloning of the vector are further contemplated. For example, the presence of enhancers upstream of the promoter or terminators downstream of the coding region, for example, can facilitate expression.

In accordance with another embodiment, a tissue-specific promoter can be fused to nucleotides encoding the therapeutic peptides described herein. By fusing such tissue specific promoter within the adenoviral construct, transgene expression is limited to a particular tissue. The efficacy of gene expression and degree of specificity provided by tissue specific promoters can be determined, using the recombinant adenoviral system of the present application. Neuron specific promoters, such as the platelet-derived growth factor β-chain (PDGF-β) promoter and vectors, are well known in the art.

In addition to viral vector-based methods, non-viral methods may also be used to introduce a nucleic acid encoding a therapeutic peptide into a target cell. A review of non-viral methods of gene delivery is provided in Nishikawa and Huang, Human Gene Ther. 12:861-870, 2001. An example of a non-viral gene delivery method according to the application employs plasmid DNA to introduce a nucleic acid encoding a therapeutic peptide into a cell. Plasmid-based gene delivery methods are generally known in the art.

Synthetic gene transfer molecules can be designed to form multimolecular aggregates with plasmid DNA. These aggregates can be designed to bind to a target cell. Cationic amphiphiles, including lipopolyamines and cationic lipids, may be used to provide receptor-independent nucleic acid transfer into target cells.

In addition, preformed cationic liposomes or cationic lipids may be mixed with plasmid DNA to generate cell-transfecting complexes. Methods involving cationic lipid formulations are reviewed in Feigner et al., Ann. N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

Methods that involve both viral and non-viral based components may be used according to the application. For example, an Epstein Barr virus (EBV)-based plasmid for therapeutic gene delivery is described in Cui et al., Gene Therapy 8:1508-1513, 2001. Additionally, a method involving a DNA/ligand/polycationic adjunct coupled to an adenovirus is described in Curiel, D. T., Nat. Immun 13:141-164, 1994.

Additionally, the nucleic acid encoding the therapeutic peptides can be introduced into the target cell by transfecting the target cells using electroporation techniques. Electroporation techniques are well known and can be used to facilitate transfection of cells using plasmid DNA.

Vectors that encode the expression of the therapeutic peptides can be delivered in vivo to the target cell in the form of an injectable preparation containing pharmaceutically acceptable carrier, such as saline, as necessary. Other pharmaceutical carriers, formulations and dosages can also be used in accordance with the present application.

Where the target cell includes a neuron being treated the vector can be delivered by direct injection at an amount sufficient for the therapeutic peptide to be expressed to a degree, which allows for highly effective therapy. By injecting the vector directly into or about the periphery of the neuron, it is possible to target the vector transfection rather effectively, and to minimize loss of the recombinant vectors. This type of injection enables local transfection of a desired number of cells, especially at a site of CNS injury, thereby maximizing therapeutic efficacy of gene transfer, and minimizing the possibility of an inflammatory response to viral proteins. Other methods of administering the vector to the target cells can be used and will depend on the specific vector employed.

The therapeutic peptide can be expressed for any suitable length of time within the target cell, including transient expression and stable, long-term expression. In one aspect of the application, the nucleic acid encoding the therapeutic peptide will be expressed in therapeutic amounts for a defined length of time effective to induce activity and growth of the transfected cells. In another aspect of the application, the nucleic acid encoding the therapeutic peptide will be expressed in therapeutic amounts for a defined length of time effective to treat neurodegenerative disease or disorder.

A therapeutic amount is an amount, which is capable of producing a medically desirable result in a treated animal or human. As is well known in the medical arts, dosage for any one animal or human depends on many factors, including the subject's size, body surface area, age, the particular composition to be administered, sex, time and route of administration, general health, and other drugs being administered concurrently. Specific dosages of proteins and nucleic acids can be determined readily determined by one skilled in the art using the experimental methods described below.

The therapeutic agents described herein may further be modified (e.g., chemically modified). Such modification may be designed to facilitate manipulation or purification of the molecule, to increase solubility of the molecule, to facilitate administration, targeting to the desired location, to increase or decrease half life. A number of such modifications are known in the art and can be applied by the skilled practitioner.

In another aspect, the therapeutic agents can be provided in a pharmaceutical compositions. The pharmaceutical compositions will generally comprise an effective amount of agent, dissolved or dispersed in a pharmaceutically acceptable carrier or aqueous medium. Combined therapeutics are also contemplated, and the same type of underlying pharmaceutical compositions may be employed for both single and combined medicaments.

In some embodiments, the therapeutic agents can be formulated for parenteral administration, e.g., formulated for injection via the subcutaneous, intravenous, intramuscular, transdermal, intravitreal, or other such routes, including peristaltic administration and direct instillation into targeted site. The preparation of an aqueous composition that contains such a therapeutic agent as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms that can be used for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

Compositions of the therapeutic agents can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Examples of carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the therapeutic agents can be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Examples of pharmaceutical compositions can generally include an amount of the TDP-43 mitochondrial localization inhibitor peptide admixed with an acceptable pharmaceutical diluent or excipient, such as a sterile aqueous solution, to give a range of final concentrations, depending on the intended use.

Formulation of the pharmaceutical compounds for use in the modes of administration noted above (and others) are known in the art and are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y., U.S.A., 2005; and Mathiowitz et al., eds., Bioadhesive Drug Delivery Systems, Drugs and the Pharmaceutical Sciences Series, Marcel Dekker, Inc., N.Y., U.S.A., 1999. Compounds of the invention can be formulated into pharmaceutical compositions containing pharmaceutically acceptable non-toxic excipients and carriers. The excipients are all components present in the pharmaceutical formulation other than the active ingredient or ingredients. Suitable excipients and carriers useful in the present invention are composed of materials that are considered safe and effective and may be administered to an individual without causing undesirable biological side effects, or unwanted interactions with other medications. Suitable excipients and carriers are those, which are composed of materials that will not affect the bioavailability and performance of the agent. As generally used herein "excipient" includes, but is not limited to surfactants, emulsifiers, emulsion stabilizers, emollients, buffers, solvents, dyes, flavors, binders, fillers, lubricants, and preservatives. Suitable excipients include those generally known in the art such as the "Handbook of Pharmaceutical Excipients", 4th Ed., Pharmaceutical Press, 2003.

Formulations of the therapeutic agents are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, topical formulations, liposomal forms and the like. The type of form for administration will be matched to the disease or disorder to be treated.

Pharmaceutical "slow release" capsules or "sustained release" compositions or preparations may be used and are generally applicable. Slow release formulations are generally designed to give a constant drug level over an extended period and may be used to deliver a TDP-43 mitochondrial localization inhibitor peptide in accordance with the present invention. The slow release formulations are typically implanted in the vicinity of the disease site.

Examples of sustained-release preparations include semipermeable matrices of solid hydrophobic polymers containing the polypeptide or immunoconjugate, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers, such as the Lupron Depot (injectable microspheres composed of lactic acid-glycolic acid copolymer and leuprolide acetate); and poly-D-(-)-3-hydroxybutyric acid.

While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

In some embodiments, the therapeutic agents and pharmaceutical compositions comprising the therapeutic agents described herein may be delivered to neurons of the CNS and/or the PNS. Such neurons may be injured or diseased. Such neurons may alternatively be healthy, uninjured neurons. Such neurons may be located at the site of injury, or at a site incident to the injury. The neurons to be targeted for therapeutic administration, delivery/contact of the agents and compositions described herein will be neurons from which inhibition of neuronal degeneration or death is thought to prove beneficial to the subject. Such determination is within the ability of the skilled practitioner through no more than routine experimentation.

The therapeutic agents and therapeutic pharmaceutical compositions described herein may also be delivered to non-neuronal cells of the CNS and/or the PNS, such as to non-neuronal cells that provide support to neural cells. Such cells include, without limitation, glial cells (e.g., astrocytes, oligodendrocytes, ependymal cells, radial glia in the CNS; and Schwann cells, satellite glial cells, enteric glaial cells n the PNS).

In some embodiments, the pharmaceutical compositions including one or more therapeutic agents can be provided and administered to a subject for the in vivo inhibition of TDP-43 mitochondrial localization. The pharmaceutical compositions can be administered to any subject that can experience the beneficial effects of the therapeutic agents. Foremost among such animals are humans, although the present invention is not intended to be so limited, may be used to treat animals and patients with a neurodegenerative disease.

Pharmaceutical compositions for use in the methods described herein can have a therapeutically effective amount of the agent in a dosage in the range of .01 to 1,000 mg/kg of body weight of the subject, and more preferably in the range of from about 1 to 100 mg/kg of body weight of the patient. In certain embodiments, the pharmaceutical compositions for use in the methods of the present invention have a therapeutically effective amount of the agent in a dosage in the range of 1 to 10 mg/kg of body weight of the subject.

The overall dosage will be a therapeutically effective amount depending on several factors including the particular agent used, overall health of a subject, the subject's disease state, severity of the condition, the observation of improvements, and the formulation and route of administration of the selected agent(s). Determination of a therapeutically effective amount is within the capability of those skilled in the art. The exact formulation, route of administration and dosage can be chosen by the individual physician in view of the subject's condition.

In some embodiments, the therapeutic agents can be used to treat diseases, disorders, or condition associated with elements of the nervous system, including the central, somatic, autonomic, sympathetic and parasympathetic components of the nervous system, neurosensory tissues within the eye, ear, nose, mouth or other organs, as well as glial tissues associated with neuronal cells and structures. The neurodegenerative diseases or disorders may be characterized and/or associated with aberrant TDP-43 mitochondrial localization, TDP-43 neuronal toxicity, and/or mutations of TDP-43. The neurodegenerative disease can include, for example, amyotrophic lateral sclerosis (ALS), frontotemporal dementia (FTD), Alzheimer's disease, dementias related to Alzheimer's disease, Parkinson's, senile dementia, Huntington's disease, Gilles de Ia Tourette's syndrome, multiple sclerosis, or hereditary motor and sensory neuropathy.

One particular aspect contemplates the treatment of ALS in a subject. The method includes administering to the subject a therapeutically effective amount of one or more therapeutic agents described. ALS is characterized phenotypically by progressive weakness and neuropathologically by loss of motor neurons. It is contemplated that methods of the present invention can abolish wild-type and mutant TDP-43 induced mitochondrial dysfunction and neuronal loss thereby improving the disease phenotype in subjects with ALS.

Another strategy for treating a subject suffering from a neurodegenerative disease or disorder is to administer a therapeutically effective amount of a TDP-43 mitochondrial localization inhibitor described herein along with a therapeutically effective amount of additional anti-neurodegenerative disease agent. Examples of anti-neurodegenerative disease agents include L-dopa, cholinesterase inhibitors, anticholinergics, dopamine agonists, steroids, and immunomodulators including interferons, monoclonal antibodies, and glatiramer acetate.

Therefore, in a further aspect of the invention, a therapeutic agent described herein can be administered as part of a combination therapy with adjunctive therapies for treating neurodegenerative and myelin related disorders.

The phrase "combination therapy" embraces the administration of a therapeutic agent described herein (e.g., a TDP-43 mitochondrial localization inhibitor) and an additional therapeutic agent as part of a specific treatment regimen intended to provide a beneficial effect from the co-action of these therapeutic agents. When administered as a combination, a TDP-43 mitochondrial localization inhibitor and a therapeutic agent can be formulated as separate compositions. Administration of these therapeutic agents in combination typically is carried out over a defined time period (usually minutes, hours, days or weeks depending upon the combination selected).

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, subcutaneous routes, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (e.g., surgery).

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The Inhibition of TDP-43 Mitochondrial Localization Blocks Its Neuronal Toxicity It has yet to be determined whether loss of TDP-43 function via nuclear depletion or gain of function by adverse effect of cytoplasmic TDP-43 causes neuronal loss in ALS and FTD. This Example shows that TDP-43 cytoplasmic TDP-43 is sufficient to cause neuronal toxicity and neurodegeneration and inhibition of TDP-43 mitochondrial localization blocks neuronal its neuronal toxicity.

Materials and Methods

Immunocytochemistry and immunofluorescence of mouse and human spinal cord Human spinal cord tissues obtained postmortemly from University Hospitals of Cleveland were fixed and 6 μm-thick consecutive sections prepared as we described before (Table 1). Immunocytochemistry was performed by the peroxidase anti-peroxidase protocol. For immunofluorescent staining, deparaffinized and re-hydrated tissue sections were washed briefly three times with distilled $H_2O$ and placed in 1× antigen decloaker (Biocare, Concord, Calif.). The sections were then subject to antigen retrieval under pressure using Biocare's Decloaking Chamber by heating to 125° C. for 10 sec and cooling to 90° C. for 30 sec followed by heating to 22 psi at 128° C., and cooling to 0 psi at 94° C. After temperature decreased to 30° C., the sections were gradually rinsed with distilled $H_2O$ for five times. The sections were then blocked with 10% normal goat serum (NGS) for 30 min at RT, and incubated with primary antibodies in PBS containing 1% NGS overnight at 4° C. After 3 washes with PBS, the sections were incubated in 10% NGS for 10 min, and then with Alexa Fluor conjugated secondary antibody (Life Technologies, Grand Island, N.Y.) (1:300) for 2 h at RT in dark. Finally, the sections were rinsed three times with PBS, stained with DAPI, washed again with PBS for three times, and mounted with Fluoromount-G mounting medium (Southern Biotech, Birmingham, Ala.).

Expression Vectors, Recombinant Proteins, Peptides, Antibodies and Chemicals

MitoDsRed2 (Clontech, Mountain View, Calif.) and lentiviral packing plasmids (PCMV-dR8.2 and PCMV-VSVG from Addgene, Cambridge, Mass.) were obtained. Flag tagged TDP-43 constructs were generated by cloning TDP-43 into PCMV-3Tag-1a (Agilent, Santa Clara, Calif.) or pCMVTnT (Promega, Madison, Wis.). GFP fused with M1/3/5 constructs were generated based on PCMV-3Tag-9a (Agilent, Santa Clara, Calif.). TDP-43 mutations were all generated using QuikChange Lightning Site-Directed Mutagenesis Kit (Agilent, Santa Clara, Calif.). MitoDsRed2/TDP-43 bicistronic lentiviral constructs were generated by cloning TDP-43 and mitoDsRed2 into pLVX-Puro (Clontech) and replacing PCMV promotor with mouse synapsin 1 promoter. ND3 or ND6 gene in nuclear format with the addition of mitochondrial targeting sequence from subunit VIII of human cytochrome c oxidase to the 5'-terminus (and the addition of myc tag to the 3'-terminus) were directly synthesized and subcloned into pcDNA3.1(+) (GenScript). Primers used for RT-PCR/Realtime-PCR (Life Technologies, Grand Island, N.Y.) and RNAi oligonucleotides (Sigma St. Louis, Mo.; Tim22 esiRNAi: EHU160361-2OUG and Tim23 esiRNAi: EHU106141-519 2OUG) were obtained. His tagged recombinant human TDP-43 was obtained from ATGEN (Gyeonggi-do, South Korea) and Flag tagged recombinant human TDP-43 were synthesized in rabbit reticulocyte system by coupled transcription/translation with biotin-lysyl-tRNA using pCMVTnT constructs (Promega, Madison, Wis.). cPM, PM1 and PM3 peptides 523 (with/without FITC labeling) in which M1 or M3 motif or scrambled M1 or M3 motif fused to the 524 C-terminus of the protein transduction domain (YGRKKRRQRRR (SEQ ID NO: 11)) of the human immunodeficiency virus TAT protein to enhance peptide delivery/permeability as described were obtained from NeoBiolab (Woburn, Mass.) or Biomatik (Wilmington, Del.). All chemicals were obtained (Sigma St. Louis, Mo.).

Embryonic Primary Cortical Neuron, HEK293 Cells and Primary Human Fibroblasts Culture 530 and Transfection Primary cortical neurons were isolated from E18 Sprague Dawley rats (Harlan, Indianapolis, Ind.) as previously described with modifications. Taken briefly, rat brains were dissected out in HBSS (Life Technologies, Grand Island, N.Y.) and stored in Hibernate E (BrainBits, Springfield, Ill.) supplemented with 2% B27 (Life Technologies, Grand Island, N.Y.). Under a dissecting microscope, the meninges were removed completely with fine forceps and cortices were dissected out. Cortices were then digested in 0.25% trypsin for 15 min at room temperature (RT) followed by brief incubation in Opti-MEM (Life Technologies, Grand Island, N.Y.) supplemented with 10% FBS and 50 units/ml DNAse I (Worthington-biochem, Lakewood Township, N.J.). Digested cortices were further dissociated by gentle trituration with pipette until the cell suspension was homogenous and no large pieces of tissue remain visible. Cortical neurons were finally collected and seeded on poly-L-lysine/laminin coated coverslips/chamber slides (BD, Franklin Lakes, N.J.), 35 mm dishes or 24 well plates and cultured as we described before. HEK-293T cells from American Type Culture Collection (ATCC, Manassas, Va.) were grown in DMEM medium (Life Technologies, Grand Island, N.Y.), supplemented with 10% fetal bovine serum and 1% penicillin-streptomycin, in 5% $CO_2$ in a humid incubator at 37° C. Primary human fibroblasts from 4 age-matched normal subjects and 2 ALS patients bearing TDP-43 mutations (only 2 lines are available) were obtained from Coriell Institute for Medical Research (NINDS collection). Primary fibroblasts were grown in minimum essential medium (Life Technologies) containing non-essential amino acids and 2 mM glutamine, supplemented with 10% or 15% (v/v) fetal bovine serum, in 5% $CO_2$ in a humid incubator at 37° C. as we described before. HEK293 cells and primary human fibroblasts were tested free of mycoplasma contamination. Neurons were all transfected by NeuroMag (OZ Biosciences, San Diego, Calif.), while HEK293T cells and primary fibroblasts were transfected with lipofectamine 2000 (Life Technologies, Grand Island, N.Y.) according to manufacturer's protocol. For co-transfection, a 3:1 ratio (mitoDsRed2/TDP-43:GFP) was applied.

Generation of iPSCs Using Human Fibroblasts and Differentiation of iPSCs to Human Neurons For reprogramming and differentiation, two lines of NHFs and TDP-43 G298S or A382T human fibroblasts were cultured in DMEM supplemented with 10% FBS (Life Technologies) and GlutaMAX (Life Technologies). Fibroblasts were reprogrammed using CytoTune-iPS 2.0 Sendai Reprogramming Kit (Life Technologies) according to manufacturer's instruction using irradiated MEFs (iMEF) as feeder cells. iPSCs were routinely cultured on iMEFs in hESC medium (DMEM/F12 with GlutaMAX (Life Technologies), 10% KnockOut Serum Replacement (Life Technologies), 0.1 mM 2-mercaptoethanol (Life Technologies), 1× Non-Essential Amino Acids (Life Technologies), and 10 ng/ml bFGF (Sigma). For differentiation, iPSCs were adapted and cultured in a feeder free conditions on matrigel in TeSR1 E8 medium (Stem Cell Technologies) and differentiated into induced neuronal progenitor cells (iNPCs) using StemDiff Neural Induction Medium and AggreWell 800 (both from Stem Cell Technologies) according to instructions. iNPCs were selected using Neural Rosette Selection Medium and further expanded using neural progenitor medium (both from Stem Cell Technologies). For characterization of iPSCs and iNPCs, immunofluorescence staining was carried out as previously described using antibodies against TRA-1-81, Nanog, SSEA3 and SSEA4. For alkaline phosphatase (AP) staining, Alkaline Phosphatase Staining Kit II (Stemgent) was used. iNPCs were differentiated into human neurons using Axol iNPCs differentiation and maturation kits (Axol, Cambridgeshire, United Kingdom) following manufacturer's protocol. Taken briefly, iNPCs cells were first seeded on 24 or 48 well plates or 24 well seahorse plates coated with Axol SureBondXF in Axol Plating-XF medium. 24 hours after plating, cells were transferred into neuronal differentiation medium (Axol Neuronal Differentiation-XF medium). After 72 hours, half of neuronal differentiation medium was replaced with neuronal maturation medium (Axol Neuronal Maintenance-XF medium) followed by half neuronal maturation medium change every four days. iPSCs and iNPCs used in the study were tested free of mycoplasma contamination. iPSCs derived neurons were also transfected by NeuroMag (OZ Biosciences, San Diego, Calif.).

Cellular and Mitochondrial Fractionation

Mitochondria were isolated as described before. Taken briefly, cells were homogenized in IB-1 solution (IB-1: 225 mM mannitol, 75 mM sucrose, 0.1 mM EGTA, 20 mM HEPES; pH=7.4), while tissues were homogenized in IB-1 with 0.5% BSA. The total homogenate (H) was 17 centrifuged at 600 g for two times at 4 for 5 mM. Subsequently, the supernatant (S1) was collected and centrifuged at 7,000 g at 4 for 10 mM to obtain enriched mitochondrial fraction and the supernatant (S2) was collected. The enriched mitochondrial fraction was washed in IB-2 solution (225 mM mannitol, 75 mM sucrose, 20 mM HEPES; pH=7.4) for cell mitochondria and IB-2 containing 0.5% BSA for tissue mitochondria followed by centrifugation at 9,000 g for 10 mM The pellets were suspended in MRB buffer (250 mM Mannitol, 0.5 mM EGTA, 5 mM HEPES; pH 7.4) to obtain crude mitochondrial fraction (cM). The crude mitochondrial fraction was further overlaid on top of 8 ml Percoll medium (225 mM mannitol, 25 mM HEPES, 1 mM EGTA and 30% Percoll (vol/vol); pH=7.4] and subjected to centrifugation at 95,000 g for 30 mM at 4 in a SW40 Ti rotor. The pellet was suspended in MRB buffer again followed by centrifugation at 6,300 g for 10 mM at 4 to obtained purified mitochondria (pM). Nuclear fraction was isolated/purified by nuclear extraction reagents (Thermo scientific, Waltham, Mass.). For sub-mitochondrial compartment fractionation, isolated pure mitochondria were suspended in isolation medium (225 mM mannitol, 75 mM sucrose, 0.1 mM EGTA, 20 mM HEPES; pH 15=7.4) with digitonin at 0.12 mg digitonin/mg mitochondria and stirring gently on ice for min. Then digitonin treated samples were diluted with 3 volume of isolation medium and centrifuged at 9,000 g for 10 mM to get supernatant A followed by pellet resuspension in isolation buffer and sonicated for 30 seconds on ice. Then the solution was sonicated and centrifuged at 6,500 g for 10 mM followed by centrifugation at 144,000 g for 60 mM to sediment the inner membrane vesicles and the supernatant was collected as matrix fraction. Supernatant A was centrifuged at 144,000 g for 60 mM to sediment outer membrane vesicles as pellets and the supernatant was collected as inner membrane space fraction.

Synaptosome Isolation S

Synaptosomes were isolated from mouse cortices or spinal cords as described. Taken briefly, fresh cortex tissue was homogenized in ice cold 'Sucrose Medium' (320 mM sucrose, 1 mM EDTA, 0.25 mM dithiothreitol, pH 7.4 followed by centrifugation at 1,000 g for 10 mM at 4. The supernatant was collected and carefully layered on top of a discontinuous Percoll gradient (3 mL layers of 3, 10, and 23% Percoll in sucrose medium) in a 15 mL centrifuge tube followed by centrifugation at 32,500 g for 10 mM at 4 in a SW-40Ti rotor. The band between 10% and 23% Percoll was collected and diluted into ionic medium (20 mM HEPES, 10 mM D-glucose, 1.2 mM $Na_2HPO_4$, 1 mM $MgCl_2$, 5 mM $NaHCO_3$, 5 mM KCl, 140 mM NaCl, pH. 7.4) followed by centrifugation at 15,000 g for 15 min at 4 to remove Percoll. The pellets, i.e., synaptosome fractions, were collected and resuspended in ionic media again and seeded on polyethyleneimine coated plates by centrifugation at 3,000 g at 4 for 30 min. The purity of synaptosome was confirmed by immunoblot of synaptic makers or EM (data not shown).

Mitochondrial Function and Cell Viability Measurement

The $m\Delta_\psi$ in HEK293 cells, human fibroblasts, primary neurons or synaptic mitochondria was determined by tetramethylrhodamine (TMRM) and/or rhodamine 123 (rhod123) as we described before. Taken briefly, HEK293 cells, human fibroblasts, primary neurons cultured in 35 mm 630 dishes or 24 well plates, or isolated synaptosomes attached to 24 well plates pre-coated with polyethyleneimine as described (1:15000 dilution from a 50% solution, Sigma) were incubated with 20 nM TMRM or 2 μM rhod123 in PBS (Phosphate-Buffered Saline pH 7.4, Life Technologies, Grand Island, N.Y.; for HEK293 cells and human fibroblasts), HEPES-buffered Tyrode's solution (119 mM NaCl, 5 mM KCl, 6 g/liter D-glucose, 2 mM CaCl2, 2 mM $MgCl_2$, and 25 mM HEPES; pH 7.4; for primary neurons) or ionic medium (for synaptic mitochondria) for 30 min. The TMRM/rhod123 containing solution was removed. After three times wash with PBS, Tyrode's or ionic medium, cells/neurons/synaptosome were incubated in PBS or Tyrode's solution at 37° C. in room air for 10 min to allow the stead of TMRM/rhod123 signal before imaging by fluorescence microscope. ATP levels were measured by the ATP 18 Colorimetric/Fluorometric Assay Kit (Biovision, Milpitas, Calif.) using cell or neuronal lysate as described before. The real-time measurement of oxygen consumption rate (OCR) in live cultured HEK293 cells, human fibroblasts and neurons with optimal seeding density as indicated or synaptic mitochondria in synaptosomes was performed using the Seahorse XF24 Analyzer (Seahorse Bioscience, North Billerica, Mass.) according to the manufacture's instruction. If needed, ATP synthase inhibitor oligomycin (1 μM), uncoupler FCCP (4 μM) and complex I inhibitors antimycin A (1 μM) and rotenone (1 μM) were injected sequentially. After measurement, cells and synaptosomes were lysed and OCR data was normalized by total protein. Cell death and viability was measured by Cytotoxicity Detection Kit (LDH; Roche, Nutley, N.J.), immunofluorescent staining using a specific antibody against cleaved caspase 3 staining or SYTOX green assay (Life Technologies, Grand Island, N.Y.). For SYTOX green dead neuron staining, neurons were incubated in PBS containing 30 nM SYTOX green for 20 minutes at room temperature followed by three times wash with PBS. Neurons with SYTOX green-positive nuclei and/or obvious fragmented nuclear/neurites were counted as non-viable neurons, whereas neurons without SYTOX green-positive nuclei and clear nuclear contour/neurites were counted as viable neurons.

Mitochondria Import Assay

Mitochondria were isolated from mouse brain, while mitoplasts were prepared by incubating isolated mitochondria with digitonin (0.1 mg per 1 mg of mitochondrial protein) on ice for 15 mM followed by centrifugation at 11,000 g for 10 mM The import buffer used was composed of 250 mM sucrose, 10 mM MOPS-KOH, pH 7.2, 80 mM KCl, 5 mM $MgCl_2$, 2 mM ATP, 2 mM NADH, 3% BSA. The import assays were carried out by incubating mitochondria or mitoplasts with indicated recombinant proteins at RT for 45 min. The import reactions were stopped by adding valinomycin (1 µM). Equal volume of import reactions were treated by trypsin and/or digitonin as needed at RT for 5 mM followed by centrifugation at 11,000 g for 10 min. At last, the mitochondria or mitoplasts pellets were resuspended in cell lysis buffer (Cell signaling, Danvers, Mass.) supplemented with protease inhibitor cocktail (Roche, Nutley, N.J.) and phenylmethylsulfonyl fluoride (PMSF, Sigma, St. Louis, Mo.). Mitochondrial proteins need to be unfolded during import, suggesting the existence of chaperones in reticulocyte lysates facilitating rTDP-43 import in vitro. Although rTDP-43 import could be increased by urea-denaturation (data not shown), recombinant proteins generated in reticulocyte lysates also demonstrated efficient import in vitro. Therefore, in this study, we used recombinant proteins without denaturation.

Measurements of Activities of Respiratory Chain Complex I to V

Enzyme activity of complex I-IV was measured as described. Taken briefly, after three cycles of freeze and thaw, isolated mitochondria were resuspended in a total volume of 200 µl reaction buffer. Complex I (NADH: ubiquinone oxidoreductase) activity was measured in reaction buffer containing 25 mM potassium phosphate, 5 mM $MgCl_2$, 2.5 mg/ml of BSA, 0.13 mM NADH, 2 µg/ml antimycin A, and 65 µM ubiquinone1 at 340 nm for 5 min before and after the addition of rotenone (2 µg/ml). Complex II (succinate: ubiquinone oxidoreductase) activity was measured in reaction buffer containing 25 mM potassium phosphate, 2.5 mg/ml of BSA, 20 mM sodium succinate, 0.05 mM DCPIP, 2 mM KCN, and 65 µM ubiquinone1 at 600 nm. The reaction was started through the addition of 65 µM ubiquinone1. Complex III (ubiquinol2:cytochrome c reductase) activity was measured in reaction buffer containing 25 mM potassium phosphate, 2.5 mg/ml of BSA, 2 mM KCN, 2 µg/ml rotenone, 0.6 mM n-dodecyl-b-D-maltoside, 15 µM cytochrome c and 35 µM ubiquinol2 at 550 nm. Complex IV (cytochrome c oxidase) activity was measured in reaction buffer containing 25 mM potassium phosphate, 0.45 mM n-dodecyl-b-D-maltoside and 15 µM cytochrome c. Complex IV activity at 550 nm. Complex V (F1-ATP synthase) activity was determined in assay buffer containing 40 mM Tris-HCO3, 10 mM EGTA pH8.0, 0.2 mM NADH, 2.5 mM PEP, 25 µg/ml antimycin A, 0.5 mg/ml LDH, 0.5 mg/ml PK and 2.5 mM ATP. Complex V activity was measured following the change in absorbance at 340 nm due to NADH oxidation.

RNA Immunoprecipitation and RT-PCR/Real Time PCR

Isolated mitochondria were first lysed by immunoprecipitation lysis buffer (50 mM Tris, pH 7.4,250 mM NaCl, 5 mM EDTA, 50 mM NaF, 1 mM Na3VO4, 1% Nonidet P40 (NP40) and 0.02% NaN3) containing 1× protease inhibitor cocktail (Cell signaling, Danvers, Mass.) and 100 U/ml Ribonuclease Inhibitor (Life Technologies, Grand Island, N.Y.). The homogenate was then centrifuged at 18,000 g at 4° C. for 30 mM The supernatant was collected and incubated with magnetic beads bound by TDP43 antibody overnight at 4° C. Magnetic beads were then washed with lysis buffer and RNAs were extracted by TRIzol reagent (Life Technologies, Grand Island, N.Y.). Total RNAs from HEK-293T cells and human spinal cord tissues were also extracted by TRIzol reagent (Life Technologies, Grand Island, N.Y.). mtDNA was removed by DNase I treatment and was verified by PCR. Reverse transcriptions were performed by High Capacity cDNA Reverse Transcription Kit with random oligomer primers (Life Technologies, Grand Island, N.Y.). qRT-PCR analysis of all mitochondria transcripts were performed on StepOnePlus system with appropriate primer pairs using SYBR Green master mix (Life Technologies, Grand Island, N.Y.). See table 1 for primers used (A8/ND4L have not been specifically measured and amplified due to their short sequences).

Mitochondrial Nascent Protein Synthesis in HEK293 Cells

HEK293 cells expressing Flag tagged TDP-43 were cultured in DMEM culture medium without methionine (Life Technologies, Grand Island, N.Y.) for 1 h followed by pretreatment with 0.1 mg/ml emetine for 10 mM and co-treatment with. 1 mg/ml emetine and L-Azidohomoalanine (AHA, Life Technologies, Grand Island, N.Y.) for 4 h. After pulse labelling, cells were harvested followed by mitochondrial fractionation. Isolated mitochondria were lysed with 1% SDS in 50 mM Tris-HCl, pH8.0 followed by centrifuged at 10,000 g for 10 min. The supernatant was incubated with avidin-dynabeads (Life Technologies, Grand Island, N.Y.) at RT for 30 mM After the removal of beads, the supernatant was subjected to Click-it assay (Life Technologies, Grand Island, N.Y.). Taken briefly, 200 µg mitochondria proteins were labeled with PEG4-carboxamide-6-Azidohexanyl-biotin in a 160 µL volume system, and total proteins were precipitated and extracted by methanol and chloroform. After the centrifugation for at 18,000 g for 5 min, the total protein pellets were collected and dissolved by 1% SDS in 50 mM Tris-HCl for western blot.

Fractionation for Mitochondrial Ribosomes and Their Loading on RNAs

Isolated mitochondria were lysed in lysis buffer (260 mM sucrose, 100 mM KCl, 20 mM $MgCl_2$, 10 mM Tris-Cl pH 7.5, 1% Triton X-100, 5 mM β-mercaptoethanol and protease inhibitor) on ice for 20 mM Lysates were centrifuged at 9,400 g for 30 mM at 4° C. Then supernatants were loaded on 11 ml 10%-30% continuous linear sucrose gradient (50 mM Tris-Cl, 100 mM KCl, 10 mM $MgCl_2$) and centrifuged at 20,400 rpm for 15 hour in a Beckman SW41-Ti rotor at 4° C. After centrifugation, 13 fractions were collected from the top and used for further immunoblot and 732 qRT-PCR analysis.

Blue Native PAGE and Immunoblot Analysis

Blue native gel electrophoresis was performed with NativePAGE Bis-Tris Gel system (Life Technologies, Grand Island, N.Y.). Briefly, isolated mitochondria containing 10 µg of mitochondrial proteins were resuspended in sample buffer and solubilized with 2% digitonin (Sigma) for 30 min on ice. Insolubilized pellets were removed by centrifugation for 30 mM at 18,000 g. The supernatant was collected and 5% G-250 sample additive was added. Samples were loaded to 3-12% precast Bis-Tris gradient gels (Life Technologies, Grand Island, N.Y.) followed by electrophoresis at a voltage of 40 V with light blue running buffers at 4° C. For regular immunoblot analysis, purified mitochondria, cells or tissues were lysed with cell lysis buffer (Cell signaling, Danvers, Mass.) plus 1 mM PMSF and protease inhibitor cocktail (Roche, Nutley, N.J.). Equal amounts of total protein extract were resolved by SDS-PAGE and transferred to Immobilon-P (Millipore, Billerica, Mass.). Following blocking with 10% nonfat dry milk, primary and secondary antibodies were applied as previously described and the blots were developed with Immobilon Western Chemiluminescent HRP Substrate (Millipore, Billerica, Mass.). Frozen human thoracic spinal cord tissues from 6 age-matched normal and 8 patients with sALS were obtained from NICHD Brain and Tissue Bank (Table 1).

RNA-Protein In Vitro Binding Assay

ND3 RNA and mutant ND3 RNA probe were purchased from GenScript (Piscataway, N.J.). RNA-protein binding was performed in 20 μL reactions containing 1 μM RNA probe. The binding conditions were 10 mM Tris at pH 7.5, 10 mM HEPES at pH 7.5, 20 mM KCl, 2 mM $MgCl_2$, 1.5 mM DTT, 5% glycerol. After incubation at RT for 30 mM, samples were run at 100V on a pre-electrophoresed 6% polyacrylamide gel containing 0.5×TBE for 1 h in ice water bath. Gel was stained by SYBR Green solution (Life Technologies, Grand Island, N.Y.) for 20 mM at RT. Then stained gel was rinsed with water for three times and visualized by EpiChemi II Darkroom (UVP, Upland, Calif.)

Lentivirus Production, Stereotaxic Injection and Cyrosection

Lenti-X 293T cells (Clontech, Mountain View, Calif.) were transfected with bicistronic lentiviral construct and two helper plasmids: PCMV-dR8.2 and PCMV-VSVG at 6 μg, 4.5 μg, and 1.5 μg of DNA per 10 cm plate using PerFectin (Genlantis, San Diego, Calif.). 48 h after transfection, culture medium was centrifuged at 780 g for 30 min and filtered at a 0.45 μm pore size. Filtered medium were further laid on the top of 20% sucrose followed by centrifugation in Beckman SW-28 rotor at 90,000 g for 2 h. The pellet was collected and resuspended in PBS or saline. For virus injection, mice were anesthetized using avertin (250 mg/kg) and placed in a stereotactic frame. A small incision was made to expose the skull surface. Holes were drilled in the skull overlying the motor cortex region (AP/Anterior-Posterior: 1 mm; ML/Medial-Lateral: 1 mm). The needle filled with virus was lowered down 0.7 mm (DV/Dorsal-Ventral) and 2 μl virus (109 viral particles/ml) was injected in 5 min. The needle was left in place 5 min before slow withdraw. Skin was sutured and mice were allowed for recovering on warm pads. One week after injection, mice were deeply anesthetized with avertin and transcardially perfused with cold PBS. The brain was fixed in paraformaldehyde (4%) for 24 h and then in 30% sucrose for 24 h again. After cryoprotection, the brain coronal sections were cut in 20 μm thickness for immunostaining.

In Vivo Administration of TAT-Peptide

Mice surgery/procedures were performed according to the NIH guidelines and were approved by the Institutional Animal Care and Use Committee (IACUC) at Case Western Reserve University. C57BL/6 non-transgenic wild type mice (NTG mice), Prnp-TARDBP mice (TDP-43 WT Tg mice) and Prnp-TARDBP*A315T mice (TDP-43 A315T Tg mice) were purchased from the Jackson Laboratory (Bar Harbor, Me.). Mice were infused subcutaneously with mini-osmotic pumps (Alzet Model 2004, Cupertino, Calif.; flow rate of 0.25 μl/hour). One day before implantation, mini-osmotic pumps were filled with 200 μl PBS containing cPM or PM1 peptides (0.5 mg/kg/Day) followed by pump incubation in PBS at 37 overnight according to the manufacturer's instructions. For surgery, male mice were anesthetized with avertin. A small incision was made at the back of mouse and mini-osmotic pump were implanted subcutaneously. After treatment, mice were deeply anesthetized with avertin and transcardially perfused with cold PBS and spinal cord and brain tissues were collected followed by fractionation, western blot or immunostaining.

Motor Behavioral Assessment

The Rotarod test was used to assay motor coordination and balance of mice using Panlab RotaRods (Harvard Apparatus, Holliston, Mass.). Taken briefly, mice first received training with 3 trials a day for 3 days (4-12 rpm for less than 3 minutes with at least 10 minute intervals between trials). All mice used in this study reached a stable Rotarod performance after training (data not shown). Three days after training, mice were assayed at the accelerating mode (4-40 rpm over 5 minutes) for three times every week. All Rotarod tests were performed with at least 5 minutes intervals for different genotypes and interspersed to avoid habituation. Footprint analyses were performed using a customized runway with 50 cm long, 5 cm wide and both sides bordered. The forepaw and hindpaw of mice were first dipped into red and blue non-toxic paints. Subsequently, mice were placed on the runway covered by white paper and ran into an enclosed dark box. Footprints of sitting mice were not included in quantification. Stride length is the mean distance of forward movement between each stride, while base length is the mean distance between left and right forepaw or hindpaw.

Confocal Microscopy, Fluorescent Microscopy and Electron Microscopy

All confocal images were captured at RT with a Zeiss LSM 510 inverted laser-scanning confocal fluorescence microscope (controlled through Zeiss LSM 510 confocal software, Zeiss) equipped with a C-Apochromat 40×/1.2 W water objective or alpha Plan-Fluar 100×/1.45 oil objective as previously described _ENREF_3771. Confocal images of far-red fluorescence were collected using 633 nm excitation light from a HeNe laser and a 650 nm long-pass filter; images of red fluorescence were collected using 543 nm excitation light from an argon laser and a 560 nm long-pass filter; and green fluorescence images were collected using 488 nm excitation light from an argon laser and a 500-550 nm bandpass barrier filter.

For time-lapse imaging or regular fluorescence imaging of TMRM, Rhod123 and SYTOX green, cells or neurons were seeded in 35 mm dishes or 24 well plates, and infected/transfected with mito-DsRed2 or indicated plasmids. Cells or neurons were imaged by an inverted Leica DMI6000 fluorescence microscope (Leica) (controlled through Leica LAS AF 3 software) with a 20×/0.7NA Plan Apochromat dry objective and well-equipped with environmental chamber with controlled CO2 content, humidity and temperature (37° C.). Images were captured with lowest intensity to avoid photobleaching or signal oversaturation. During time-lapse imaging, frames were captured every 10 s for at least 1 h without phototoxicity or photobleaching. For immuno-EM, biopsied human brain tissue, cells and isolated mitochondria were fixed in 4% w/v formaldehyde containing 0.1% w/v glutaraldehyde in 0.1 M HEPES buffer (Electron Microscopy Sciences, Hatfield, Pa.) at RT for 45 min, then dehydrated in ethanol and embedded in LR White resin (Poly-sciences, Inc., Warrington, Pa.) Immuno-gold labeling procedure was performed according to the method described by Fujioka et al. Thin sections were blocked with PBS containing 1% w/v bovine serum albumin (BSA), 1% v/v normal goat serum and 0.01% v/v Tween 20 (PBGT). Grids were then incubated with antibodies (anti-Flag or anit-TDP-43) at 1:10~1:30 dilution in PBGT for 12 h at 4° C. Negative controls included normal rabbit serum, normal mouse serum, and PBT replaced as the primary antibody. After washing, grids were incubated for 1.5 h in 10 nm gold-conjugated goat anti-rabbit IgG or goat anti-mouse IgG (British BioCell International, Ted Pella, Inc., Redding, Calif.) diluted 1:20 in PBGT, rinsed with PBS, and fixed with glutaraldehyde to stabilize the gold particles. Gold-labelled thin sections were stained first with 2% acidified uranyl acetate at 38° C. for 30 min, then with the triple lead stain of Sato as modified by Hanaichi et al., then examined in an FEI Tecnai Spirit (T12) with a Gatan US4000 4k×4k CCD. For regular EM, samples were freshly dissected and processed for transmission electron microscopy as previously describes: Small pieces of the tissue or isolated mitochondria were fixed by immersion in triple aldehyde-DMSO. After rinsing in distilled water, they were postfixed in ferrocyanide-reduced osmium tetroxide. Another water rinse was followed by an overnight soak in acidified uranyl acetate. After again rinsing in distilled water, the tissue blocks were dehydrated in ascending concentrations of ethanol, passed through propylene oxide, and embedded in Poly/Bed resin. Thin sections were sequentially stained with acidified uranyl acetate followed by a modification of Sato's triple lead stain and examined in an examined in an FEI Tecnai Spirit (T12) with a Gatan US4000 4k×4k CCD.

Image Analysis

Image analysis was also performed with open-source image analysis programs WCIF ImageJ (developed by W. Rasband). 3D images were reconstructed using "3D Viewer" plugin. Line scan analysis were performed using "RGB Profiler Plot" plugin. Taken briefly, raw confocal images were background corrected. A straight line with "2" width was draw in regions of interest. Then the line were directly analyzed by choosing ImageJ plugin Graphics's "RGB Profiler Plot" under the "Plugins" menu. In the output of "RGB Profiler", data was exported into Microsoft Excel. The length of line was plotted on the x-axis, while the intensity was plotted on the y-axis. Kymograph and quantification of mitochondrial movement were performed using "MultipleKymograph" as described (http://www.embl.de/eamnet/html/body_kymograph.html). Mitochondria morphology in fibroblasts and HEK293 cells was quantified. Taken briefly, single plane or series of z-stacks of raw images were background corrected, linearly contrast optimized, applied with a 7×7 'top hat' filter, subjected to a 3×3 median filter and then thresholded to generate binary images. Most mitochondria were well separated in binary images and large clusters of mitochondria were excluded automatically. All binary images were further analyzed by Image J. Mitochondrial morphology in neurons or EM micrographs were all directly analyzed by image J.

Statistical Analysis

Statistical analysis was done with one-way analysis of variance (ANOVA) followed by Tukey's 870 multiple comparison test or student-t-test. Data are means±s.e.m. n represents number of 871 neurons, cells or mice per experiment. $p<0.05$ was considered to be statistically significant. ns, not significant. All statistical analyses were performed in a blinded fashion.

Results

TDP-43 Accumulates in Mitochondria in ALS and FTD

We first investigated the co-localization of TDP-43 with various cellular organelles in neurons in human tissue samples of spinal cord from cases of ALS and age-matched normal individuals as well as frontal cortex from cases of FTD and age-matched normal individuals. Both spinal cord motor neurons and cortical neurons in the control cases demonstrated mainly nuclear TDP-43 localization, yet both ALS motor neurons and FTD cortical neurons showed characteristic 4 increased cytoplasmic TDP-43 accumulation (FIG. 1A-D). Notably, cytoplasmic TDP-43 in many spinal cord motor neurons of ALS patients and/or cortical neurons of FTD patients significantly co-localized with mitochondrial markers in similar distribution pattern (FIGS. 1A-D), but minimally overlapped with markers of Golgi, endoplasmic reticulum, lysosome, autophagosome, endosome or peroxisome. Despite low abundance, cytoplasmic TDP-43 in control human motor neurons and cortical neurons also significantly co-localized with mitochondria (FIG. 1A-D).

We further isolated highly purified mitochondria with preserved membranes from human spinal cord and cortical tissues, and found TDP-43 present in mitochondria from all samples (FIGS. 1E, F). As expected, there was a markedly higher expression of TDP-43 in mitochondria from ALS or FTD than from age-matched controls. Subsequent sub-mitochondrial fractionation analysis of these purified mitochondria revealed that mitochondrial TDP-43 was exclusively present in the inner mitochondrial membrane (IMM) fraction but not in outer mitochondrial membrane (OMM), intermembrane-space (IMS) or matrix (FIGS. 1G, H). Consistently, further immuno-electron microscopy (immuno-EM) analysis of purified mitochondria as well as biopsied human cortex confirmed the mainly localization of TDP-43 in IMM cristae (FIG. 1I). Isolated mitochondria from ALS spinal cords or FTD cortices exhibited more TDP-43 labeling than those from age-matched controls, which was expected. The inevitable post-mortem delay affects the integrity of human tissues, making further biochemical characterization of TDP-43 in IMM difficult. As a complementary approach, we obtained mitochondria from freshly collected mouse tissue samples of spinal cord and cortex, and treated them with trypsin and digitonin to permeabilize OMM but not IMM. OMM-proteins Mfn2/Mff were digested by trypsin alone, IMS facing IMM proteins Tim23/OPA1 were digested by trypsin after OMM permeabilization, while TDP-43 or matrix facing IMM proteins COXIV/F1β remained unchanged under all these conditions. Like COXIV/F1β, TDP-43 could be digested by trypsin after complete membrane permeabilization via triton X-100. As TDP-43 also exclusively resides in IMM fraction of mouse mitochondria, these results suggest that TDP-43 is located in the matrix-facing leaflet of IMM.

ALS-Associated Mutations Increase TDP-43 Mitochondrial Localization

We then determined whether disease-associated mutations in TDP-43 affected its mitochondrial localization. To exclude potential side effects related to overexpression and also make our findings directly relevant to patients, we first examined TDP-43 expression in mitochondria isolated from primary human fibroblasts derived from ALS patients bearing TDP-43 mutation G298S or A382T (G298S or A382T fibroblasts) and age-matched normal human individuals (normal human fibroblasts, NHFs). TDP-43 mutations in G298S and A382T fibroblasts were confirmed by genomic DNA sequencing. No TDP-43 mis-localization was observed in G298S and A382T fibroblasts. Whereas all fibroblasts bearing TDP-43 mutations displayed comparable expression of total TDP-43, G298S and A382T fibroblasts demonstrated significantly higher levels of mitochondrial TDP-43 than NHFs (FIG. 2A), suggesting increased TDP-43 mitochondrial localization by disease-associated mutations. To substantiate these findings, we compared WT and mutant TDP-43 mitochondrial localization in cultured HEK293 cells or mouse tissue samples of brain and spinal cord from hemizygous transgenic mice overexpressing WT or mutant human TDP-43. Consistently, despite similar expression levels in total lysates, exogenously expressed human TDP-43 G298S, A315T or A382T showed consistently increased expression in mitochondria than human WT TDP-43 (FIG. 2B, C, mitochondrial TDP-43 expression was adjusted by total TDP-43 and mitochondrial marker COXIV). Exogenously expressed or endogenous human WT and mutant TDP-43 were still present in IMM fraction (FIG. 2D, E) and digestible by trypsin after IMM but not OMM permeabilization (data not shown), indicating that disease-associated mutations had no effect on the sub-mitochondrial localization of TDP-43.

To exclude the possible interference of nuclear TDP-43, we further sought to confirm these findings in cell-free mitochondrial import assay using Flag-tagged recombinant WT/mutant human TDP-43 protein (rTDP-43) and isolated mitochondria from mouse brain. All human rTDP-43 were soluble, uncleaved and unmodified post-translationally (data not shown). The widely used biotin-labeled recombinant F113 precursor protein (pF1β) was included as a positive control, while recombinant GFP was employed as a negative control (data not shown). pF1β contained a cleavable signal sequence which was cleaved off after import to generate the shorter mF1β (FIG. 2F, right panel), indicating the intact import machinery in isolated mitochondria. Similar to mF1β, WT rTDP-43 survived digitonin/trypsin co-treatment after import (FIG. 2F, left panel), demonstrating the successful import to the innards of IMM in vitro. As expected, compared with WT rTDP-43, rTDP-43 bearing G298S, A315T or A382T, demonstrated increased import efficiency (FIG. 2G). WT/mutant rTDP-43 imported inside could be completely digested by trypsin after triton X-100 permeabilization (data not shown). Further immuno-EM analysis confirmed the mainly IMM cristae localization of imported WT/mutant rTDP-43 and the increased rTDP-43 import by disease-associated mutation (FIG. 2H). Together, these observations indicate that ALS-mutations increase TDP-43 mitochondrial localization.

TDP-43 Mitochondrial Localization Depends on Internal Motifs

Mitochondrial proteins are guided to mitochondria by either cleavable pre-sequences or noncleavable internal signals. TDP-43 remains uncleaved after import and no cleavable presequence is identified in TDP-43 by TargetPor Mitoprot, suggesting TDP-43 might use internal signals. Mitochondrial internal signals are typically composed of a stretch of continuous hydrophobic amino acids, and six such stretches are present in TDP-43 (FIG. 3A, M1-6). The deletions of M1/3/5 (ΔM1/3/5) significantly inhibited rTDP-43 import in vitro, and reduced mitochondrial localization of exogenously expressed TDP-43 (FIGS. 3B, C). Since M1 and M3 segments were conserved across species, we then synthesized two peptides PM1 (YGRKKRRQRRRAQFP-GACGL (SEQ ID NO: 15)) and PM3 (YGRKKRRQRRR-SKGFGFVRF (SEQ ID NO: 16)) in which M1 or M3 motif was fused to TAT peptide (YGRKKRRQRRR (SEQ ID NO: 11)) to enhance permeability. PM1 and PM3, but not control peptides cPMs (mixture of YGRKKRRQRRR-RAAQGFGCPL (SEQ ID NO: 18) and YGRKKRRQRRR-GRFFKSFG (SEQ ID NO: 19), scrambled M1 and M3 fused to TAT respectively), substantially suppressed rTDP-43 import, and decreased mitochondrial TDP-43 in HEK293 cells and primary neurons (FIG. 3D-F). The fusion of M3 and M5 especially M1 with the unrelated cytosolic protein GFP (green fluorescent protein) was sufficient to facilitate its mitochondrial targeting (FIG. 3G). On the basis of additional facts that M1, M3 or M5 deletion has no effect on the expression of nuclear, cytosolic and total TDP-43 (FIG. 3C), that M1, M3 or M5 deletion does not cause TDP-43 aggregation/mis-localization/cleavage (data not shown), and that PM1 or PM3 has no effect on pF1β import (FIG. 3D), we conclude that Ml, M3 and M5 are 208 critical internal motifs for TDP-43 mitochondrial localization.

Figure 4A:
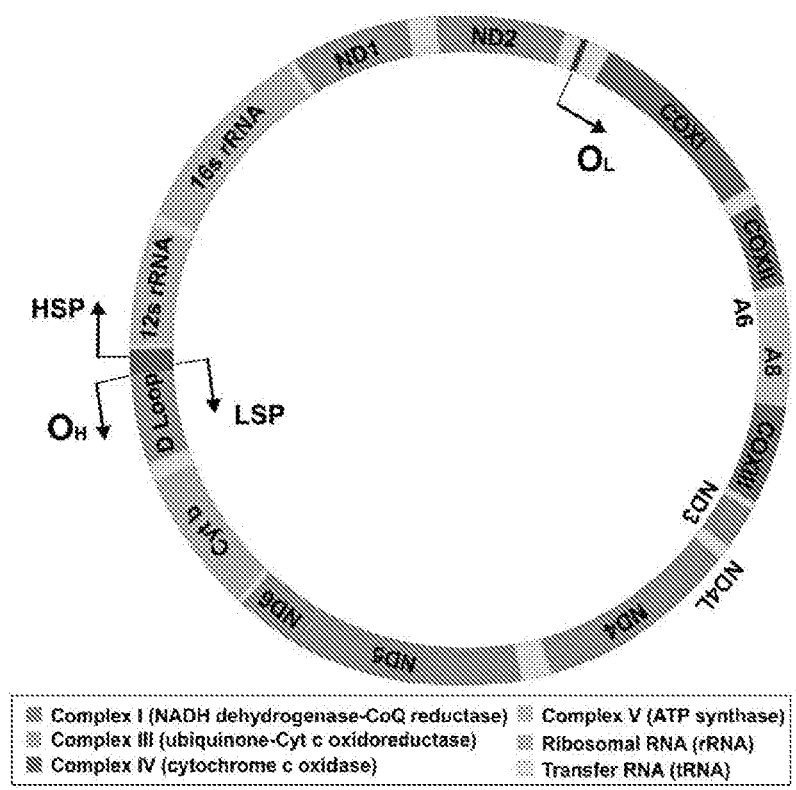
FIGS. 4(A-H) illustrates that TDP-43 preferentially binds mitochondria-transcribed mRNAs encoding complex I subunit ND3/6 and inhibits their translation. (A) Map of the human mitochondrial genome. The origins of light (OL)/heavy strand (OH) replication, light and heavy strand promoters (LSP and HSP), and the direction of DNA replication/transcription are indicated by arrows. Mitochondrial genome encodes 2 rRNAs and 22 tRNAs between coding genes, and 13 subunits essential for 4 oxidative phosphorylation (OXPHOS) complexes, i.e., complex I, III, IV and V. These 13 mitochondrial encoded proteins include 7 subunits of complex I (ND1, 2, 3, 4, 4L, 5 and 6), 1 subunit of complex III (Cyt b), 3 subunits of complex IV (COXI, II and III) and 2 subunits of complex V (A6 and A8). (B-D) Representative reverse transcriptase-coupled quantitative real time polymerase chain reaction (qRT-PCR) analysis of mitochondrial encoded mRNAs precipitated by antibodies specific to TDP-43 or Flag in purified mitochondria isolated from freshly collected mouse brain from 3 month old mice (B), cultured primary human fibroblasts (C) or HEK293 cells overexpressing Flag tagged WT or mutant human TDP-43 (D). Mitochondria from HEK293 cells were isolated two days after transient transfection with indicated constructs. All immunoprecipitation (IP) were performed with antibodies covalently coupled to magnetic beads followed by RNA extraction and purification. (E) Representative immunoblot and quantification of mitochondrial encoded protein translation in HEK293 cells. HEK293 cells were transfected with constructs encoding TDP-43 WT or ΔM1. Two days after transfection, cells were metabolically labelled with AHA (50 μM) in the presence of emetine (0.1 mg/ml). Following mitochondrial purification, AHA labelled proteins were tagged with biotin-alkyne and finally analyzed by immunoblot using streptavidin conjugates. The ND3 and ND6 bands in immunoblot were confirmed by specific antibodies (not shown). (F-H) Representative immunoblot and quantification of the expression of mitochondrial encoded proteins in HEK293 cells expressing Flag tagged WT or mutant human TDP-43 (F), primary human patient fibroblasts treated with 1 μM cPM (scrambled M1) or PM1 for 48 hours (G), and human tissue samples of spinal cord from cases of ALS (n=8) and age-matched normal individuals (n=6) (h). HEK293 cells were also transiently transfected two days before sample collection. Equal amount of 10 μg proteins were loaded. Data are means±s.e.m of triplicate experiments. Statistics: one-way analysis of variance (ANOVA) followed by Tukey's multiple comparison test. $*P<0.05$, $P<0.01$ and $*P<0.001$. In panel f, $*P<0.05$. In panel a and b, $*P<0.05$, $P<0.01$ and $*P<0.001$.

WT/Mutant TDP-43 in Mitochondria Preferentially Bind Mitochondrial-Transcribed ND3/6 mRNAs and Inhibit Their Translation TDP-43 primarily binds mRNA. The IMM residence of TDP-43 promoted us to examine whether TDP-43 bound mitochondria-transcribed mRNAs (FIG. 4A). RNA immunoprecipitation (IP) with or without prior cross-linking using mouse brain mitochondria found that, TDP-43 but not the RNA-binding-domain lacking negative control COXIV (not shown) significantly pulled down ND3, ND5, ND6, COXI, COXIII, Cyt b and A6 mRNAs, while other mRNAs were only slightly enriched, at levels comparable to 12 s or 16 s rRNAs (FIG. 4B). To investigate whether ALS mutations altered TDP-43 binding to its targets, we isolated mitochondria from G298S/A382T fibroblasts or HEK293 cells expressing human TDP-43 G298S, A315T or A382T. Surprisingly, all mutant TDP-43 precipitated similar mRNAs with comparable abundance as WT TDP-43 (FIGS. 4C, D).

Mitochondria-transcribed mRNA levels are not affected by TDP-43, suggesting the unlikely involvement of TDP-43 in mitochondrial transcription. Due to their high transfection efficiency and simple cultivation suitable for mitochondrial isolation and downstream biochemical analysis, we then investigated the effect of TDP-43 on mitochondrial translation in HEK293 cells by the azidohomoalanine (AHA) incorporation assay in the presence of emetine to block cytosolic translation. The synthesis of ND3 and ND6 was most significantly reduced by WT TDP-43 overexpression (FIG. 4E), consistent with the most preferential binding of TDP-43 to their mRNAs. The steady state levels of ND3 and ND6 but not most mitochondrial-encoded subunits of oxidative phosphorylation (OXPHOS) complexes were indeed decreased by WT TDP-43 (FIG. 4F), and WT TDP-43-induced reduction in the synthesis or expression of ND3 and ND6 could be blocked by M1 deletion. In an attempt to explore how mitochondrial TDP-43 regulated ND3 and ND6 translation, we investigated mitochondrial ribosome assembly and loading onto ND3 and ND6 mRNAs by sucrose gradient centrifugation of mitochondria isolated from HEK293 cells expressing TDP-43 WT or ΔM1. TDP-43 has no global effect on all mitochondria-encoded protein translation (FIGS. 4E, F). Not surprisingly, the sedimentation patterns of MRPS18B and MRPL44 (mitochondrial ribosome 28S/39S subunit marker) in sucrose gradients were similar in all samples, suggesting unchanged overall mitochondrial ribosome assembly. However, further RNA distribution analysis found that, in contrast to the mostly sedimentation with 55S ribosomal complex in control cells, ND3 and ND6 but not COXI mRNA demonstrated additional peaks between 28S and 55S complex after TDP-43 WT but not ΔM1 overexpression, indicating misloading of ribosome onto ND3 and ND6 mRNAs.

Figure 4H:
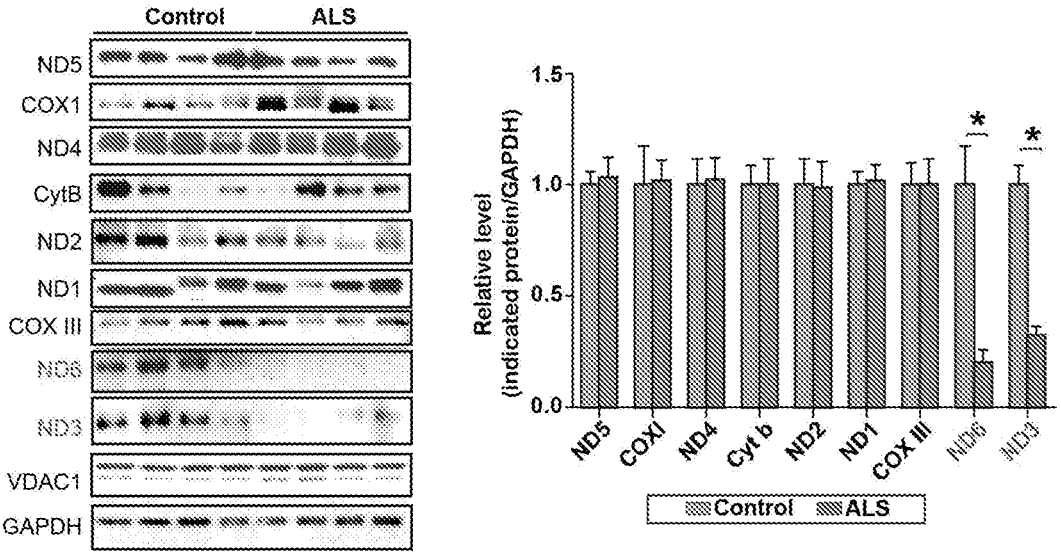

To investigate the effect of mutant TDP-43 on ND3 and ND6 expression, we examined HEK293 cells expressing TDP-43 G298S, A315T or A382T and human G298S or A382T fibroblasts. Compared with WT TDP-43, all mutant TDP-43 caused further reduced or reduced expression of ND3 and ND6 (FIG. 4F, G). Notably, the deletion of M1 or treatment with PM1 increased ND3 and ND6 expression to levels similar to control cells or NHFs. In this study, PM3 was not tested because of the localization of M3 in the TDP-43 RNA binding motif (FIG. 3A) and the mild toxic effect of PM3 on cells (data not shown). Consistently, compared with human tissue samples from aged matched normal individuals, human tissue samples of spinal cord from cases of ALS or frontal cortex from cases of FTD exhibited reduced expression of ND3 and ND6 (FIG. 4H), thus further extending our findings to diseases.

Figure 5A:
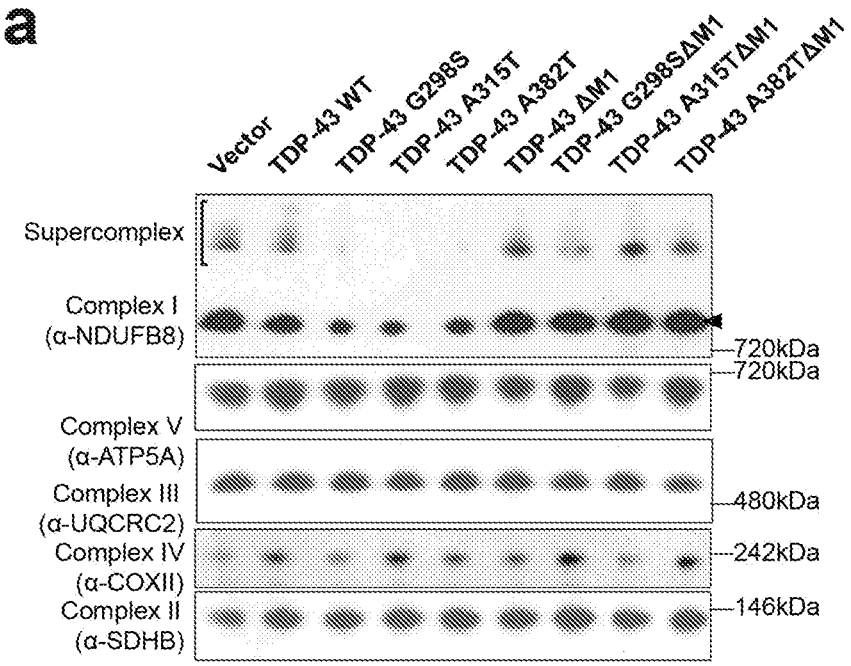
FIGS. 5(A-F) illustrate that TDP-43 specifically reduces complex I assembly and impairs mitochondrial function and morphology. (A, C) Representative images and quantification of OXPHOS complex I or I-V assembly in HEK293 cells overexpressing Flag tagged WT/mutant TDP-43 with/without M1 domain deletion (A), and cultured primary human fibroblasts 48 hours after 1 μM cPM (scrambled M1) or PM1 treatment (C). HEK293 cells were collected 48 hours after transient transfection Mitochondria were isolated from cells, lysed and analyzed by BN-PAGE/immunoblot using specific antibodies against subunits of each OXPHOS complex. Arrowheads point complex I. (B, D, E) Measurements of activities of OXPHOS complex I or II-V in isolated mitochondria from HEK293 cells overexpressing Flag tagged WT/mutant TDP-43 with/without M1 domain deletion (B), primary human fibroblasts 48 hours after 1 μM cPM (scrambled M1) or PM1 treatment (D), or HEK293 cells co-overexpressing Flag tagged WT TDP-43, ND3 and/or ND6 (E). HEK293 were transiently transfected with indicated constructs and mitochondria were isolated for enzyme activities 48 hours after transfection. (F) Bulk measurements of mitochondrial function including $m\Delta_\psi$, ATP production and oxygen consumption rate (OCR) in primary human fibroblasts 48 hours after 1 μM cPM (scrambled M1) or PM1 treatment. For $m\Delta_\psi$, fibroblasts cultured in 24 well plates were load with 20 nM TMRM for 30 min and analyzed by a fluorescence microplate reader. The ATP levels of fibroblasts were determined by ATP colorimetric/fluorometric assay kits and an absorbance microplate reader. OCR of live cultured fibroblasts with optimal seeding density (100,000 cells/well) was directly measured using the Seahorse XF24 Analyzer. All measurements in each sample were normalized by total protein. (G) Representative confocal images and quantification of mitochondrial length in primary human fibroblasts. One day before treatment with 1 μM cPM or PM1 for 48 hours, fibroblasts were transfected with constructs encoding mitoDsRed2 (a mitochondrial specifically localized red fluorescent protein) to label mitochondria. Nuclear was stained by DAPI as blue. n=50 cells for each group. (F) Measurement of the sensitivity of primary human fibroblasts to oxidative stress. Indicated primary human fibroblasts were cultured in 24 well plates and pre-treated with or without 1 μM cPM (scrambled M1) or PM1. 48 hours after pre-treatment, fibroblasts were treated with 50 μM H2O2 for 1 hour and examined by lactate dehydrogenase (LDH) assay after 3 hours of recovery (after replacing fresh medium without $H_2O_2$). The LDH release in the presence of 1% Triton X-100 was taken as 100% cell death ("100"). No obvious cell detachment was observed in either NHFs or patient fibroblasts under all conditions and LDH release in each sample was normalized by total protein. Data are means±s.e.m of triplicate experiments. Statistics: one-way analysis of variance (ANOVA) followed by Tukey's multiple comparison test. $*P<0.05$. In panel A and B, $*P<0.05$, compared with control cells and $\#p<0.05$, compared with cells expressing WT TDP-43.

WT/Mutant TDP-43 in Mitochondria Impair OXPHOS Complex I and Mitochondrial Bioenergetics Consistent with the specific inhibitory effect of TDP-43 on the expression of complex I subunit ND3 and ND6, HEK293 cells overexpressing WT TDP-43 showed the most significant loss and dysfunction of OXPHOS complex I as well as slight disassembly of complex I-comprised OXPHOS supercomplexes, the effect of which was significantly exacerbated by disease-associated mutations G298S, A315T or A382T but significantly prevented by M1 deletion (FIGS. 5A, B). As expected, the disassembly and dysfunction of OXPHOS complex I was capitulated in patient-derived G298S or A382T fibroblasts, and PM1 treatment significantly restored OXPHOS complex I assembly and function to levels comparable to NHFs (FIG. 5C, D). Interestingly, TDP-43-induced complex I disassembly and dysfunction could also be greatly alleviated by the simultaneous overexpression of both ND3 and ND6 but not ND3 or ND6 individually (FIG. 5E), further supporting both ND3 and ND6 as specific targets of TDP-43 in mitochondria.

Complex I is critical for OXPHOS27. As expected, significant mitochondrial dysfunction including reduced mitochondrial membrane potential ($m\Delta_\psi$), oxygen consumption rate (OCR) and ATP levels accompanied by mitochondrial fragmentation were all observed in HEK293 cells overexpressing WT or mutant TDP-43, and patient G298S or A382T fibroblasts (FIGS. 5F, G). Compared with WT TDP-43, mutant TDP-43 caused more sever mitochondrial abnormalities in HEK293 cells. Not surprisingly, WT and/or mutant TDP-43-induced mitochondrial dysfunction and fragmentation in HEK293 cells and human fibroblasts could be completely prevented by M1 deletion or PM1 treatment. Notably, although no basal cell death was observed, patient derived G298S or A382T fibroblasts exhibited significantly increased vulnerable to oxidative stress compared with NHFs, which could also be abolished by PM1 treatment (FIG. 5H). Suppression of TDP-43 mitochondrial localization blocks WT/mutant TDP-43 neuronal toxicity in vitro and in vivo. Finally, we attempted to determine whether TDP-43 mitochondrial localization contributed to its toxicity on neurons. Overexpression of WT TDP-43 resulted in mitochondrial fragmentation and dysfunction (reduced $m\Delta_\psi$/OCR/ATP) preceding neuronal death in in vitro cultured rat primary neurons, all of which were exacerbated by G298S, A315T or A382T but completely abolished by M1 deletion or PM1 treatment. To substantiate these findings, we reprogrammed NHFs and human A382T fibroblasts to induced-pluripotent stem cells (iPSCs) followed by sequentially differentiation into induced neuronal progenitor cells (iNPCs) and human neurons (control human neurons and A382T human neurons respectively. Control human neurons and A382T human neurons were indistinguishable in TDP-43 nuclear localization, neuronal morphology and viability. However, compared with control human neurons, A382T human neurons exhibited significant mitochondrial fragmentation/dysfunction and increased vulnerability to oxidative stress, which could be alleviated by PM1 treatment. As expected, similar to what was observed in rat primary neurons, overexpression of TDP-43 WT or A315T in iPSCs-derived control human neurons also caused mitochondrial abnormalities and neuronal death, and the deletion of M1 deletion was sufficient to abolish TDP-43 induced mitochondrial and neuronal toxicity.

To confirm our findings in vivo, we stereotactically injected neuron-specific bicistronic lentivirus encoding both TDP-43 and mitoDsRed2 into mouse cortices (FIG. 6A). Compared with WT TDP-43, TDP-43 A315T overexpression caused further fragmentation of mitochondria and increased number of cleaved caspase-3 positive neurons (reflecting neuronal death), which could be blocked by M1 deletion (FIG. 6B, C). Despite controversy over whether TDP-43 A315T transgenic mice develop ALS-like phenotypes, neurodegeneration and neuropathologies have been consistently reported in TDP-43 A315T hemizygous transgenic mice but not in TDP-43 WT hemizygous transgenic mice, even though they exhibited similar expression of human TDP-43 (FIG. 2C). We treated TDP-43 A315T mice with PM1 by continuous subcutaneous infusion and confirmed that PM1 reached the central nervous system and substantially reduced mutant TDP-43 in mitochondria. As TAT enables peptides to traverse across mitochondrial double membranes, PM1 could be detected in all mitochondrial compartments, which was expected. TDP-43 A315T mice demonstrated significantly reduced ND3 and ND6 expression, mitochondrial fragmentation and dysfunction (reduced $m\Delta_\psi$/OCR and complex I disassembly), motor neuron loss and axon degeneration, neuropathologies (inclusions and astrocyte activation), denervated neuromuscular junction (NMJ), gait abnormalities and impaired motor coordination/balance, all of which could be alleviated by PM1 and restored to levels comparable to non-transgenic (NTG) mice (FIGS. 6D-J). The deletion of M1 has no effect on TDP-43 half-life, dimerization or its binding to non-mitochondrial mRNA targets. Also, M1 is not located in any known functional domain (FIG. 3A). In addition, M1 deletion or PM1 treatment has no significant effect on cytosolic, nuclear or total TDP-43 (FIGS. 3C-F). Together, all these data suggest that mitochondrial localization is a critical determinant of WT and mutant TDP-43 toxicity on neurons.

Example 2

In this Example, we performed a battery of motorcoordinative and cognitive tests in adult hemizygous TDP- 43M337V Tg mice. Based on Example 1, which identified mitochondria as direct mediators for TDP-43 induced neurotoxicity, we further tested whether the inhibition of the mutant TDP-43 mitochondrial localization could reverse motor-coordinative and cognitive deficits in aged hemizygous TDP-43M337V Tg mice after disease onset.

Materials and Methods

Animals and Treatments

Mice surgery/procedures were performed according to the NIH guidelines and were approved by the Institutional Animal Care and Use Committee (IACUC) at Case Western Reserve University. C57BL/6 non-transgenic wild type C57BL/6 mice (NTG mice) and C57BL/6-Tg(Prnp-TARDBP*M337V)4Ptrca (hTDP-43M337V transgenic mice, Stock No. #017604) were purchased from the Jackson Laboratory (Bar Harbor, Me.) and maintained at Case Western Reserve University. All mice were weaned on postnatal day 30 and genotyped by PCR analysis of DNA extracted from punched ear. Detailed mouse age and gender information for each experiment is presented in specific figure legends. For peptide infusion, mini-osmotic pumps (Alzet Model 2006, Cupertino, Calif.; flow rate of 0.15 μl/hour) were filled with 200 μl PBS containing SC or PM1 peptides (0.5 mg/kg/Day) followed by pump incubation in PBS at 37° C. overnight according to the manufacturer's instructions. When mice were fully anesthetized with avertin, mini-osmotic pumps were implanted subcutaneously at the back of mouse. Six weeks after treatment, mice were transcardially perfused with ice cold PBS and brain and spinal cord tissues were collected.

Behavioral Tests

A series of behavioral tests to investigate the sensorimotor and cognitive performances were conducted in mice treated with/without peptide infusion. The results from two independent, but age-matched cohort groups were combined. The test battery consisted of motor task (open field test), body coordination task (rotarod and beam walking test), muscle strength (grip strength test), tactile sense task (sticky paper test), and memory task (Y-maze for working memory, T-maze for short-term spatial memory, object recognition for short-term and long-term non-spatial memory, and fear conditioning for emotional memory). Individual mice were tested for these behavioral tasks on each test day in the following order: Day 1 for rotarod and grip strength test; Day 2 for open field test, and beam walking test; Day 3 for Y-maze; Day 4-5 for sticky paper test and object recognition test; Day 6 for T-maze; and Day 7-8 for fear conditioning test. All tests were performed at the Case Behavior core, with the investigator blinded to both mouse genotype and treatment group.

Rotarod Test

Rota-Rods (Panlab/Harvard Apparatus, Holliston, Mass.) was used to measure motor coordination and balance. Each mouse first received 3 trials per day for 3 days. During the training period, each mouse was placed on the rotarod, where cylinder speed was gradually increased from 4 rpm to 12 rpm for each trial. On the testing day, rotarod was set to accelerating mode (4-40 rpm over 5 minutes) and maximal latency to fall off was collected for statistical analysis.

Grip Strength Test

Muscular strength of mouse was measured by GRIP STRENGTH TEST meter (Bioseb, Vitrolles, France). For forelimb test, two fore paws of mouse was placed on bar and mouse tail was pulled back. For hindlimb, two fore paws were placed on grid which was hold by examiner's left hand, and two hind paws of mouse was placed on bar which was connected machine. The single best recorded value was used for statistical analysis.

Open Field Test

The open field consisted of a 50 cm-long square plastic apparatus, closed with 50 cm high walls, and activity was recorded using ANY-maze video tracking software (Stoelting Co. Wood Dale, Ill.). The field was digitally divided into inner area (30 cm×30 cm) and peripheral (10 cm wide gallery) using ANYmaze software. Data were collected continually for 10 minutes and the distance traveled (m), velocity (m/second), time spent in immobile (more than 2 sec non-locomotion), and time spent in the inner area were all recorded and scored automatically.

Beam Walking Test

Motor coordination and balance of mice were assessed by measuring the ability of the mice to traverse a graded series of narrow beams to reach an enclosed safety platform. The beams consisted of long strips of wood (50 cm) with a 16-mm round diameter, or 16- or 9-mm square cross-section. During training, mice were placed at the start of the 16-mm-round beam and trained to traverse the beam to the enclosed box. Once the mice were trained (traversed the 16-mm-round beam in <20 sec) they received two consecutive trials on each of the beam in each case progressing from 16-mm-round beam, 16-mm-square beam, to 9-mm-square beam. Mice were allowed up to 60 sec to traverse each beam. The latency to traverse each beam and the number of times the fore and hind feet slipped off each beam were recorded for each trial.

Y-Maze Test

To investigate their short-term special memory, mice were placed in a plexiglass T-maze (with arms 60 cm of length) and were allowed to explore the maze freely for 8 min while one of the arms was blocked. The blocked arm was switched between animals to avoid any arm preference bias (counterbalanced). Following a 8-min exploration, mice were returned to their home cage for 2 h and then put back in the T-maze for 5-min, this time, with all three arms open. Once put in the T-maze, mice were recorded using ANY-maze tracking system, and the time and frequency in the previously blocked arm, and total numbers of arm entries were counted.

T-Maze Test

To investigate their short-term special memory, mice were placed in a plexiglass T-maze (with arms 60 cm of length) and were allowed to explore the maze freely for 10 min while one of the arms was blocked. The blocked arm was switched between animals to avoid any arm preference bias (counterbalanced). Following a 10-min exploration, mice were returned to their home cage for 2 h and then put back in the T-maze, this time, with all three arms open. Once put in the T-maze, mice were recorded using ANY-maze tracking system (Stoelting, Wood Dale, Ill.), and the time and frequency in the previously blocked arm, and total numbers of arm entries were counted by using video-scoring software.

Object Recognition Test

This task of recognition memory utilizes the fact that animals will spend more time exploring a novel object compared with an object that they are familiar with. The test apparatus was a regular housing cage with bedding material. Each mouse was placed in a regular housing cage for 3 min. Then two identical objects were placed at the corner of the housing cage (T1). Mice were allowed to investigate these objects for 5 min. This session was followed by a 1.5 hr delay during which the animals were returned to their home cages with their cagemates. After the delay the animals performed a 5-minute dissimilar stimuli session (T2, short-term memory). In this session, an object that was presented in T1 and another object that was unfamiliar were placed in the test cages. Then mice were returned to their home cages and twenty-four hour later, the third session was performed (T3, long-term memory). In this 5-min session, an object that was presented in T1 and T2 and another object that was unfamiliar were placed in the test cages. The objects were made of hard plastic and/or metal with apparently different shapes. The total amount of time spent to sniff and contact each object were recorded and scored using fully automated ANY-maze video tracking software. The total distance travel during 5 min and the duration of stay at the far side of the cage (immobile) were also measured.

Fear Conditioning Test

All animals were placed in a conditioning box (Med Associates, Burlington, Vt.) and trained to associate a tone (white noise, 80 dB for 30 s, conditioned stimulus (CS)) with electrical shock (0.5 mA for 1 s, unconditioned stimulus (US)). This procedure was repeated four times with 120 sec accumulation and 60 sec inter-stimulus-interval. A tone and shock was co-terminated. At the end of the trial, the animals were taken out and placed back in the box 24 h later to evaluate their learned aversion for an environment associated with the shock (context-dependent fear). To this end, all animals were placed in the same box in which they were trained for the duration of 6 min, and freezing behavior in the absence of tone or aversive stimulus were measured. The animals were then removed, and the context was changed so that the animals could no longer recognize the chamber in which they had been trained. Two hour after the animals were tested for contextual fear conditioning, they were reintroduced into the now contextually altered box (shape, lighting, and odor (vanilla essence)), and freezing behavior was measured during the first 2 min to verify that the animals did not recognize the context. After 2 mM (no-cue period), the tone (30 sec, 5 kHz, 80 dB) was delivered 10 times without US exposure in 60 sec ISI, and freezing behavior was measured to determine cue-dependent fear conditioning.

Mitochondria Isolation

Tissue was homogenized in IB-1 solution (225 mM mannitol, 75 mM sucrose, 0.1 mM EGTA, 20 mM HEPES, pH 7.4). Then homogenate was centrifuged at 600 g for 5 min to remove nuclear contaminants and unbroken cells. The supernatant was once again centrifuged at 600 g for 5 min, followed by a centrifugation at 7,000 g for 10 min. The supernatant was collected as the cytosolic fraction. The pellet was washed in IB-2 solution (225 mM mannitol, 75 mM sucrose, 20 mM HEPES, pH 7.4), centrifuged at 7,000 g for 10 min, resuspended in IB-2 solution, centrifuged at 10,000 g for 10 mM and finally resuspended in MRB buffer (250 mM mannitol, 5 mM HEPES, 0.5 mM EGTA, pH 7.4). The resuspended fraction was overlaid on top of 8 ml Percoll medium (225 mM mannitol, 25 mM HEPES pH 7.4, 1 mM EGTA and 30% Percoll (v/v)), followed by centrifugation at 95,000 g in a SW40 rotor for 30 mM at 4° C. The purified mitochondrial fraction was collected and resuspended in 10 fold volume of MRB buffer and centrifuged 10 mM at 6,300 g to collect pellet as mitochondria fraction.

Synaptosome Isolation and Mitochondria Respiration Assay

Synaptosomes were isolated from mouse cortices as previously reported. Briefly, cortex tissue was rapidly removed and homogenized in ice cold 'Sucrose Medium' (320 mM sucrose, 1 mM EDTA, 0.25 mM dithiothreitol, pH 7.4. The homogenate was then centrifuged at 1000 g for 10 mM at 4° C. The supernatant was carefully layered on top of a discontinuous Percoll gradient (3 mL layers of 3, 10, and 23% Percoll in sucrose medium) in centrifuge tube and centrifuged at 32,500 g for 10 mM at 4° C. Synaptosomes were collected as the band between 10% and 23% Percoll. The collected solution was diluted into 'Ionic Medium' (20 mM HEPES, 10 mM D-glucose, 1.2 mM $Na_2HPO_4$, 1 mM $MgCl_2$, 5 mM $NaHCO_3$, 5 mM KCl, 140 mM NaCl, pH. 7.4). After centrifuged at 15,000 g for 15 mM at 4° C. to remove Percoll, pellets were resuspended in ionic media. The cell culture plates were coated with polyethyleneimine (1:15000 dilution from a 50% solution, Sigma-Aldrich) overnight and washed with distilled water. The synaptosomes were attached to plates by centrifuged at 3,000 g at 4° C. for 30 min and were placed on ice for further measurement. The mitochondria respiration assay protocol consisted of repeated cycles of 3 minute mixing, 2 minute wait and 3 minute measurement periods. Basal oxygen consumption rate (OCR) was measured 3 times by Seahorse XF-24 (Seahorse Bioscience, Billerica, USA). Protein concentrations for each well were measured to confirm the similar amount of synaptosomes.

Immunoblot, Immunocytochemistry and Immunofluorescent Analysis

Tissues or cellular fraction were homogenized or lysed in RIPA buffer (Abcam, Cambridge, Mass.) with 1X protease inhibitor cocktail (Cell signaling, Danvers, Mass.). Proteins were separated by 10% SDS PAGE and transferred to PVDF membrane. Following incubation with primary antibody overnight in cold room and secondary antibodies at room temperature for 1 hour, immunoreactivity were detected by ECL (Millipore Immobilon). Rabbit TDP-43 antibody (Proteintech, Rosemont, Ill.), mouse human TDP-43 antibody (Abnova, Walnut, Calif.), COX VI (Abcam, Cambridge, Mass.), and GAPDH/Calnexin (Cell signaling, Danvers, Mass.) Immunocytochemistry was performed by the peroxidase anti-peroxidase protocol. For immunofluorescent staining, deparaffinized and re-hydrated tissue sections without $H_2O_2$ treatment were washed briefly three times with distilled $H_2O$ and placed in 1× antigen decloaker (Biocare, Concord, Calif.). The sections were then subject to antigen retrieval under pressure using Biocare's Decloaking Chamber by heating to 125° C. for 10 sec and cooling to 90° C. for 30 sec followed by heating to 22 psi at 128° C., and cooling to 0 psi at 94° C. After temperature decreased to 30° C., the sections were gradually rinsed with distilled $H_2O$ for five times. The sections were then blocked with 10% normal goat serum (NGS) for 30 min at RT, and incubated with primary antibodies in PBS containing 1% NGS overnight at 4° C. After 3 washes with PBS, the sections were incubated in 10% NGS for 10 min, and then with Alexa Fluor conjugated secondary antibody (Life Technologies, Grand Island, N.Y.) (1:300) for 2 h at RT in dark. Finally, the sections were rinsed three times with PBS, stained with DAPI, washed again with PBS for three times, and mounted with Fluoromount-G mounting medium (Southern Biotech, Birmingham, Ala.).

Results

Alterations in Motor Coordination but not Locomotive Activity, Muscle Strength or Sensorimotor Function in Adult Hemizygous TDP-43M337V Mice We first monitored hemizygous TDP-43M337V mice by body weight and commonly used behavioral tests relevant to motor and coordination function: rotarod and beam-walk tests. Hemizygous TDP-43M337V mice were viable and phenotypically normal at birth, and demonstrated no difference from wild-type (WT) littermates in feeding, body weight, survival and hindlimb clasping until 16 month old (currently the oldest available mice, data not shown). However, at 8 month old, they exhibited significant impairments in the performance on rotarod and beam-walking tests manifested by the decreased ability to stay on the rotarod and longer traverse latencies on beams ($F1,27=8.12$, $P<0.01$ for rotarod; $F1,27=11.86$, $P<0.01$ for 12 mm square beam; $F1,27=1.21$, nonsignificant for 12 mm round beam; $F1,27=5.48$, $P<0.05$ for 9 mm square beam; FIG. 7A, B). No difference in the rotarod and beam-walk test was seen between male and female mice. The impaired rotarod and beam-walking performance was unlikely caused by muscle weakness as all mice performed similarly in the grip strength test for both fore- and hind-limbs ($F1,27=0.69$ for forelimb and 0.38 for hindlimb, nonsignificant; FIG. 7C).

To further investigate whether the locomotor activity was altered, we assessed open field activity of transgenic mice. Compared with WT mice, 8-9 month old hemizygous TDP-43M337V mice showed a nonsignificant trend for greater traveling distance and faster moving speed in the open field test ($F1,27=3.55$, $P<0.10$ for distance; $F1,27=3.50$, $P<0.10$ for speed; FIG. 7D). No difference in time spent in the inner area was noted ($F1,27=0.05$, nonsignificant; data not shown), indicating unchanged anxiety-related behavior. We also measured tactile sensory responses in hemizygous TDP-43M337V mice by the sticky paper test. The expression of TDP-43M337V did not significantly affect the time for mice to make contact and remove adhesive tapes ($F1,27=0.02$, nonsignificant; FIG. 7E), suggesting that the paw sensorimotor function was not altered.

Cognitive Deficits in Adult TDP-43M337V Tg Mice

Both beam-walking and especially rotarod tests used to evaluate motor coordination may also be especially sensitive to brain dysfunction. Therefore, the finding of impaired rotarod and beamwalking performance in hemizygous TDP-43M337V mice, without deficits in locomotive activity, muscle strength or sensorimotor function, might reflect behavioral alterations stemming from cognitive deficit in the brain. To test this hypothesis, we conducted a series of behavioral tests to investigate the cognitive performance in 8-9 month old hemizygous TDP-43$^{M337V}$ mice. The test battery consisted of Y-maze test for spatial working memory, T-maze test for short-term spatial memory, object recognition test for shortterm and long-term non-spatial memory, and fear conditioning test for emotional memory. In the Ymaze test based on the natural tendency of mice to alternate arms when exploring a novel environment, all mice exhibited good ambulatory activity with similar exploration rates (data not shown). However, transgenic mice showed a significantly lower ratio of spontaneous alternations than WT mice ($F1,27=8.92$, $p<0.01$, FIG. 8A), suggesting impaired spatial working memory. To further assess spatial memory deficits in hemizygous TDP-43$^{M337V}$ mice, we performed T-maze test also based on the innate preference of mice to explore unfamiliar environment relevant to visited arms. After the acclimation period, consistent with the Y-maze test, transgenic mice performed significantly worse than age matched WT mice ($F1,27=4.47$, $p<0.05$; FIG. 8B).

In the object recognition test utilizing the fact that animals will spend more time exploring a novel object compared with an object that they are familiar with, no significant difference in the total amount of time spent to sniff and contact each object was evident during the first probe trial (T1, 50% chance level) for either group of mice ($F1,27=0.97$, nonsignificant FIG. 8C). However, during the second dissimilar stimuli session (T2, short-term memory) and the third session at twenty-four hour post T2 (T3, longterm memory), hemizygous TDP-43$^{M337V}$ mice investigated unfamiliar objects significantly less than WT mice ($F1,27=22.73$, $p<0.01$ for T2; $F1,27=10.98$, $p<0.01$ for T3; FIG. 8C), revealing impaired both shortterm and long-term non-spatial memory.

In the fear conditioning test based on mice learning to associate a neutral tone conditional stimulus (CS) with a mild electrical foot unconditional stimulus (US) and show freezing response, we did not detect any significant difference between WT and transgenic mice in the proportion of time spent freezing during habituation and first three US exposures in the training session ($F1,27=0.09$ for habituation session; $F1,27=0.003$ for 1st US; $F1,27=2.85$ for 2nd US; and $F1,27=1.83$ for 3rd US; all nonsignificant; FIG. 8D). Interestingly, in the 4th US exposure, hemizygous TDP-43M337V mice showed significantly lower freezing times compared with WT mice ($F1,27=6.99$, $p<0.05$). The reduced fear response was 6 indeed maintained in the test session 24 h later to evaluate their learned aversion for an environment associated with the shock (context-dependent fear; $F1,27=4.94$, $p<0.05$). Cohorts of mice were also reintroduced into the contextually altered box (shape, lighting, and odor (vanilla essence)) for cuedependent fear conditioning test. Neither WT nor transgenic mice could recognize the context before adding CS ($F1,27=2.44$, nonsignificant). As expected, CS elicited freezing responses were significantly lower in hemizygous TDP-43M337V mice than WT mice ($F1,27=7.59$, $p<0.05$). During extinction training with 10 times CS exposure, both WT and transgenic mice displayed similar weak extinction (data not shown). In this study, no significance difference in the cognitive performance between male and female mice was noted. In sum, our results show that, in addition to impaired motor and coordination function, adult hemizygous TDP-43M337V mice also develop deficits in memory.

The Inhibition of TDP-43 Mitochondrial Localization by PM1 Alleviates Cytoplasmic TDP-43 Accumulation, Mitochondrial Dysfunction and Neuronal Loss in the Brains of TDP-43M337V Tg Mice We previously characterized the specific amino acid motif that confers TDP43 mitochondrial localization. The suppression of TDP-43 mitochondrial localization by either the deletion of motif M1 (AQFPGACGL) (SEQ ID NO: 4) essential for its mitochondrial localization, or treatment with the M1 motif based inhibitory peptide PM1 could block WT or mutant TDP-43 induced mitochondrial dysfunction and neuronal death in vitro and in mice. Here, 11-12 month old WT and transgenic mice were continuously infused with PM1 or control peptide (cPM) for 6 weeks (1.5 mg/kg/day; subcutaneously implanted ALZET pumps). Consistent with our previous study, murine TDP-43 (mTDP-43, recognized by a pan-TDP-43 antibody in WT mice) and human mutant TDP-43 (hTDP-43, recognized by an antibody specific to human TDP-43 in TDP-43M337V mice) were present in highly purified mitochondria isolated from mouse brain tissues (FIG. 9A). We confirmed that PM1 reached the central nervous system and substantially reduced the levels of endogenous mTDP-43 in mitochondria in brains of WT mice (data not shown). Despite similar levels in total lysates, both total TDP-43 (mTDP-43 plus hTDP-43) and hTDP-43 displayed significantly reduced expression in mitochondria fraction of hemizygous TDP-43M337V mice after PM1 treatment (FIG. 9A). Immunohistochemical analysis of TDP-43 using a pan-TDP-43 antibodies found TDP-43 accumulation in cytoplasm of cortical neurons selectively in layers 2 and 3 in hemizygous TDP-43M337V mice. Further double labeling with a specific antibody to the mitochondrial protein TOM20, revealed that mislocalized TDP-43 highly co-localized with mitochondria (FIG. 9B). Interestingly, TDP-43 cytoplasmic accumulation in TDP-43M337V mice disappeared after PM1 peptide infusion, suggesting the prevention of TDP-43 mislocalization by PM1 (FIG. 9B).

TDP-43 in mitochondria impairs mitochondrial bioenergetics, and the inhibition of TDP-43 mitochondrial localization suppresses its toxicity on mitochondrial function. Not surprisingly, the significant reduction of mitochondrial membrane potential ($m\Delta_\psi$) or oxygen consumption rate (OCR) noted in synaptic mitochondria isolated from brains of hemizygous TDP-43M337V mice, also was greatly alleviated by PM1 (FIG. 9C). PM1 alone did not change basal levels of $m\Delta_\psi$ or OCR, which was consistent with our previous findings. Intriguingly, 12 month old, but not 8 month old, hemizygous TDP-43M337V mice showed loss of cortical neurons most significantly also in cortical layers 2 and 3 (FIG. 9D, E and Supplemental FIG. 3, 8 month old mice not shown), correlating with TDP-43 mislocalization observed in these restricted cortical areas. After PM1 treatment, neuronal density in cortical layers 2 and 3 in hemizygous TDP-43$^{M337V}$ mice was comparable to WT mice or WT mice treated with cPM, indicating the complete prevention of mutant TDP-43$^{M337V}$-induced neuronal loss by PM1. No apparent neuronal loss was seen in hippocampus, cerebellum, or spinal cord (data not shown).

PM1 Reverses Motor Coordination and Cognitive Deficits in TDP-43M337V Tg Mice Considering the protective effect of PM1 peptide treatment on mitochondria and neurons, we finally addressed whether the suppression of TDP-43 mitochondrial localization by PM1 was able to reverse behavior deficits in hemizygous TDP-43M337V mice after symptom onset. 11-12 month old WT or transgenic mice were treated by PM1 or cPM via continuous subcutaneous infusion for 6 weeks. We confirmed that there was no significant difference in rotarod and beam-walk tests between cohorts of transgenic mice for PM1 and cPM infusion before treatment (p>0.1 for rotarod, data not shown; F1,16=1.51/0.18/0.01 for 12 mm square/12 mm round/9 mm square beam-walking, nonsignificant; Supplemental FIG. 10). Compared with WT mice treated with cPM (NTG/cPM group), transgenic mice with cPM infusion (Tg/cPM group) but not transgenic mice with PM1 infusion (Tg/PM1 group) exhibited significantly impaired rotarod and beam-walking performance (F2,21=11.93, p<0.001 for rotarod; F2,21=3.3, p<0.1 for 12 mm square beam; F2,21=8.8, p<0.01 for 12 mm round beam; F2,21=9.61, p<0.01 for 12 mm square beam; FIGS. 10A, B), indicating improved motor coordination and balance after PM1 infusion. No difference in grip strength, locomotor activities, or tactile sense was noted among all three groups (F2,21=1.803, nonsignificant for the open field test; F2,21=0.53 and F2,21=0.37, nonsignificant for fore-/hind-limb grip strength; F2,21=1.368, nonsignificant for the sticky paper test; FIG. 10C-E). Consistently, in addition to deficits in motor-coordinative function, significantly impaired memory was also seen in Tg/cPM mice (F2, 21=3.92, p<0.05 for Y-maze; F2,21=4.97, p<0.05 for T-maze; F2,21=1.43/7.22/5.16, p>0.1/<0.01/<0.05 for T1-3 session respectively in the novel object recognition test; F2,21=1.31/4.35/8.55/3.08/4.19, p>0.1/<0.05/<0.01/<0.1/ <0.05 for habituation and 1st-4th US 8 exposures during training session respectively in the fear conditioning test; F2,21=7.93, p<0.01 for context-dependent learning; F2,21=0.68, nonsignificant for no-cue period in cue-dependent learning; F2,21=7.84, p<0.01 for cue period in cue-dependent learning, FIGS. 11A-D). In contrast, Tg/PM1 showed greatly restored cognition to the levels of NTG/cPM mice, indicating that PM1 improved cognitive function in hemizygous TDP-43$^{M337V}$ mice. Extinction was not observed in the fear conditioning test in all groups probably because the CS stimuli (white noise) kept inducing freezing in mice (F8,84=1.065, p>0.1, data not shown). Taken together, these results indicate that the inhibition of TDP-43 mitochondrial localization by PM1 is sufficient to reverse motor coordination dysfunction and cognitive deficits in hemizygous TDP-43M337V mice after symptom onset.

Example 3

Our previous results showed that suppression of TDP-43 mitochondrial localization by PM1 peptide was sufficient to completely abolish motor and cognitive deficits in ALS and FTD animal models. In this Example, we tested the protective effect of PM1 peptide on motor and cognitive function in 5×FAD transgenic mice, widely-used mice recapitulating many Alzheimer's disease (AD)-related features. At 10-month old, non-transgenic (NTg) or 5×FAD transgenic mice (Tg) were subcutaneously infused with PM1 or control cPM peptide. We confirmed that 4 weeks after fusion, the level of TDP-43 in mitochondria was indeed reduced in brains of Tg mice treated with PM1 (FIG. 12A, B). At 11-month old, Tg mice treated with cPM demonstrated significant impairments in the performance on rotarod (motor function test) and the Barnes maze (spatial learning and memory test) manifested by the decreased ability to stay on the rotarod (FIG. 12C) and long latency to target hole (FIG.

12D) respectively. Excitingly, compared with Tg mice treated with cPM1, Tg mice treated with PM1 demonstrate significantly improved rotarod performance (FIG. 12C) and greatly reduce latency to target hole (FIG. 12D). As behavioral deficits in 5×FAD mice can be noted at as early at 6-month old, these results indicate that PM1 is also able to improve motor and cognitive function in 5×FAD transgenic mice after symptom onset.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A pharmaceutical composition comprising: a therapeutic agent that includes a synthetic therapeutic peptide of about 5 to about 10 amino acids in length that includes the amino acid sequence selected from the group consisting of SEQ ID NO: 1, SEQ ID NO: 3, and SEQ ID NO: 5 and a transport moiety that is linked to the therapeutic peptide and facilitates uptake of the therapeutic peptides by a cell, wherein the therapeutic peptide inhibits TDP-43 mediated disassembly of mitochondrial respiratory complex 1.

2. The composition of claim 1, the therapeutic peptide including the amino acid sequence of SEQ ID NO: 1 or SEQ ID NO: 7.

3. The composition of claim 1, the therapeutic peptide including the amino acid sequence of SEQ ID NO: 3 or SEQ ID NO: 8.

4. The composition of claim 1, the therapeutic peptide including the amino acid sequence of SEQ ID NO: 5 or SEQ ID NO: 9.

5. The composition of claim 1, the transport moiety comprising a TAT peptide.

6. The composition of claim 1, the therapeutic agent having the amino acid sequence selected from the group consisting of SEQ ID NOs: 12-17.

* * * * *

UNITED STATES PATENT AND TRADEMARK OFFICE
CERTIFICATE OF CORRECTION

| | | |
|---|---|---|
| PATENT NO. | : 11,124,553 B2 | Page 1 of 1 |
| APPLICATION NO. | : 16/090786 | |
| DATED | : September 21, 2021 | |
| INVENTOR(S) | : Xinglong Wang | |

It is certified that error appears in the above-identified patent and that said Letters Patent is hereby corrected as shown below:

In the Specification

Column 1, Lines 12-17, should read:
--GOVERNMENT FUNDING
This invention was made with government support under NS089604, AG044680, and NS085747 awarded by the National Institutes of Health. The government has certain rights in the invention.--

Signed and Sealed this
Twenty-second Day of April, 2025

Coke Morgan Stewart
*Acting Director of the United States Patent and Trademark Office*